(12) United States Patent
Gallant et al.

(10) Patent No.: US 12,721,694 B2
(45) Date of Patent: Sep. 1, 2026

(54) ROTATABLE FIDUCIAL MARKER ARRAY

(71) Applicant: Medivis, Inc., New York, NY (US)

(72) Inventors: Jesse Harrison Gallant, New York, NY (US); Osamah Choudhry, New York, NY (US); Christopher Morley, New York, NY (US); Florentin Jonas Liebmann, New York, NY (US)

(73) Assignee: Medivis, Inc., New York, NY (US)

( * ) Notice: Subject to any disclaimer, the term of this patent is extended or adjusted under 35 U.S.C. 154(b) by 0 days.

(21) Appl. No.: 18/900,079

(22) Filed: Sep. 27, 2024

(65) Prior Publication Data

US 2026/0090860 A1 Apr. 2, 2026

(51) Int. Cl.
*A61B 90/00* (2016.01)

(52) U.S. Cl.
CPC .................................... *A61B 90/39* (2016.02)

(58) Field of Classification Search
CPC ............ A61B 2090/3983; A61B 34/20; A61B 2034/2055; A61B 90/39; A61B 2034/2072; A61B 90/14; A61B 2090/363; A61B 2034/2065; A61B 2090/571; A61B 90/57; A61B 2034/207; A61B 2090/0811; A61B 2090/3991; A61B 90/06
See application file for complete search history.

(56) References Cited

U.S. PATENT DOCUMENTS

| | | | | |
|---|---|---|---|---|
| 7,993,353 B2 * | 8/2011 | Ro | ......................... | A61B 90/39 606/130 |
| 11,819,287 B2 * | 11/2023 | Lequette | ................ | A61B 34/25 |
| 2017/0105802 A1 * | 4/2017 | Taraschi | ................. | A61B 34/20 |
| 2017/0167514 A1 * | 6/2017 | Reutter | ..................... | F16B 2/12 |
| 2020/0360091 A1 * | 11/2020 | Murray | .................. | A61B 90/39 |

* cited by examiner

*Primary Examiner* — Anh Tuan T Nguyen
*Assistant Examiner* — Dean N Edun
(74) *Attorney, Agent, or Firm* — Cognition IP, P.C.; Edward Steakley; Justin White

(57) ABSTRACT

A fiducial marker array can have a rigid body and an array coupling arrangement. The rigid body can support a plurality of fiducial markers at fixed locations relative to each other along the rigid body to form an asymmetrical fixed positional arrangement of fiducial markers. The rigid body can include multiple array arms extending in multiple directions from a central region. The array coupling arrangement can be coupled to the rigid body at its central region and can be configured to couple the rigid body at its central region to a separate object such that the rigid body is rotatable relative to the separate object about a rotational axis extending through the central region. The array coupling arrangement can be further configured to facilitate locking the rigid body in place at one or more fixed rotational positions relative to the separate object, which can be a pivotable clamp.

20 Claims, 31 Drawing Sheets

10
200
212
220
230
110
160
100
150
121a
121b
130

10
212
160
110
200
220
100
150
140
250
170
230
240
212
121b
130

ROTATABLE FIDUCIAL MARKER ARRAY

CROSS-REFERENCE TO RELATED APPLICATIONS

This application is related to commonly owned U.S. patent application Ser. No. 18/900,106 filed on this same date of Sep. 27, 2024, titled "PIVOTABLE MEDICAL DEVICE CLAMP," and commonly owned U.S. patent application Ser. No. 18/900,052 also filed on this same date of Sep. 27, 2024, titled "MEDICAL DEVICE CHUCK WITH ROTATING FIDUCIAL MARKER ARRAY," which applications are hereby incorporated by reference in their entireties herein.

TECHNICAL FIELD

The present disclosure relates generally to medical devices, and more particularly to tools and devices used during medical procedures.

BACKGROUND

Planning and navigation are necessary for many medical procedures, such as live surgeries, practices, training, planning, scanning, and the like. Surgical teams typically have a plan based on medical imagery before ever entering an operating room. Conventional medical imaging systems such as X-ray, MRI, CT, and others have limitations regarding two-dimensional and three-dimensional images, however, and surgeons often need to consider numerous image views and slices to plan surgical procedures. Recent medical advances leverage these applications of medical imagery and surgical plans by using a computer-aided augmented reality environment, which can allow for the tracking of patients and physical instruments during surgical procedures by using reference (i.e., fiducial) markers and associated tracking components. Other medical procedures, such as ultrasound scanning, have also made use of computer-aided augmented reality environments involving tracked reference markers.

Unfortunately, conventional tracking systems are often limited in their ability to accurately generate, render, and apply virtual interactions in an augmented reality environment based on the orientations and positions of physical instruments with respect to those of physical landmarks identified on a patient body or other relevant location, particularly when things move during surgery or another relevant medical procedure. Unstable or unreliable positioning of fiducial markers can play a role in these issues. Limited or inaccurate tracking can then affect the overall performance of such systems during surgeries or other relevant medical procedures, and the need for accuracy in this regard can lead to overly cumbersome or complex attachment devices and systems.

While traditional ways of virtually tracking items during surgery or other medical procedures have worked well in the past, improvements are always helpful. In particular, what is desired are systems and devices that provide more robust and flexible ways to facilitate the stable and reliable positioning of fiducial markers during medical procedures in a simple and streamlined manner.

SUMMARY

It is an advantage of the present disclosure to provide medical systems and devices that provide more robust and flexible ways to facilitate the stable and reliable positioning of fiducial markers during medical procedures in a simple and streamlined manner. The disclosed features, apparatuses, systems, and methods relate to medical fiducial marker systems that can be used to locate fiducial marker arrays to different objects during surgeries and other medical procedures. In particular, the disclosed systems and methods can involve pivotable medical device clamps or medical device chucks, either of which can be clamped onto a surgical probe or other relevant object within a medical environment. These pivotable clamps and mechanical chucks can be configured to be coupled to one or more other medical devices or objects, such as a fiducial marker array. The disclosed systems and methods can also involve rotatable fiducial marker arrays configured to be coupled to such pivotable clamps and mechanical chucks.

In various embodiments of the present disclosure, a pivotable clamp can include a main body, first and second arm arrangements, a shaft, and a traveling component. The main body can have a top region, a first side region, a second side region opposite the first side region, and a pin extending between the first and second side regions. The first arm arrangement can have a top portion, a bottom portion, and a midsection configured to rotate about the pin in a first rotational direction. The second arm arrangement can be positioned opposite the first arm arrangement and can have a top portion, a bottom portion, and a midsection configured to rotate about the pin in a second rotational direction opposite the first rotational direction. The bottom portions of the first and second arm arrangements can include nonlinear regions. The shaft can extend through the top region of the main body. The traveling component can be coupled to the shaft beneath the top region and can be configured to travel along the shaft and to push against the first top portion of the first arm arrangement and the second top portion of the second arm arrangement when the traveling component travels sufficiently downward along the shaft. Pushing against the top portions of the arm arrangements can cause the arm arrangements to rotate about the pin such that the arm arrangement nonlinear regions clamp onto a cylindrical portion of a first separate object placed therebetween.

In various detailed embodiments, clamping onto the cylindrical portion can result in the pivotable clamp being unable to slide laterally along the cylindrical portion of the first separate object while still allowing the pivotable clamp to pivot about the cylindrical portion with respect to a longitudinal axis thereof. In some arrangements, the pivotable clamp can also include a twisting component coupled to the shaft above the top region, and this twisting component can be configured to facilitate rotation of the shaft. The shaft can include a threaded portion and the traveling component can be configured to interact with the threaded portion. The pivotable clamp can also include a clamp coupling component coupled to the first arm arrangement proximate its top portion, and this clamp coupling component can be configured to rotationally couple a second separate object to the pivotable clamp. The clamp coupling component can include one or more locking features configured to facilitate locking the second separate object at a fixed rotational position with respect to the pivotable clamp. In such arrangements, clamping onto the cylindrical portion and locking at the fixed rotational position can result in all points of the second separate object remaining at fixed distances from a longitudinal axis of the cylindrical portion when the pivotable clamp pivots about the cylindrical portion with respect to the longitudinal axis. In some arrangements, the pivotable clamp can be a pivotable medical device clamp and the first separate object can be a surgical probe.

In further embodiments, a pivotable medical device clamp can include a main body, first and second arm arrangements, a clamp coupling component, a shaft, a twisting component, and a traveling nut. The main body can have a top region, a first side region, a second side region opposite the first side region, and a pin extending from the first side region to the second side region. The first arm arrangement can have a top portion, a bottom portion, and a midsection configured to rotate about the pin in a first rotational direction. The second arm arrangement can be positioned opposite the first arm arrangement and can have a top portion, a bottom portion, and a midsection configured to rotate about the pin in a second rotational direction opposite the first rotational direction. The bottom portions of the first and second arm arrangements can include nonlinear regions. The clamp coupling component can be coupled to the first arm arrangement proximate its top portion and can be configured to rotatably couple the pivotable medical device clamp to a separate rotatable fiducial marker array. The shaft can extend through the top region of the main body and can include a threaded portion below the top region. The twisting component can be coupled to the shaft above the top region and can be configured to facilitate rotation of the shaft. The traveling nut can be coupled to the threaded portion of the shaft and can be configured to travel along the threaded portion and to push against the top portions of the arm arrangements when the traveling nut travels sufficiently downward along the threaded portion. Pushing against the top portions of the arm arrangements can cause the arm arrangements to rotate about the pin such that the arm arrangement nonlinear regions clamp onto a cylindrical portion of a separate medical device placed therebetween.

In various detailed embodiments, clamping onto the cylindrical portion can result in the pivotable medical device clamp being unable to slide laterally along the cylindrical portion of the separate medical device while still allowing the pivotable medical device clamp to pivot about the cylindrical portion with respect to a longitudinal axis thereof. The separate medical device can be a pedicle probe. The twisting component can be a thumbwheel. The shaft can include an enlarged portion held captive within the top region of the main body such that the shaft is configured to be readily rotated with respect to the main body but is not readily removable from the main body. The first arm arrangement can include a plurality of bottom portions, each bottom portion having a nonlinear region configured to clamp onto the separate medical device. The clamp coupling component can include one or more locking features configured to facilitate locking the rotatable fiducial marker array at a fixed rotational position with respect to the pivotable medical device clamp. Clamping onto the cylindrical portion of the separate medical device and locking the rotatable fiducial marker array at the fixed rotational position can result in all points of the rotatable fiducial marker array remaining at fixed distances from a longitudinal axis of the cylindrical portion when the pivotable medical device clamp pivots about the cylindrical portion with respect to the longitudinal axis. The pivotable medical device clamp can be configured to clamp onto a cylindrical portion having a diameter from about 5 to 25 mm.

In other embodiments, various methods of using a pivotable clamp are provided. Pertinent process steps can include locating a separate object within a pivotable clamp, forcing a traveling component down a shaft, closing arm bottom portions onto the separate object, and allowing the pivotable clamp to pivot but not slide laterally along the separate object. Methods can involve locating a cylindrical portion of the separate object between bottom portions of first and second arm arrangements of the pivotable clamp. The traveling component can be forced down a shaft of the pivotable clamp so that the traveling component pushes against top portions of the first and second arm arrangements. The bottom arm portions can be closed onto the cylindrical portion as the traveling component pushes against the top arm portions, and the arm bottom portions can include nonlinear regions that clamp onto the cylindrical portion. The pivotable clamp can then be allowed to pivot around but not slide laterally along the cylindrical portion while the nonlinear regions are clamped onto the cylindrical portion.

In various detailed embodiments, further process steps can include widening a distance between the arm bottom portions before locating the cylindrical portion therebetween, wherein the separate object is a separate medical device, rotatably coupling a rotatable fiducial marker array to the pivotable clamp, wherein the pivotable clamp is a pivotable medical device clamp, rotating the rotatable fiducial marker array with respect to the pivotable medical device clamp, locking the rotatable fiducial marker array at a set rotational position with respect to the pivotable medical device clamp, and calibrating fiducial marker positions relative to a longitudinal axis of the cylindrical portion and tip of the separate medical device. In various arrangements, the pivotable clamp can comprise the pivotable clamp as recited above such that it can include the main body having a top region, a first side region, a second side region opposite the first side region, and a pin extending between the first and second side regions, the first arm arrangement having the top portion, the bottom portion, and a midsection configured to rotate about the pin in a first rotational direction, the second arm arrangement positioned opposite the first arm arrangement and having the top portion, the bottom portion, and a midsection configured to rotate about the pin in a second rotational direction opposite the first rotational direction, the shaft extending through the top region of the main body, and the traveling component coupled to the shaft beneath the top region and configured to travel along the shaft and to push against the top portions of the first and second arm arrangements when the traveling component travels sufficiently downward along the shaft, wherein pushing against the top portions of the first and second arm arrangements causes the first and second arm arrangements to rotate about the pin such that the arm arrangement nonlinear regions clamp onto the cylindrical portion of the separate object.

In additional embodiments of the present disclosure, a fiducial marker array can include at least a rigid body and an array coupling arrangement. The rigid body can be configured to support a plurality of fiducial markers at fixed locations relative to each other along the rigid body to form an asymmetrical fixed positional arrangement of fiducial markers. The rigid body can include multiple array arms extending in multiple directions from a central region. The array coupling arrangement can be coupled to the rigid body at its central region and can be configured to couple the rigid body at its central region to a separate object such that the rigid body is rotatable relative to the separate object about a rotational axis extending through the central region. The array coupling arrangement can be further configured to facilitate locking the rigid body in place at one or more fixed rotational positions relative to the separate object.

In various detailed embodiments, the fiducial marker array can also include the plurality of fiducial markers, which can include infrared reflective spheres, retroreflective spheres, infrared-emitting diodes, or any combination thereof. The fiducial marker array can also include a plurality of fiducial marker couplers, each of which can removably couple one of the plurality of fiducial markers to the rigid body at one of the fixed locations. In specific arrangements, the multiple array arms can include three or more array arms and the plurality of fiducial markers can include four or more fiducial markers. Each of the plurality of array arms can include at least one of the fixed locations to support one of the plurality of fiducial markers. The array coupling arrangement can include a shaft having a threaded portion, the shaft being extendable through an opening in the rigid body central region and configured such that its threaded portion mates within a threaded opening at the separate object. The rigid body can be configured to rotate about the shaft when the shaft is extended through the rigid body central region opening and is mated within the threaded opening of the separate object. The array coupling arrangement can further include a thumbwheel coupled to the shaft at an end opposite the threaded portion, the thumbwheel being configured to rotate the shaft to couple and uncouple the shaft from the threaded opening of the separate object. The array coupling arrangement can also include one or more array locking features along a bottom surface of the rigid body at its central region. The one or more array locking features can be configured to interact with one or more separate locking features on the separate object to facilitate locking the rigid body in place at a fixed rotational position relative to the separate object.

In further detailed embodiments, the separate object can be a pivotable clamp configured to clamp onto a cylindrical portion of a separate tool such that the pivotable clamp can pivot about a longitudinal axis of the cylindrical portion. The separate tool can be a medical device or surgical probe, such as a pedicle probe. In some arrangements, clamping the pivotable clamp onto the cylindrical portion and locking the fiducial marker array at a fixed rotational position relative to the pivotable clamp can result in all of the fiducial markers remaining at fixed distances from a tip of the separate object and also from the longitudinal axis of the cylindrical portion when the pivotable clamp pivots about the cylindrical portion with respect to the longitudinal axis. The array coupling arrangement can also be configured to allow rotation of the fiducial marker array relative to the separate object without uncoupling from the separate object. The array coupling arrangement can be configured to facilitate locking the rigid body in place at eight or more different fixed rotational positions relative to the separate object.

In still further embodiments, a medical fiducial marker system can include a pivotable medical device clamp and a rotatable fiducial marker array. The pivotable medical device clamp can be configured to clamp onto a cylindrical portion of a separate medical device during a medical procedure. Clamping onto the cylindrical portion can result in the pivotable clamp being unable to slide laterally along the cylindrical portion while still allowing the pivotable clamp to pivot about the cylindrical portion with respect to a longitudinal axis thereof. The rotatable fiducial marker array can be configured to support a plurality of fiducial markers and to rotatably couple to the pivotable medical device clamp. Clamping the pivotable medical device clamp onto the cylindrical portion of the separate medical device and locking the rotatable fiducial marker array at a fixed rotational position relative to the pivotable medical device clamp can result in each of the plurality of fiducial markers remaining at a fixed distance from a tip of the separate medical device and from the longitudinal axis when the pivotable clamp pivots about the cylindrical portion.

In various detailed embodiments, the rotatable fiducial marker array can include a rigid body and an array coupling arrangement. The rigid body can be configured to support the plurality of fiducial markers at fixed locations relative to each other along the rigid body to form an asymmetrical fixed positional arrangement of fiducial markers, wherein the rigid body includes multiple array arms extending in multiple directions from a central region. The array coupling arrangement can be coupled to the rigid body at its central region and can be configured to couple the rigid body at its central region to the pivotable medical device clamp such that the rigid body is rotatable relative to the pivotable medical device clamp about a rotational axis extending through the central region. The array coupling arrangement can be further configured to facilitate locking the rigid body in place at one or more fixed rotational positions relative to the pivotable medical device clamp.

In further detailed embodiments, the pivotable medical device clamp can include a main body having a top region, a first side region, a second side region opposite the first side region, and a pin extending from the first side region to the second side region, a first arm arrangement having a top portion, a bottom portion, and a midsection configured to rotate about the pin in a first rotational direction, a second arm arrangement positioned opposite the first arm arrangement and having a top portion, a bottom portion, and a midsection configured to rotate about the pin in a second rotational direction opposite the first rotational direction, wherein the bottom portions of the first and second arm arrangements include nonlinear regions, a clamp coupling component coupled to the first arm arrangement proximate its top portion, wherein the clamp coupling component is configured to rotatably couple the pivotable medical device clamp to the rotatable fiducial marker array, a shaft extending through the top region of the main body, the shaft including a threaded portion below the top region, a twisting component coupled to the shaft above the top region, wherein the twisting component is configured to facilitate rotation of the shaft, and a traveling nut coupled to the threaded portion of the shaft and configured to travel along the threaded portion and to push against the first and second top portions of the first and second arm arrangements when the traveling nut travels sufficiently downward along the threaded portion, wherein pushing against the top portions of the arm arrangements causes the arm arrangements to rotate about the pin such that the arm arrangement nonlinear regions clamp onto the cylindrical portion of the separate medical device placed therebetween.

In yet further embodiments, various methods of using a rotatable fiducial marker array are provided. Process steps can include facilitating a rotational coupling, adjusting a rotational orientation, and locking the rotational coupling at a fixed rotational position. The rotational coupling can be facilitated between a rotatable fiducial marker array and a separate object. The rotatable fiducial marker array can include a rigid body having a central region and multiple array arms extending therefrom configured to support a plurality of fiducial markers at fixed locations relative to each other to form an asymmetrical fixed positional arrangement of fiducial markers. The rotational orientation of the rotatable fiducial marker array can be adjusted relative to the separate object from a first rotational position to a second rotational position. The rotational coupling can be locked at a fixed rotational position between the rotatable fiducial marker array and the separate object. The locked rotational coupling prevents rotational movement of the rotatable fiducial marker array relative to the separate object.

In various detailed embodiments, the separate object can be a pivotable clamp configured to clamp onto a cylindrical portion of a separate tool. The pivotable clamp can be a pivotable medical device clamp and the separate tool can be a medical device such as a pedicle probe. Additional process steps can include removably coupling the plurality of fiducial markers to the rotatable fiducial marker array at the fixed locations and calibrating fiducial marker positions on the rotatable fiducial marker array relative to both a longitudinal axis of the separate tool cylindrical portion and a tip of the separate tool when the rotational coupling is locked at the fixed rotational position and the pivotable clamp is clamped onto the separate tool cylindrical portion. The rotatable fiducial marker array can further include an array coupling arrangement coupled to the rigid body at its central region. The array coupling arrangement can be configured to couple the rigid body at its central region to the separate object such that the rigid body is rotatable relative to the separate object about a rotational axis extending through the central region.

In additional embodiments of the present disclosure, a mechanical chuck can include at least a main body, a plurality of jaws, and a chuck adjustment mechanism. The main body can have a front region, middle region, back region, and central opening extending through the entire main body from the front region to the back region along a main body longitudinal axis. The middle region of the main body can include a captive collar arrangement configured to hold a rotating sleeve component at the middle region while allowing the rotating sleeve component to rotate around the main body longitudinal axis relative to the main body. The plurality of jaws can be located at the front region and can be configured to clamp onto a cylindrical portion of a separate object that extends through the central opening along the main body longitudinal axis and past both the front and back regions of the main body. The cylindrical portion of the separate object can define a cylindrical longitudinal axis. The chuck adjustment mechanism can be coupled to the plurality of jaws and configured to adjust the spacing of each of the jaws relative to the main body longitudinal axis. Adjusting the spacing to clamp the plurality of jaws onto the cylindrical portion of the separate object can result in the cylindrical portion being unable to pivot or to move laterally relative to the main body.

In various detailed embodiments, the mechanical chuck can be a medical device chuck, the separate object can be a surgical probe, and the rotating sleeve component can be configured to rotatably couple to a fiducial marker array. In some arrangements, the mechanical chuck can include the rotating sleeve component. The captive collar arrangement can include a cylindrical outer surface around at least a portion of the middle region and raised features at the front and back of the middle region outer surface that prevent the rotating sleeve component from sliding laterally off the front or back of the middle region outer surface. The raised features can prevent the rotating sleeve component from sliding laterally along the middle region outer surface. The rotating sleeve component can have an inner diameter that matches the outer diameter of the middle region outer surface. The chuck adjustment mechanism can include a scroll plate having an internal spiral groove configured to radially move each of the plurality of jaws simultaneously and symmetrically when a chuck adjustment body holding the plurality of jaws is rotated with respect to the scroll plate. In some arrangements, the cylindrical longitudinal axis can coincide with the main body longitudinal axis when the plurality of jaws are clamped onto the cylindrical portion of the separate object.

In various further embodiments, a medical fiducial marker system can include a medical device chuck and a rotating fiducial marker array. The medical device chuck can be configured to clamp onto a cylindrical portion of a separate medical device during a medical procedure where the cylindrical portion defines a cylindrical longitudinal axis. Clamping onto the cylindrical portion can result in the medical device chuck being unable to slide laterally along the cylindrical portion or pivot about the cylindrical portion with respect to the cylindrical longitudinal axis. The rotating fiducial marker array can have a plurality of fiducial markers and can be coupled to the medical device chuck such that the rotating fiducial marker array is configured to rotate around the medical device chuck. Clamping the medical device chuck onto the cylindrical portion of the separate medical device can result in each of the fiducial markers remaining at fixed distances from both the cylindrical longitudinal axis and a tip of the separate medical device when the fiducial marker array rotates around the medical device chuck.

In various detailed embodiments, the medical device chuck can include a main body, a plurality of jaws, and a chuck adjustment mechanism. The main body can have a front region, middle region, back region, and central opening extending through the entire main body from the front region to the back region along a main body longitudinal axis. The middle region of the main body can include a captive collar arrangement configured to hold a rotating sleeve component at the middle region while allowing the rotating sleeve component to rotate relative to the main body around the main body longitudinal axis. The plurality of jaws can be located at the front region and can be configured to clamp onto the cylindrical portion of the separate medical device that extends through the central opening along the main body longitudinal axis and past both the front and back regions of the main body. The chuck adjustment mechanism can be coupled to the plurality of jaws and configured to adjust the spacing of each of the plurality of jaws relative to the main body longitudinal axis. Adjusting the spacing to move the plurality of jaws radially inward can clamp the plurality of jaws onto the cylindrical portion of the separate medical device. In some arrangements, the medical fiducial marker system can also include the rotating sleeve component. The rotating fiducial marker array can be rotatably coupled to the rotating sleeve component.

In further detailed embodiments, the rotating fiducial marker array can include a rigid body and an array coupling arrangement. The rigid body can be configured to support the plurality of fiducial markers at fixed locations relative to each other along the rigid body to form an asymmetrical fixed positional arrangement of fiducial markers. The rigid body can include multiple array arms extending in multiple directions from a central region. The array coupling arrangement can be coupled to the rigid body at its central region and can be configured to couple the rigid body at its central region to the rotating sleeve component such that the rigid body is rotatable relative to the rotating sleeve component about a rotational axis extending through the central region. The array coupling arrangement can be further configured to facilitate locking the rigid body in place at one or more fixed rotational positions relative to the rotating sleeve component. The captive collar arrangement can include a cylindrical outer surface around at least a portion of the middle region and raised features at the front and back of the middle region outer surface that prevent the rotating sleeve component from sliding laterally off the front or back of the middle region outer surface. The cylindrical longitudinal axis can coincide with the main body longitudinal axis when the plurality of jaws are clamped onto the cylindrical portion of the separate object. In some arrangements, the rotating fiducial marker array can be configured to be held stationary while the medical device chuck is clamped onto the cylindrical portion of the separate medical device and the medical device chuck and cylindrical portion of the separate medical device are spun together about the cylindrical longitudinal axis during the medical procedure.

In still further embodiments, methods of using a mechanical chuck can include locating a cylindrical portion of a separate object within the chuck, manipulating a chuck adjustment mechanism, closing a plurality of jaws onto the cylindrical portion, and allowing relative rotation between the chuck and a rotating sleeve component. The cylindrical portion of the separate object can define a longitudinal axis and can be located within a central opening of the mechanical chuck, which can have a plurality of jaws, a chuck adjustment mechanism, and a main body with front and back sides. The central opening can extend from the front to back sides of the main body. The cylindrical portion can be located between the plurality of jaws and can extend through the central opening past both the front and back sides of the main body. The chuck adjustment mechanism can be manipulated while the cylindrical portion is located between the jaws and extends past both the front and back sides of the main body. The jaws can include contact regions that clamp onto the cylindrical portion of the separate object such that the chuck cannot slide laterally along the cylindrical portion or pivot about the longitudinal axis relative to the cylindrical portion. Relative rotation between the chuck and the rotating sleeve component coupled to the chuck can be allowed while the contact regions are clamped onto the cylindrical portion, and the relative rotation can be about the longitudinal axis.

In various detailed embodiments, the cylindrical portion of the separate object can form a combined unit with the mechanical chuck regarding the relative rotation with the rotating sleeve. The rotating sleeve component can have a fiducial marker array rotatably coupled thereto. The rotating sleeve component can be held within a captive collar arrangement at the main body of the mechanical chuck, and the rotating sleeve component can be configured to facilitate a full range of rotational motion between the main body and the rotating sleeve component. The mechanical chuck can be a medical device chuck and the separate object can be a separate medical device, such as a pedicle probe or other surgical probe. Additional process steps can include capturing the rotating sleeve component within a captive collar arrangement at the main body of the medical device chuck, coupling a rotatable fiducial marker array to the rotating sleeve component. locking the rotatable fiducial marker array at a set rotational position with respect to the rotating sleeve component, opening a distance between the plurality of jaws. calibrating fiducial marker positions on the rotatable fiducial marker array relative to both the longitudinal axis of the cylindrical portion and a tip of the separate medical device, and spinning the cylindrical portion of the separate medical device and the medical device chuck as a combined unit while holding the rotating sleeve component stationary.

Other apparatuses, methods, features, and advantages of the disclosure will be or will become apparent to one with skill in the art upon examination of the following figures and detailed description. It is intended that all such additional apparatuses, methods, features and advantages be included within this description, be within the scope of the disclosure, and be protected by the accompanying claims.

BRIEF DESCRIPTION OF THE DRAWINGS

The included drawings are for illustrative purposes and serve only to provide examples of possible structures, arrangements, and methods of use for medical fiducial marker systems having rotatable fiducial marker arrays and pivotable medical device clamps that are configured for use with separate medical devices. These drawings in no way limit any changes in form and detail that may be made to the disclosure by one skilled in the art without departing from the spirit and scope of the disclosure.

DETAILED DESCRIPTION

Figure 1A:
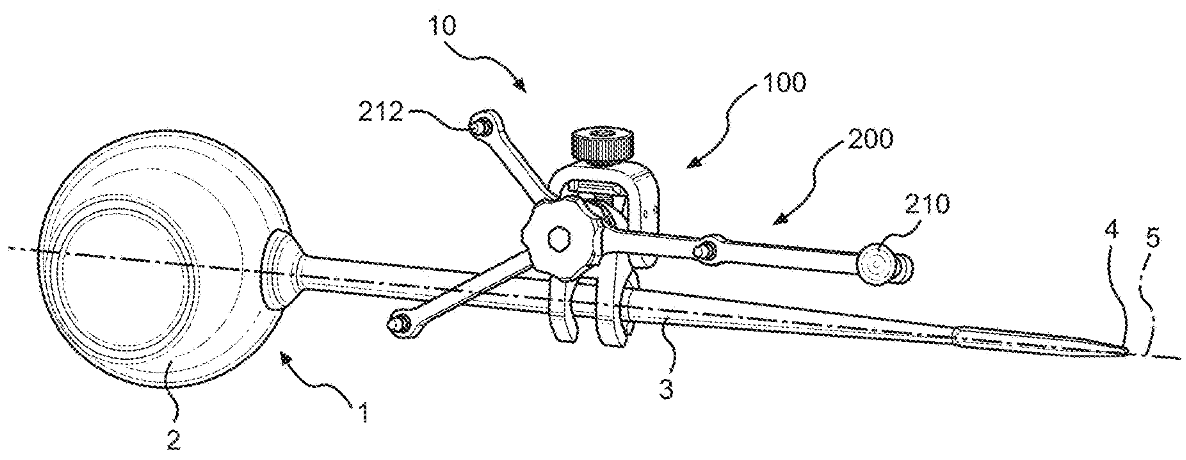
FIG. 1A illustrates in front perspective view an example medical fiducial marker system having a rotatable fiducial marker array and a pivotable medical device clamp as being clamped to a separate medical device according to one embodiment of the present disclosure.

Exemplary applications of apparatuses, systems, and methods according to the present disclosure are described in this section. These examples are being provided solely to add context and aid in the understanding of the disclosure. It will thus be apparent to one skilled in the art that the present disclosure may be practiced without some or all of these specific details provided herein. In some instances, well known process steps have not been described in detail in order to avoid unnecessarily obscuring the present disclosure. Other applications are possible, such that the following examples should not be taken as limiting. In the following detailed description, references are made to the accompanying drawings, which form a part of the description and in which are shown, by way of illustration, specific embodiments of the present disclosure. Although these embodiments are described in sufficient detail to enable one skilled in the art to practice the disclosure, it is understood that these examples are not limiting, such that other embodiments may be used, and changes may be made without departing from the spirit and scope of the disclosure.

As is generally well known, modem surgeries and other medical procedures are sometimes facilitated by using a computer-aided augmented reality environment. Fiducial markers can be used for tracking patients, medical devices, or other physical instruments during surgeries or other medical procedures. Such fiducial markers can be part of overall systems that can include specialized lighting arrangements, cameras, and computing systems. Attachment devices are often used to locate the fiducial markers in place relative to the patient or other physical device or instrument, and unstable or unreliable positioning of these markers can result in the reduced effectiveness of the overall computer-aided augmented reality environment. The disclosed device clamps and fiducial marker arrays are specifically designed to facilitate the stable and reliable positioning of fiducial markers in a simple and streamlined manner for a surgery or other medical procedure benefitting from such a computer-aided augmented reality.

The present disclosure generally relates in various embodiments to features, apparatuses, systems, and methods of use for fiducial marker systems having clamps and fiducial marker arrays. Such clamps can be pivotable clamps or other suitable attachment devices that can be configured to clamp onto or otherwise attach to objects while also providing for the ability to be coupled to fiducial marker arrays. Specific arrangements that involve surgical or medical environments can involve a pivotable medical device clamp configured to pivotably clamp to a cylindrical portion of a surgical probe or other medical object while also having a rotatable fiducial marker array rotatably coupled thereto.

In various detailed embodiments of the present disclosure, a novel pivotable medical device clamp can be configured to clamp onto a cylindrical portion of a pedicle probe such that the clamp can be pivoted about the probe but cannot slide along a longitudinal axis of the probe. A rotatable fiducial marker array can be rotatably coupled to the pivotable medical device clamp and locked at a particular rotational position relative to the clamp such that all fiducial markers on the array are then at measurable set distances from both the tip and the longitudinal axis of the pedicle probe. Since the clamp does not slide along the length of the probe these set distances from each marker to the probe tip and probe longitudinal axis remain constant throughout a medical procedure regardless of whether the clamp pivots around the probe. Uses of the disclosed systems can involve pedicle screw insertion procedures, for example.

Although various embodiments disclosed herein discuss a pivotable medical device clamp in conjunction with a rotatable fiducial marker array as part of an overall surgical fiducial marker system for use in an augmented reality aided medical procedure, such as a pedicle screw insertion procedure, for example, it will be readily appreciated that the disclosed features, apparatuses, systems, and methods can also be used in conjunction with other devices and equipment that can leverage various advantages the disclosed pivotable clamps, fiducial marker arrays, and overall systems. It is thus specifically contemplated that other clamps, fiducial marker arrays, clamped objects, and alternative applications may also apply. For example, the disclosed pivotable clamps can be used to clamp to other probes or other cylindrical objects for both surgical and non-surgical uses, such as during examination and testing procedures. Other devices and equipment that can be coupled to the disclosed pivotable clamps can include lighting arrangements, sensing devices, or other desired equipment. Furthermore, while the disclosed fiducial marker arrays are contemplated for use involving rotatably coupling a fiducial marker array to a pivotable clamp during a medical procedure, it is specifically contemplated that the same rotatable fiducial marker arrays can also be coupled in a similar manner to other types of clamps, medical devices, or other tools or objects. Other applications, arrangements, and extrapolations beyond the illustrated embodiments are also contemplated.

Medical Fiducial Marker System

Figure 1B:
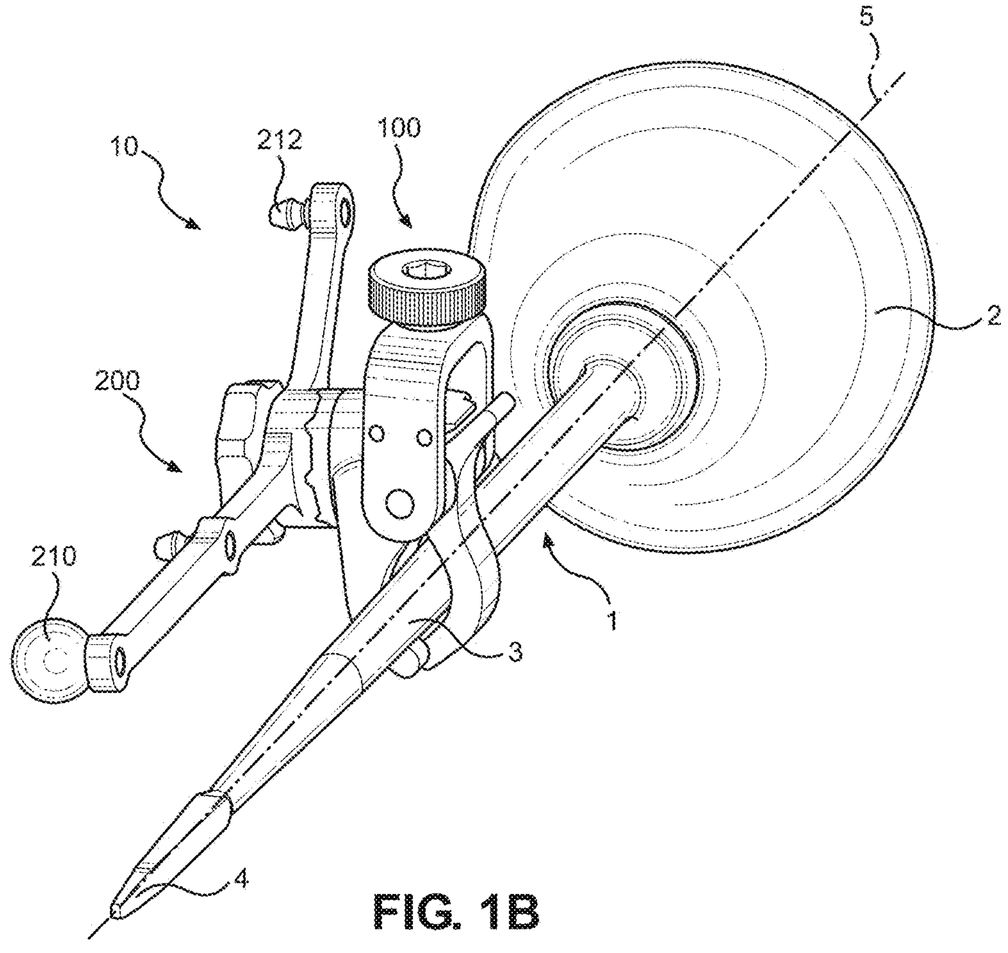
FIG. 1B illustrates in side perspective view the medical fiducial marker system of FIG. 1A according to one embodiment of the present disclosure.

Referring first to FIGS. 1A and 1B, an example medical fiducial marker system having a rotatable fiducial marker array and a pivotable medical device clamp as being clamped to a separate medical device is illustrated in front perspective and side perspective views respectively. In general, medical fiducial marker system 10 can be configured to fix multiple fiducial markers 210 at set locations in three-dimensional space with respect to a separate object such as separate medical device 1 so that a surgery or other medical procedure can be performed while tracking the separate device within an augmented reality environment using the fiducial markers. In some arrangements, the fiducial markers can be fixed at set distances relative to a longitudinal axis and tip or endpoint of the separate medical device 1. Medical fiducial marker system 10 can generally include a pivotable medical device clamp 100 and a rotatable fiducial marker array 200 arranged for this purpose, as detailed below.

Separate medical device 1 can be a pedicle probe, for example, which can be configured for use in pedicle screw insertion procedures or other pedicle surgeries as are generally well known. Again, separate medical device 1 can alternatively be a different type of surgical probe, another medical device, or any other suitable separate object. Separate medical device 1 (e.g., a pedicle probe) can include a handle 2, shaft or cylindrical portion 3, and tip 4, among other possible features. Cylindrical portion 3 can define a longitudinal axis 5 about which the entire separate medical device 1 can be rotated or spun. Although a pedicle probe is shown for purposes of illustration and discussion, it will be appreciated that other types of probes, tools, instruments, and medical devices can alternatively be separate devices with which medical fiducial marker system 10 can be used.

As shown, pivotable medical device clamp 100 can be clamped onto a cylindrical portion 3 of separate medical device 1, which again can be a pedicle probe. Rotatable fiducial marker array 200 can be rotatably coupled to pivotable medical device clamp 100 and can be configured to position multiple fiducial markers 210 with respect to separate medical device 1. Although only one fiducial marker 210 is shown in FIGS. 1A and 1B for purposes of illustration, it will be understood that identical or similar fiducial markers can be removably mounted or otherwise coupled to each of the remaining marker posts 212 on rotatably fiducial marker array 200. Each of multiple fiducial markers 210 can be arranged such that it is located at a fixed distance from both tip 4 and longitudinal axis 5 of separate medical device 1.

This can be accomplished by firmly clamping pivotable medical device clamp 100 onto cylindrical portion 3 such that the pivotable medical device clamp does not slide laterally along the cylindrical portion, since lateral sliding would then alter the distances between the fiducial markers

210 and the separate medical device tip 4. This can also be accomplished by locking rotatable fiducial marker array 200 at a set rotational position with respect to the pivotable medical device clamp, since relative rotation of the marker array after setting could then also alter distances between the fiducial markers and the separate medical device tip. In some arrangements, pivotable medical device clamp 100 can be allowed to pivot about (but not slide along) cylindrical portion 3, since pivoting does not alter the distances between fiducial markers 210 and separate medical device tip 4 and also does not alter the distances between the fiducial markers and longitudinal axis 5. As will be readily appreciated, this ability can also be reflected by keeping pivotable medical device clamp 100 in place and spinning cylindrical portion 3 of separate medical device 1 within the clamp.

Figure 2A:
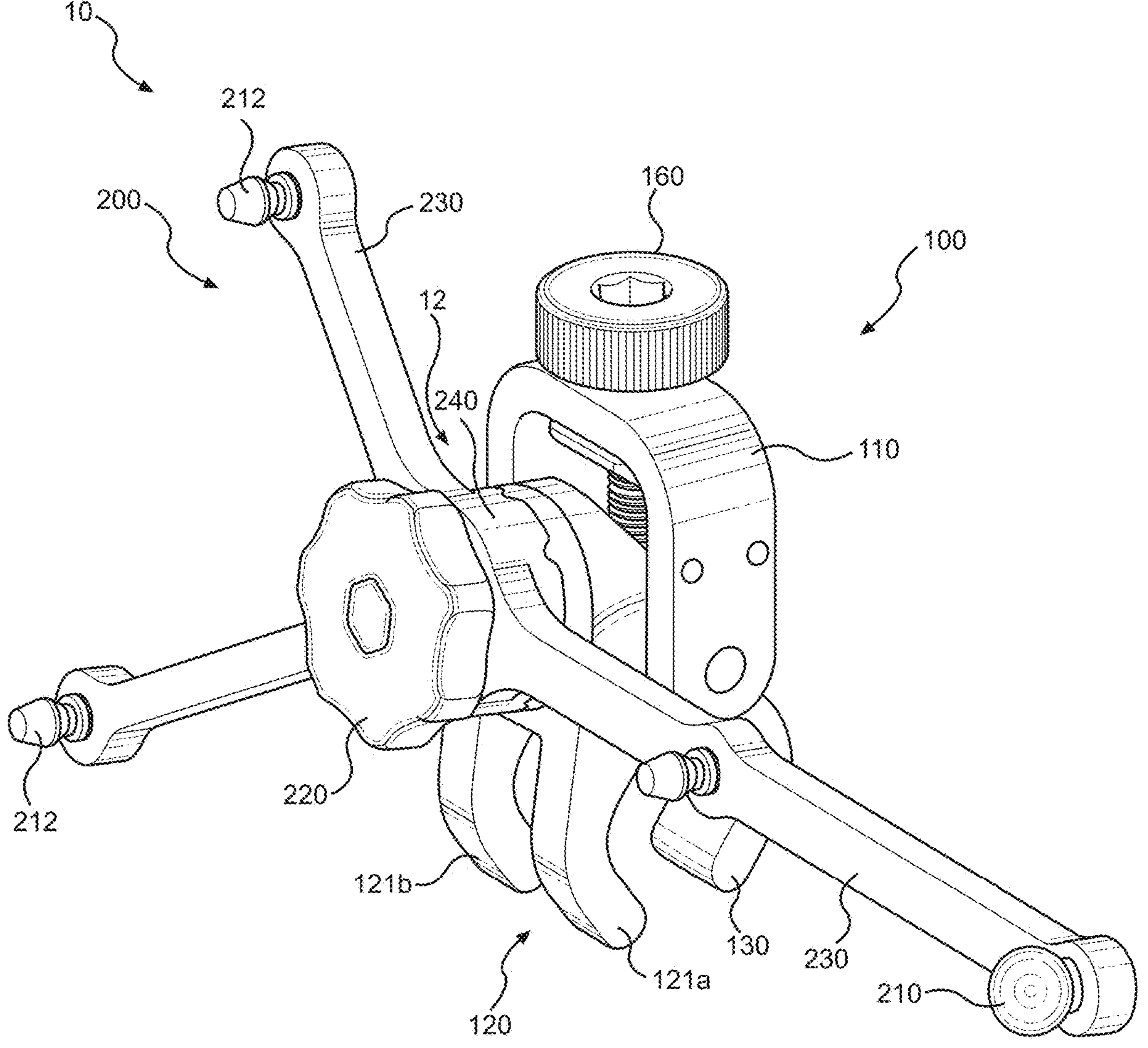
FIG. 2A illustrates in front perspective view the medical fiducial marker system of FIG. 1A without a separate medical device according to one embodiment of the present disclosure.
Figures 2B, 2C:
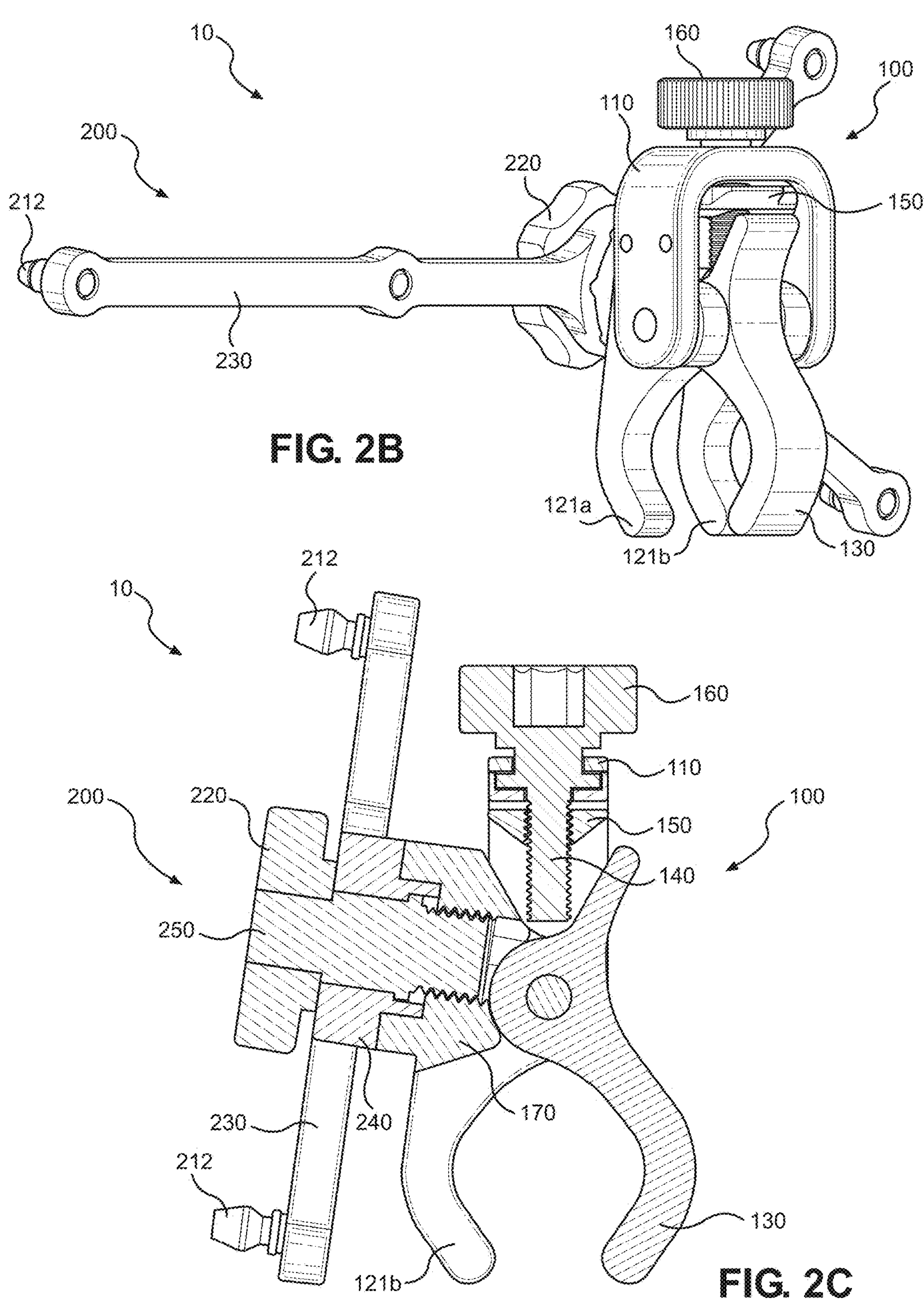
FIG. 2B illustrates in rear perspective view the medical fiducial marker system of FIG. 2A according to one embodiment of the present disclosure.
FIG. 2C illustrates in side cross-section view the medical fiducial marker system of FIG. 2A according to one embodiment of the present disclosure.

Continuing with FIGS. 2A-2C, the medical fiducial marker system of FIG. 1A is shown without a separate medical device in front perspective, rear perspective, and side cross-section views respectively. Medical fiducial marker system 10 can be identical or substantially similar to that which is described and illustrated above, albeit without the presence of a separate medical device. Again, medical fiducial marker system 10 can generally include pivotable medical device clamp 100 and rotatable fiducial marker array 200 that can be rotatably coupled to the clamp, such as by way of an array coupling arrangement. As shown, rotatable fiducial marker array 200 can be locked in place rotationally with respect to pivotable medical device clamp 100 by way of array thumbwheel 220 and rotational locking arrangement 12, interactions and features of which are provided in greater detail below.

In various embodiments, pivotable medical device clamp 100 can include at least main body 110, first arm arrangement 120, second arm arrangement 130, shaft 140, traveling component 150, twisting component 160, and clamp coupling component 170, among various other components and features. First arm arrangement 120 can have a plurality of bottom portions 121*a*, 121*b* to facilitate improved clamping onto a cylindrical portion of a separate object placed between first and second arm arrangements 120, 130. Second arm arrangement 130 can have a single bottom portion, although multiple bottom portions can alternatively be used. Similarly, first arm arrangement 120 can have more than two bottom portions in some embodiments. While clamp coupling component 170 is shown as being located proximate the top of first arm arrangement 120, it will be readily appreciated that this clamp coupling component can alternatively be located at various other places on pivotable medical device clamp 100, such as proximate the top of second arm arrangement 130 for example.

Rotatable fiducial marker array 200 can include multiple array arms 230 extending in multiple directions from array central region 240. Rotatable fiducial marker array 200 can be configured to position multiple fiducial markers 210 with respect to a separate object clamped by pivotable medical device clamp 100, which separate object can again be a pedicle probe or other device having a cylindrical portion. Rotatable fiducial marker array 200 can be rotatably coupled to pivotable medical device clamp 100 by way of an array coupling arrangement that can be configured to interact with clamp coupling component 170 of the clamp. Such an array coupling arrangement can include array thumbwheel 220 coupled to array shaft 250 having a threaded portion and array locking features (not shown) located along a bottom surface of array central region 240, as set forth in greater detail below.

In various embodiments, fiducial markers 210 can include infrared reflective balls or other retroreflective spheres, infrared-emitting diodes, or other items suitable for use with optical tracking systems. Each fiducial marker 210 can be coupled to an array arm 230 of rotatable fiducial marker array 200 using a threaded coupler 212 that can be inserted into an opening of the fiducial marker as well as an opening along the array arm. The locations of fiducial markers 210 can form an asymmetrical pattern that will not cause ambiguity or confusion with the optical tracking system reading the locations of the fiducial markers. Although three array arms 230 having locations for four fiducial markers 210 are shown for purposes of illustration, it will be understood that a suitable rotational fiducial marker array may also have more or fewer fiducial markers arranged along more or fewer array arms that can in turn be arranged into other patterns or shapes. Additional features and functionalities regarding rotatable fiducial marker array 200 are set forth in greater detail below.

Pivotable Medical Device Clamp

Figure 3A:
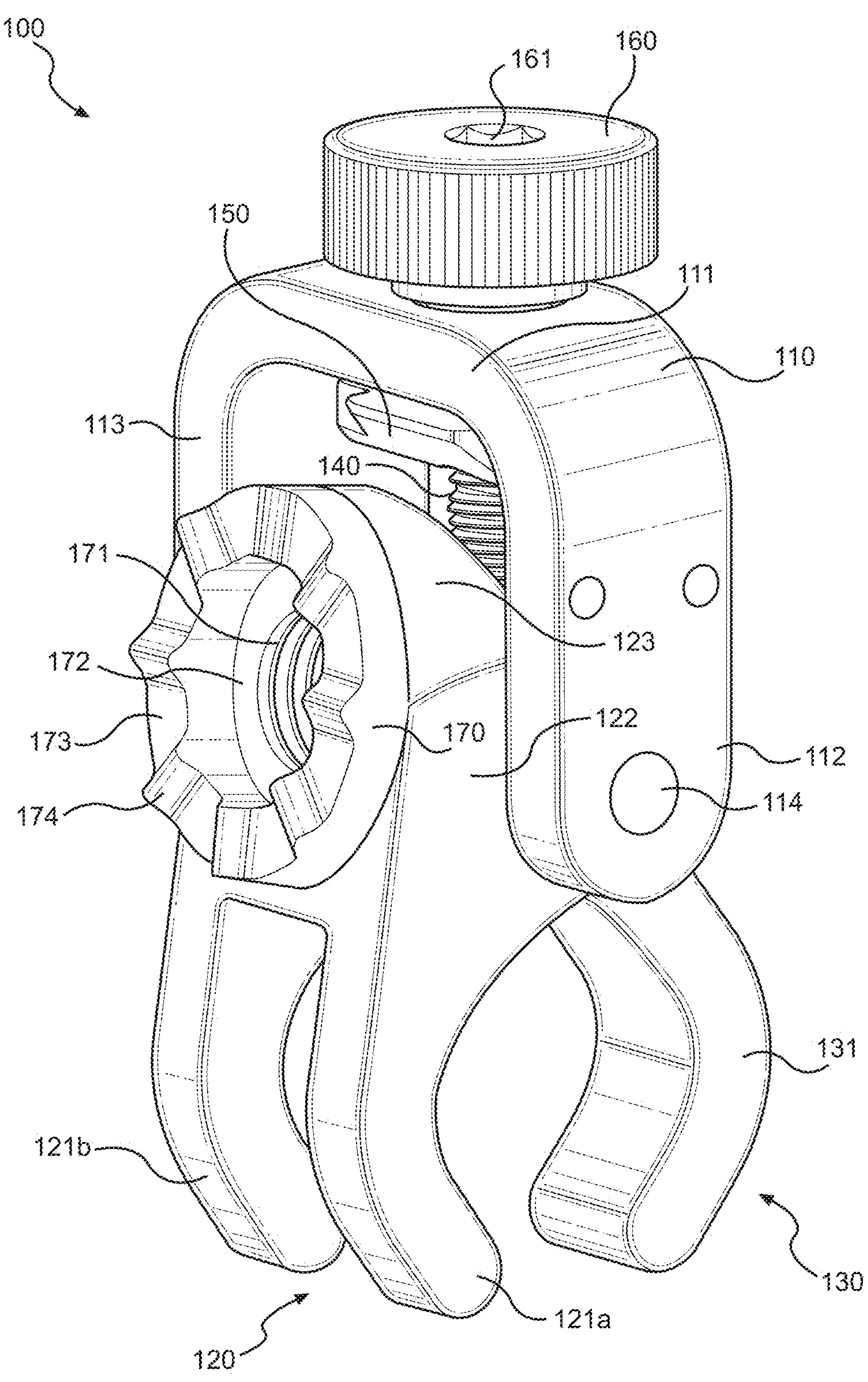
FIG. 3A illustrates in front perspective view an example pivotable medical device clamp according to one embodiment of the present disclosure.
Figure 3B:
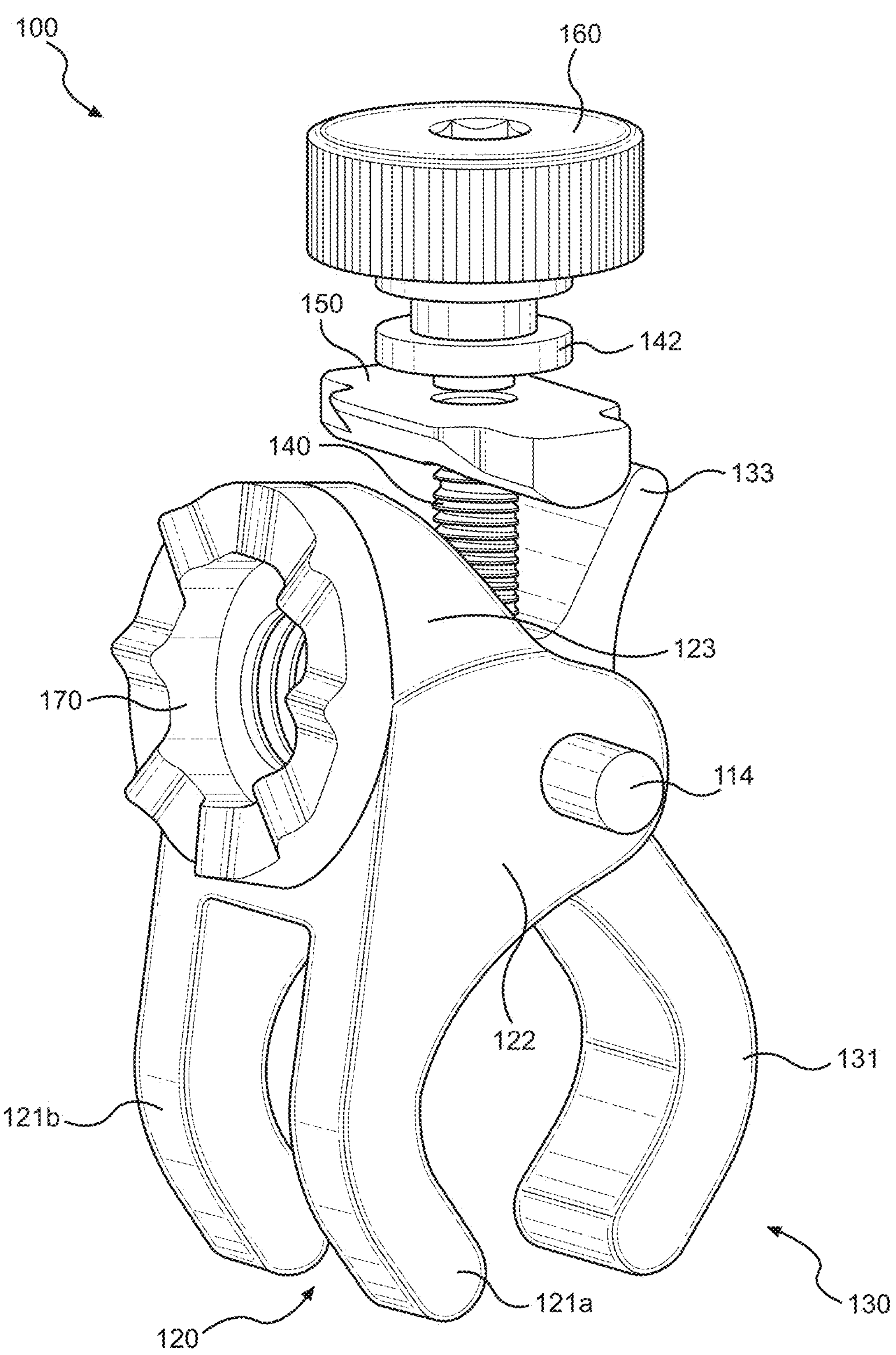
FIG. 3B illustrates in front side perspective view the pivotable medical device clamp of FIG. 3A with its main body removed according to one embodiment of the present disclosure.
Figure 3C:
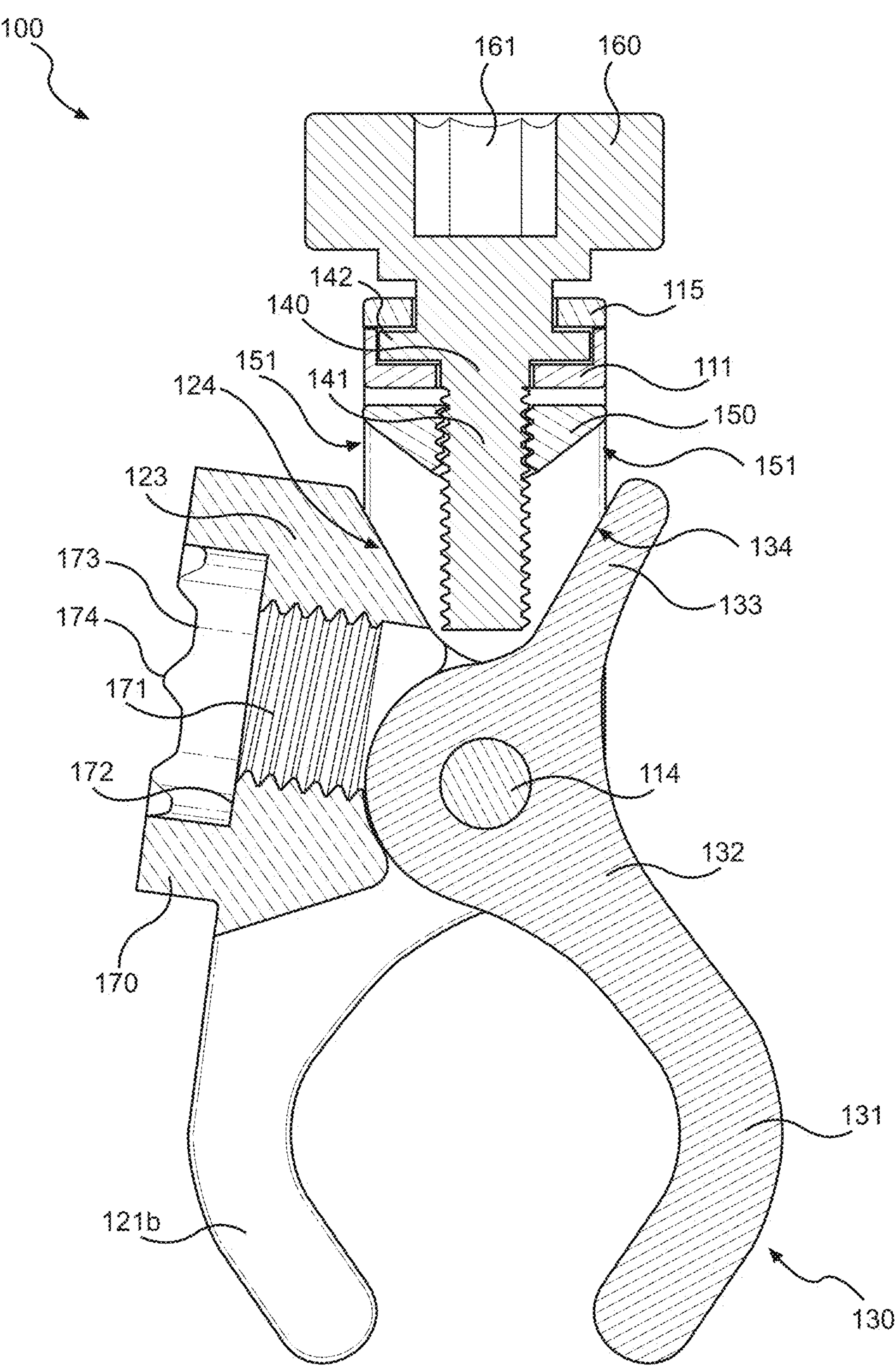
FIG. 3C illustrates in side cross-section view the pivotable medical device clamp of FIG. 3A according to one embodiment of the present disclosure.

Turning next to FIGS. 3A-3C, an example pivotable medical device clamp is shown in multiple front perspective views and a side cross-section view. FIG. 3A illustrates the entire medical device clamp, while FIG. 3B shows the pivotable medical device clamp with its main body removed for purposes of illustration. Pivotable medical device clamp 100 can be more generally referred to as a pivotable clamp, such as for other applications that do not involve clamping onto a medical device, and this clamp can alternatively be called a "universal adapter" or "cylindrical adapter" in these and other applications. Again, pivotable medical device clamp 100 can include various primary components, such as a main body 110, first arm arrangement 120, second arm arrangement 130, shaft 140, traveling component 150, twisting component 160, and clamp coupling component 170.

Main body 110 can have a top region 111, a first side region 112, a second side region 113 opposite the first side region, and a pin 114 extending between the first and second side regions. In some arrangements main body 110 can also include a top bracket 115 located across outer surfaces of top region 111, first side region 112, and second side region 113. First arm arrangement 120 can have a plurality of bottom portions 121*a*, 121*b*, a midsection 122, and a top portion 123. Second arm arrangement 130 can have at least one bottom portion 131, a midsection 132, and a top portion 133. As shown, one or more of arm bottom portions 121*a*, 121*b*, and 131 can include curved or otherwise nonlinear regions to facilitate clamping onto a separate cylindrical object or a cylindrical portion of a separate object placed therebetween. The sizes and shapes of these arm bottom portions 121*a*, 121*b*, 131 can be dimensioned to allow for clamping onto cylindrical objects or portions thereof having varying diameters. For example, cylindrical portions of separate objects having diameters from about 5 to 25 mm can be clamped successfully by pivotable medical device clamp 100. Other diameter sizes are also possible.

First and second arm midsections 122 and 132 can be placed onto pin 114 and configured such that their respective first and second arm arrangements 120, 130 can rotate about the pin. This can involve, for example, both midsections 122, 132 having openings through which pin 114 can extend. Pivotable medical device clamp 100 can be configured such that first and second arm arrangements 120, 130 can rotate together in opposite directions about pin 114 to either open or close the space between arm bottom portions 121*a*, 121*b* and 131. When clamping onto a separate object, for example, first arm arrangement 120 can be configured to rotate about pin 114 in a first rotational direction while second arm arrangement 130 can be configured to rotate about the pin in a second rotational direction that is opposite the first rotational direction. These rotational movements can be done simultaneously and symmetrically at least with respect to arm bottom portions 121*a*, 121*b* and 131 when clamping onto a separate object cylindrical portion. First and second arm arrangements 120, 130 can also be configured to rotate in opposite directions together to create more space between or "unclamp" arm bottom portions 121*a*, 121*b* and 131 to release the separate object, as will be readily appreciated.

In various embodiments, pivotable medical device clamp 100 can be considered to be in an "open" position when arm bottom portions 121*a*, 121*b* and 131 are sufficiently spaced apart such that a separate object cylindrical portion can be inserted through the bottom distal ends of all bottom portions into the space therebetween. Similarly, pivotable medical device clamp 100 can be considered to be in an "closed" position when arm bottom portions 121*a*, 121*b* and 131 are moved together such that the separate object cylindrical portion is firmly clamped between the arm bottom portions. The exact spacing or distance between arm bottom portions 121*a*, 121*b* and 131 can be facilitated by an adjustable spacing arrangement that can include shaft 140, traveling component 150, and twisting component 160. In general, traveling component 150 can be forced downward along shaft 140 to push against top portions 123, 133 of first and second arm arrangements 120, 130 by rotating the shaft in a clamping direction, which can cause the arm top portions to push apart and correspondingly cause the first and second arm arrangements to rotate about the pin such that the arm bottom portions 121*a*, 121*b* and 131 move closer together. This can result in the curved or otherwise nonlinear regions of arm bottom portions 121*a*, 121*b* and 131 clamping onto a cylindrical portion of a separate object placed therebetween.

Shaft 140 can extend through top region 111 of main body 110 and can include a threaded portion 141 onto which traveling component 150 can be coupled. Traveling component 150 can be a traveling nut, for example, which can have an internally threaded opening that is configured to interact with shaft threaded portion 141 such that the traveling nut can travel up and down the threaded portion when shaft 140 is rotated. Traveling component 150 and some or all of shaft threaded portion 141 can be located beneath top region 111 and between first and second side regions 112, 113 of main body 110, such that the range of travel for the traveling nut or component can be limited by a bottom surface of main body top region and the maximum rotatable distance possible for first and second arm arrangements 120, 130. Twisting component 160 can be coupled to shaft 140 above the top region 111 and can be configured to facilitate rotation of the shaft in both forward and backward rotational directions to force traveling component 150 up and down shaft threaded portion 141. Twisting component 160 can be a thumbwheel or thumbscrew, for example, and can be integrally formed with shaft 140 in some embodiments. Twisting component 160 can include an opening 161 at an upper surface thereof, which opening can accommodate a hex wrench or other suitable tool that can be used to facilitate twisting or rotating the twisting component and thus shaft 140. As such, thumbwheel or other twisting component 160 can be configured to be adjusted manually, automatically such as robotically controlled, or both.

As shown, traveling nut or component 150 can be sized and shaped to facilitate pushing interactions with top portions 123, 133 of first and second arm arrangements 120, 130. For example, traveling component 150 can have bottom surfaces 151 that are angled and/or curved to facilitate engagements with inner surfaces 124, 134 of arm top portions 123, 133. These arm top portion inner surfaces 124, 134 can also be angled and/or curved to facilitate engagements with traveling component bottom surfaces 151, which can include sliding or other movement between surfaces as traveling component 150 continues to travel and push downward while arm top portions 123, 133 are thereby pushed outward. Traveling nut or component 150 can be forced downward and pushed against arm top portions 123, 133 simultaneously such that the arm top portions are moved outward together, first and second arm arrangements 120, 130 are rotated together in opposite directions, and arm bottom portions 121*a*, 121*b* and 131 are closed or clamped together simultaneously and evenly. Again, traveling component 150 can be forced downward by rotating shaft 140 in the proper "clamping" or "closing" direction. As will be readily appreciated, shaft 140 can then be rotated in an opposite "opening" direction to force traveling component 150 upward along the shaft to then release the clamped object.

In some arrangements, shaft 140 can also include extension ring 142 or other enlarged portion integrally formed with the shaft or coupled thereto. Shaft 140 can be arranged such that extension ring 142 is held captive within the top region of main body 110, such as between top region 111 and top bracket 115 coupled thereto. This arrangement can allow shaft 140 to rotate freely with respect to main body 110 without allowing the shaft to fall out of or be readily removed from pivotable medical device clamp 100. In some arrangements, top bracket 115 can be removable from the rest of main body 110, such as by way of one or more pins, screws, snaps, or other suitable connectors, which removability can facilitate assembly and disassembly of the shaft captive arrangement and overall pivotable medical device clamp 100.

Clamp coupling component 170 can generally be configured to rotationally couple a separate object to the pivotable clamp. In specific arrangements, clamp coupling component 170 can be coupled to first arm arrangement 120 proximate its top portion 123 and can be configured to rotationally couple rotatable fiducial marker array 200 to pivotable medical device clamp 100. Clamp coupling component 170 can be coupled to or integrally formed with an arm arrangement or any other suitable component of the pivotable clamp. Clamp coupling component 170 can include threaded central opening 171, larger center opening 172, mating face 173, and ridges 174 extending therefrom. In some arrangements, clamp coupling component 170 can include a crown attachment having the larger center opening 172, mating face 173, and ridges 174. Such embodiments can involve threaded central opening 171 extending into first arm arrangement 120 or any other suitable location on pivotable medical device clamp 100 where clamp coupling component 170 is formed by way of a crown attachment.

Threaded central opening 171 can be configured to accept a threaded portion of a thumbscrew or other coupling item on a rotatable fiducial marker array or other separate device to be rotatably coupled to pivotable medical device clamp 100. The crown attachment or feature can include a raised portion around its circumference with larger center opening 172 inside, mating face 173 facing away from the clamp, and ridges 174 spaced around the circumference and configured to mate with appropriately sized divots or recesses on a corresponding mating feature of the rotatable fiducial marker array or other separate device. Such a crown design can be configured to allow for various set rotational positionings of the rotatable fiducial marker array or other separate device coupled to pivotable medical device clamp 100. For example, eight ridges 174 can be equally spaced around the circumference of mating face 173 such that a coupled rotatable fiducial marker array can be rotated to eight different rotational positions relative to the clamp. The thumbscrew or other coupling item on the rotatable fiducial marker array or other separate device can then be tightened into threaded central opening 171 to lock the array in place rotationally.

Figure 4:
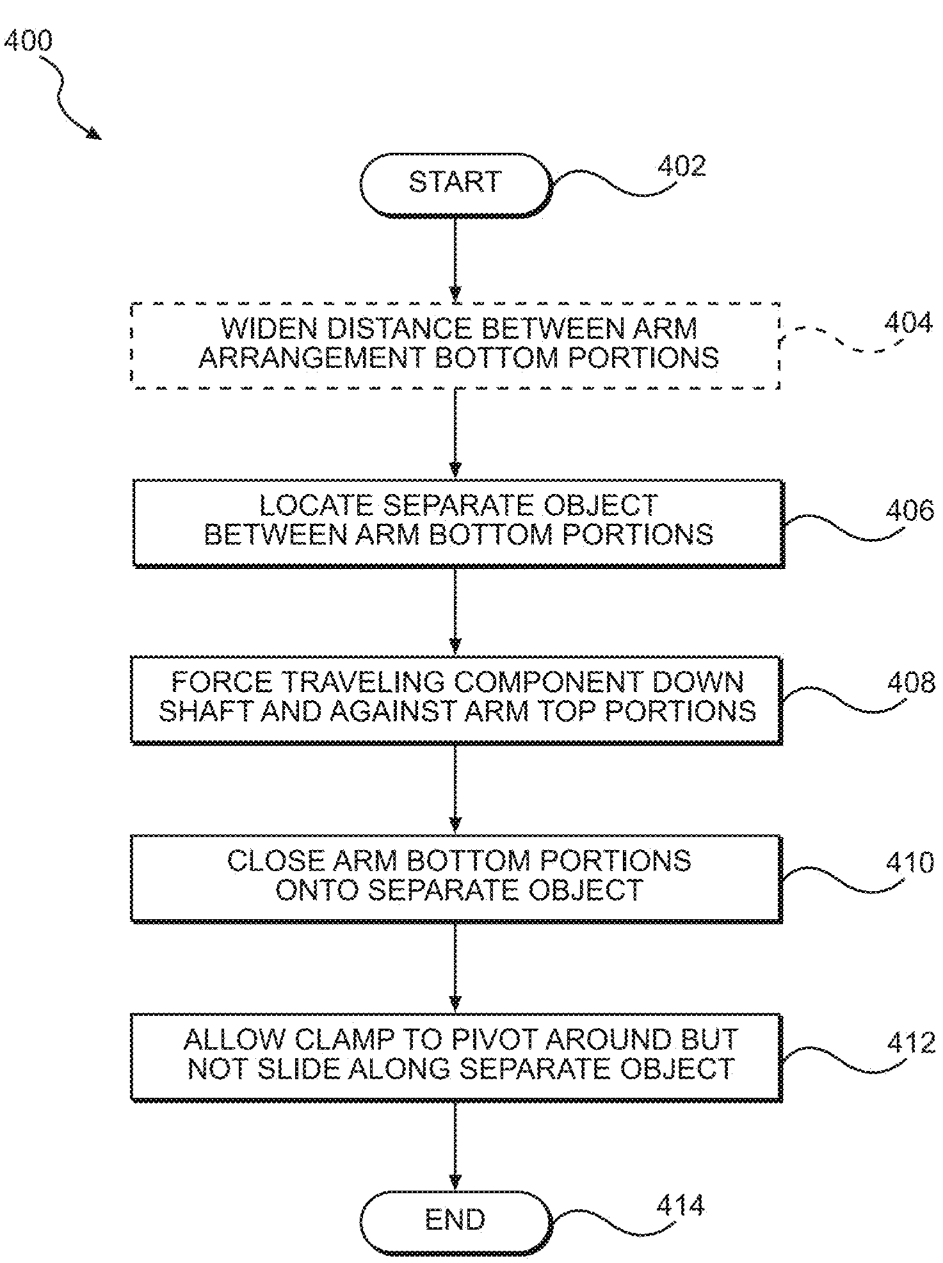
FIG. 4 illustrates a flowchart of an example summary method of using a pivotable clamp according to one embodiment of the present disclosure.

Continuing with FIG. 4, a flowchart of an example summary method of using a pivotable clamp is provided. Summary method 400 can represent one broad aspect for overall methods of use for a pivotable clamp, and it will be understood that various other steps, features, and details of such a broad aspect and overall methods of use are not provided here for purposes of simplicity. While the pivotable clamp can be a pivotable medical device clamp designed for use with a pedicle probe or other medical device as disclosed herein, it is contemplated that the pivotable clamp can also be used with other objects and in other environments and applications.

After a start step 402, a first optional process step 404 can involve widening or increasing a distance between arm arrangements of a pivotable clamp. This can involve arm arrangements having bottom portions configured to clamp onto a cylindrical portion of a separate object. The separate object can be a medical device such as a pedicle probe, although other types of objects are also possible. Step 404 can be optional in some situations, such as where the pivotable clamp is already situated such that the arm arrangements are sufficiently far apart to be able to locate the cylindrical portion of the separate object between the arm bottom portions. Step 404 can be performed manually or automatically in some cases, such as where a separate robotic system can be configured to push apart the bottom portions of the arm arrangements.

At the following process step 406, the separate object can be located within the pivotable clamp. This can involve placing the cylindrical portion of the separate object between the bottom portions of the arm arrangements. The bottom portions can include curved or otherwise nonlinear regions configured to wrap sufficiently around the cylindrical portion of the separate object, which can be placed between these curved or otherwise nonlinear regions such that clamping can then be accomplished. Step 406 can be manually or automatically performed, such as where a separate robotic system can be configured to move and locate the separate object appropriately.

At subsequent process step 408, a traveling component can be forced down a shaft of the pivotable clamp such that the traveling component contacts and pushes against top portions of the arm arrangements. Forcing the traveling component down the shaft in such a manner can be accomplished in a variety of ways. For example, the shaft can include a threaded portion and the traveling component can be a traveling nut that travels down the shaft when the shaft is rotated in place. Rotating the shaft can involve, for example, rotating a thumbwheel coupled to the shaft in a clamp closing direction that pushes the traveling nut against the arm top portions. Step 408 can be manually or automatically performed, such as where a separate robotic system can be configured to operate a thumbwheel of the pivotable clamp.

The next process step 410 can involve closing the arm bottom portions onto the cylindrical portion of the separate object. This can be done as the traveling component pushes against the arm top portions, such as where pushing against the arm top portions pushes them away from each other and the arm arrangements include midsections configured to pivot about a pin so that the arm bottom portions move closer to each other. The arm bottom portions can include curved or otherwise nonlinear regions that clamp onto the separate object cylindrical portion such that the separate object is then unable to fall out of the pivotable clamp. Step 410 can be manually or automatically performed, such as where closing the arm bottom portions toward each other and onto the cylindrical portion is a natural physical consequence of pushing the traveling component against the arm top portions.

At the following process step 412, the pivotable device clamp can be allowed to pivot around but not slide laterally along the cylindrical portion of the separate object while the nonlinear regions are clamped onto the cylindrical portion. Such a function can be a feature of the pivotable clamp being fully clamped onto the cylindrical portion of the separate object. Step 412 can be manually or automatically performed, such as where the pivotable but non-slidable ability of the pivotable device clamp is a natural physical consequence of closing the arm bottom portions together and clamping them onto the cylindrical portion of the separate object. This can be facilitated by one or more features on the nonlinear regions of the arm bottom portions that prevent or limit lateral sliding of the cylindrical portion along the arm bottom portions. The method can then end at end step 414.

Figure 5A:
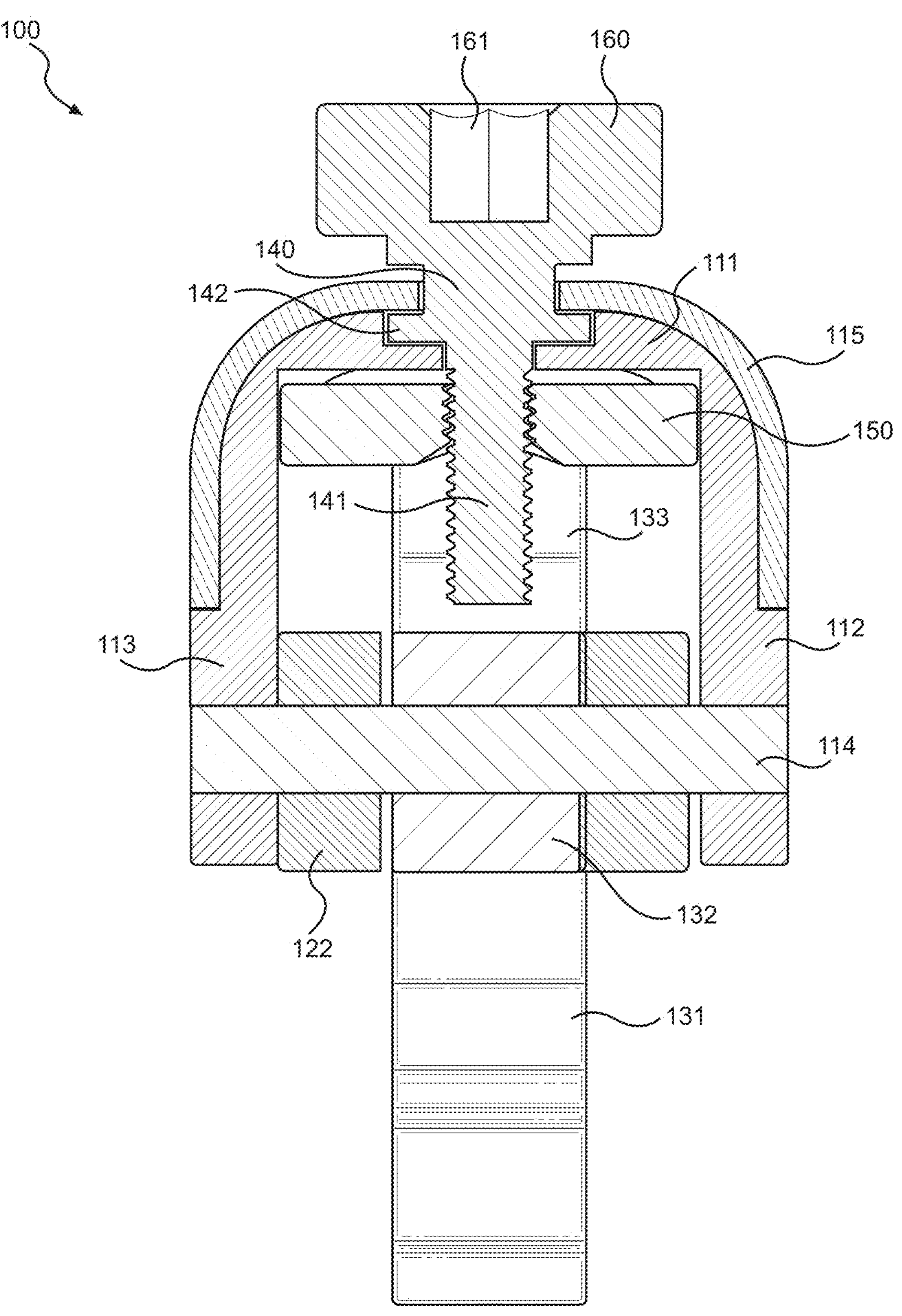
FIG. 5A illustrates in front cross-section view the pivotable medical device clamp of FIG. 3A according to one embodiment of the present disclosure.
Figure 5B:
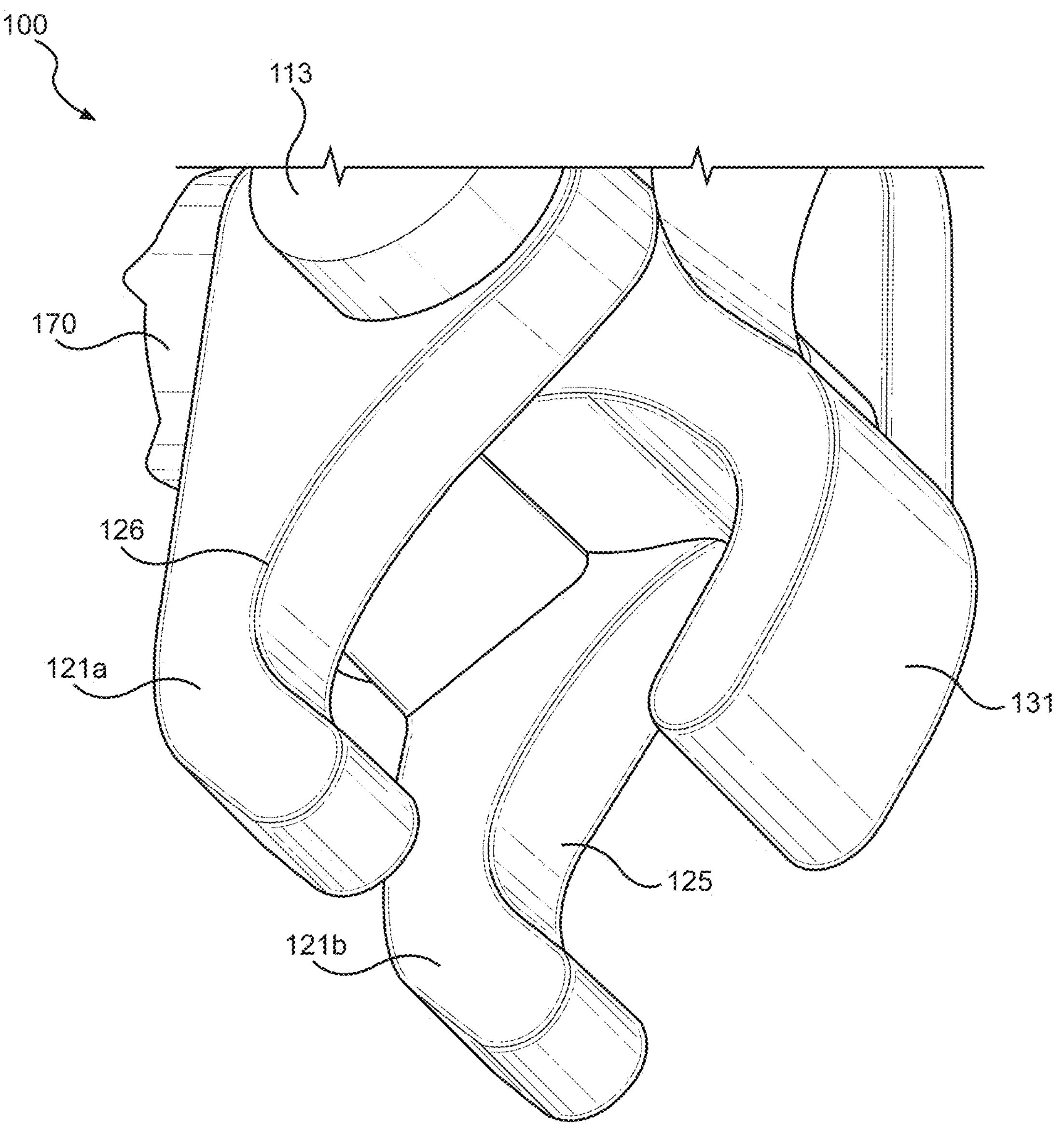
FIG. 5B illustrates in bottom perspective view arm arrangements of the pivotable medical device clamp of FIG. 3A according to one embodiment of the present disclosure.

FIG. 5A illustrates the pivotable medical device clamp in front cross-section view, while FIG. 5B shows the pivotable medical device clamp arm bottom portions in bottom perspective view. FIG. 5A provides a different illustrative view for various components and features detailed above for pivotable medical device clamp 100. As shown, traveling nut or component 150 can be sized and shaped within the main body such that it extends laterally to abut or nearly contact first and second side regions 112, 113 of the main body as the nut travels up and down threaded portion 141 of shaft 140. Such an arrangement can provide for proper alignment and orientation of traveling component 150 and structural stability for the overall pivotable medical device clamp 100 as the clamp is adjusted and set at different arm positions.

As noted above and as can also be seen with respect to FIG. 3C, adjusting the clamp 100 by pushing traveling component 150 downward along shaft 140 can result in pushing evenly and simultaneously against arm top portions 123, 133 of both arm arrangements 120, 130. This pushing can be done evenly and symmetrically such that the longitudinal axis of the cylindrical object being clamped remains directly beneath pin 114 and may involve the cylindrical object rising or lowering along a vertical line beneath the pin as the cylindrical object remains centered between the arm arrangements. In various arrangements, a given pivotable medical device clamp 100 can be configured to accommodate cylindrical objects of varying diameters or "tool sizes." In addition, the sizes and shapes of arm arrangements 120, 130 can vary from one overall clamp 100 to another to provide even greater flexibility in the sizes of probes, tools, or objects that can be clamped within a given set of arm arrangements. For example, the range of cylinder diameters that can be clamped between arm arrangements 120, 130 as shown in FIGS. 1A through 5B can be 5-15 mm. Similar clamps with larger arm arrangements can be configured to accommodate 8-25 mm diameter cylindrical tools, as another example. In such varying sized and shaped pivotable clamps, the size and length of shaft 140 can also be varied based on the amount of stroke length desired for traveling component 150.

Referring to FIG. 5B specifically, arm bottom portions 121*a*, 121*b* and 131 can be sized, shaped, and formed from one or more materials that facilitate the ability of a cylindrical portion of a separate object placed therebetween to spin in place while clamped without the arm bottom portions being able to slide laterally along the cylindrical portion. Alternatively, this can be viewed as the clamp being pivotable about the cylindrical portion. Features to facilitate such a pivotable but non-slidable outcome during clamping can include one or more one or more arm bottom portion surfaces 125 formed from a high friction material, one or more arm bottom portion edges 126 that can be hard, unfilleted, or have other features that prevent or limit any lateral sliding ability while clamped onto the cylindrical object. Other arm bottom portion features can include sharp edges or features that bite into the cylindrical tool to prevent or limit lateral sliding. Some or all arm bottom portions can include these features. In addition, arm bottom portions 121*a*, 121*b* and 131 can be curved or otherwise nonlinear in nature such that more surface areas of these arm bottom portions contact the cylindrical portion in a lateral direction than in a vertical direction.

Figure 6:
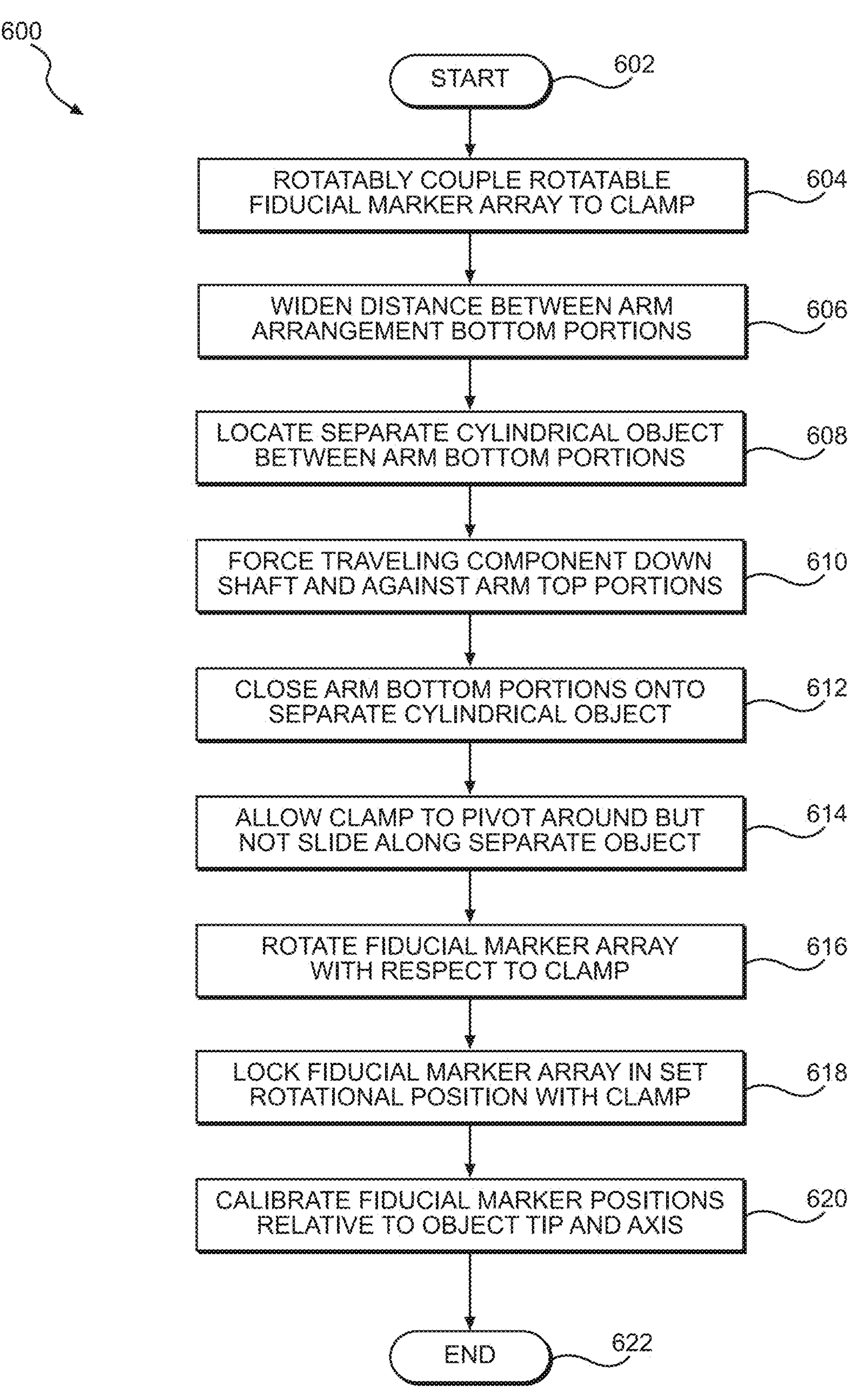
FIG. 6 illustrates a flowchart of an example detailed method of using a pivotable medical device clamp according to one embodiment of the present disclosure.

Next, FIG. 6 provides a flowchart of an example detailed method 600 of using a pivotable medical device clamp. Detailed method 600 can represent one possible detailed way of using a pivotable medical device clamp, and it will be understood that various other steps, features, and details of such a detailed method are not provided here for purposes of simplicity. Detailed method 600 can also include some or all steps and details of summary method 400 above, as will be readily appreciated. After a start step 602, a first process step 604 can involve rotatably coupling a rotatable fiducial marker array to the pivotable medical device clamp. This can involve inserting and rotating a threaded end of a marker array thumbscrew into a threaded central opening of a clamp coupling component, such as that which is set forth above. Step 604 can be manually or automatically performed, such as where a separate robotic system can be configured to handle the rotatable fiducial marker array so as to insert and rotate an array thumbscrew into the threaded opening of a clamp coupling component, as detailed above.

A following process step 606 can involve widening or increasing a distance between arm arrangements of the pivotable medical device clamp. This can be identical or similar to step 404 above using arm arrangements having bottom portions configured to clamp onto a cylindrical portion of a separate object. Again, the separate object can be a medical device such as a pedicle probe, although other types of medical devices and other objects are also possible. Step 606 can be performed manually or automatically in some cases, such as where a separate robotic system can be configured to push apart the bottom portions of the arm arrangements.

At subsequent process step 608, the separate object or a cylindrical portion thereof can be located within the pivotable medical device clamp. This can again involve placing the cylindrical portion of the separate object between the bottom portions of the arm arrangements, which bottom portions can include curved or otherwise nonlinear regions configured to wrap sufficiently around the cylindrical portion such that clamping can then be accomplished. Step 608 can be manually or automatically performed, such as where a separate robotic system can be configured to move and locate the separate object appropriately.

The next process step 610 can involve forcing a traveling component downward along a shaft of the pivotable medical device clamp such that the traveling component contacts and pushes against top portions of the arm arrangements. Forcing the traveling component down the shaft can be accomplished in a variety of ways, such as where the shaft includes a threaded portion and the traveling component can be a traveling nut that travels down the shaft when the shaft is rotated in place. Rotating the shaft can involve, for example, rotating a thumbwheel coupled to the shaft in a clamp closing direction that pushes the traveling nut against the arm top portions. Step 610 can be manually or automatically performed, such as where a separate robotic system can be configured to operate a thumbwheel of the pivotable medical device clamp.

At a following process step 612, the arm bottom portions can be closed onto the cylindrical portion of the separate medical device or other object. This can be done as the traveling component pushes against the arm top portions, such as where pushing against the arm top portions pushes them away from each other and the arm arrangements include midsections configured to pivot about a pin so that the arm bottom portions move closer to each other. The arm bottom portions can include curved or otherwise nonlinear regions that clamp onto the separate object cylindrical portion such that the separate object is then unable to fall out of the pivotable clamp. Step 612 can be manually or automatically performed, such as where closing the arm bottom portions toward each other and onto the cylindrical portion is a natural physical consequence of pushing the traveling component against the arm top portions.

Subsequent process step 614 can involve allowing the pivotable medical device clamp to pivot around but not slide laterally along the cylindrical portion of the separate object while the nonlinear regions are clamped onto the cylindrical portion. Such a function can be a feature of the pivotable clamp being fully clamped onto the cylindrical portion of the separate object. Step 614 can be manually or automatically performed, such as where the pivotable but non-slidable ability of the pivotable device clamp is a natural physical consequence of closing the arm bottom portions together and clamping them onto the cylindrical portion of the separate object. This can be facilitated by one or more features on the nonlinear regions of the arm bottom portions that prevent or limit lateral sliding of the cylindrical portion along the arm bottom portions.

At the next process step 616, the rotatable fiducial marker array can be rotated with respect to the pivotable medical device clamp while rotatably coupled to the clamp. This can be done, for example, while the rotational coupling is sufficiently loose enough such that the mating faces of a clamp coupling component and array coupling component are spaced apart and any protruding ridges, divots, and/or other locking features of crown attachments on one or both mating faces are able to rotate past each other. Step 616 can be manually or automatically performed, such as where a separate robotic system can be configured to handle the rotatable fiducial marker array so as to rotate the fiducial marker array to a desired rotational position.

At following process step 618, the rotatable fiducial marker array can be locked in place at a set rotational position or orientation with respect to the pivotable medical device clamp. This can involve a set rotational position where mating crown attachments have ridges and divots that align with each other, whereupon the thumbscrew or other coupling device on the fiducial marker array can then be further tightened such that no further rotation of the fiducial marker array can occur. Step 618 can be manually or automatically performed, such as where a separate robotic system can be configured to handle to further rotate the array thumbscrew into the threaded opening of the clamp coupling component, as well as the natural physical consequence of mating crown attachment features physically preventing any further rotation.

At the next process step 620, the positions of fiducial markers located on the rotatable fiducial maker array can be calibrated relative to the clamped separate object. In particular, these fiducial marker positions can be calibrated relative to an end tip and a longitudinal axis of the cylindrical portion of the separate object. Step 620 can be manually or automatically performed, such as where a separate augmented reality system having cameras, detectors, software, and the like can be configured to detect and locate the relative positions of the fiducial markers once the fiducial marker array is locked in place relative to the separate object, as will be readily understood by those of skill in the art. The method can then end at end step 622.

For foregoing method 600, it will be appreciated that not all process steps are necessary, and that other process steps may be added in some arrangements. For example, forcing the traveling component up the shaft, opening the arm arrangement bottom portions, and removing the cylindrical object might be added steps. Further methods can include, for example, reconfiguring the pivotable clamp, such as by replacing arm arrangements with larger or smaller arm arrangements. Furthermore, the order of steps may be altered in some cases, and some steps may be performed simultaneously. For example, step 604 may be performed later in the process in some cases. As another example, steps 610 and 612 can be performed simultaneously. Although known process steps are provided for the various techniques in detailed method 600, it will be appreciated that any other suitable similar method for using a pivotable medical device clamp can also be used. Other variations and extrapolations of the disclosed methods will also be readily appreciated by those of skill in the art.

Rotatable Fiducial Marker Array

Figure 7:
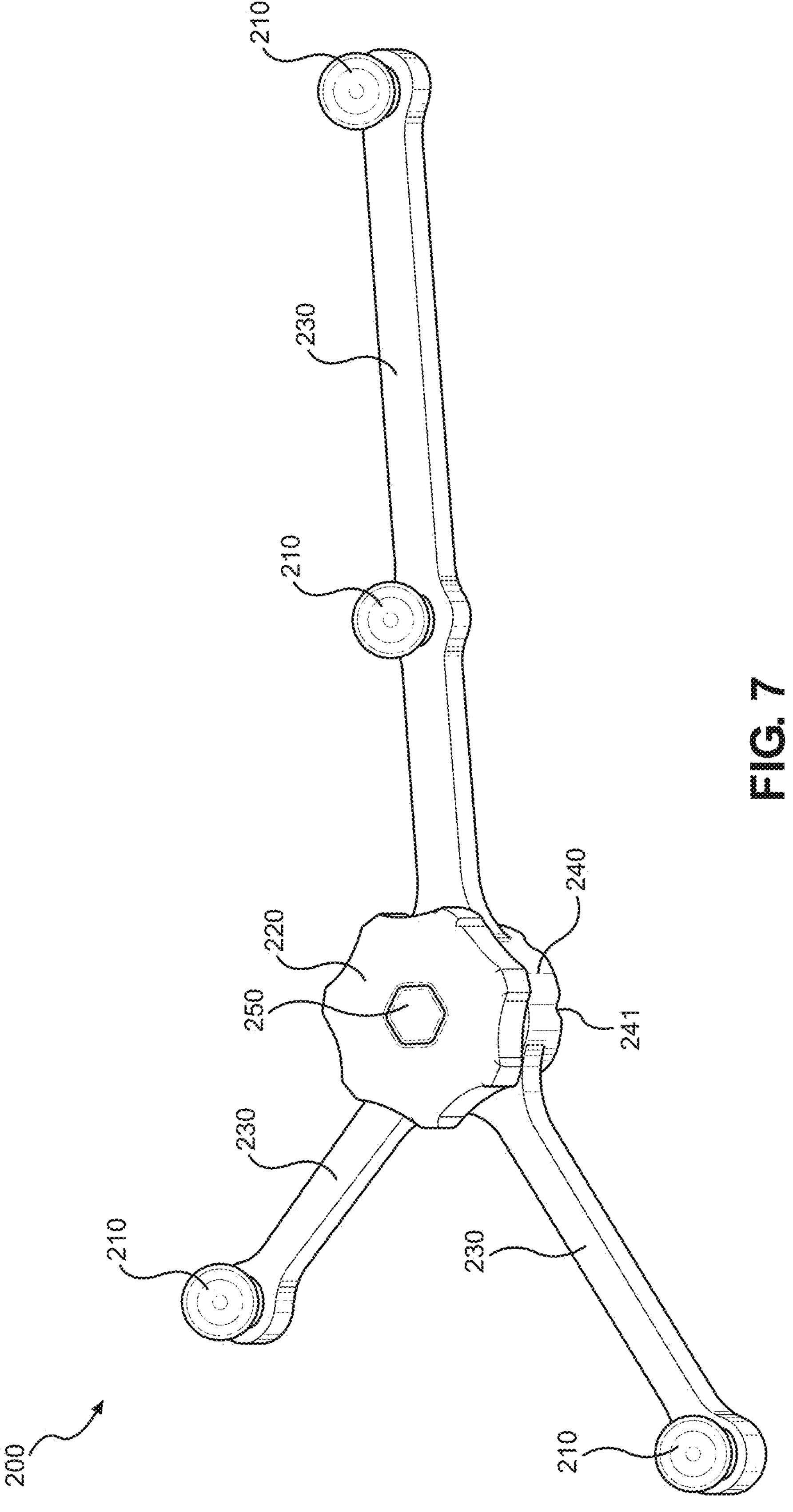
FIG. 7 illustrates in top perspective view an example rotatable fiducial marker array according to one embodiment of the present disclosure.

Transitioning now to FIG. 7, an example rotatable fiducial marker array is illustrated in top perspective view. As noted above, rotatable fiducial marker array 200 can generally include multiple fiducial markers 210 removably mounted using marker posts (not shown) along multiple array arms 230 that extend in multiple directions from array central region 240. Rotatable fiducial marker array 200 can be configured to be rotatably coupled to a separate object, such as a pivotable clamp as detailed above, by way of an array coupling arrangement that can include array thumbwheel 220 coupled to array shaft 250 having a threaded portion and array locking features 241 located along a bottom surface of array central region 240, as discussed in greater detail below.

In various embodiments, rotatable fiducial marker array 200 can be readily removed from and installed onto the separate object and can be configured for use with multiple different and disparate separate objects. Although rotatable fiducial marker array 200 resembles a fiducial marker localizer in some regards, it will be readily appreciated that this fiducial marker array does not have a typical localizer pointer tip, but rather can be rotatably adjusted and locked in place with respect to the separate object prior to a fiducial marker location calibration procedure. In some arrangements, rotatable fiducial marker array 200 can come in a variety of sizes and shapes, such that different fiducial marker arrays can be sized and arranged for use with different specific separate medical probes, tools, or other objects.

Figures 8A, 8B:
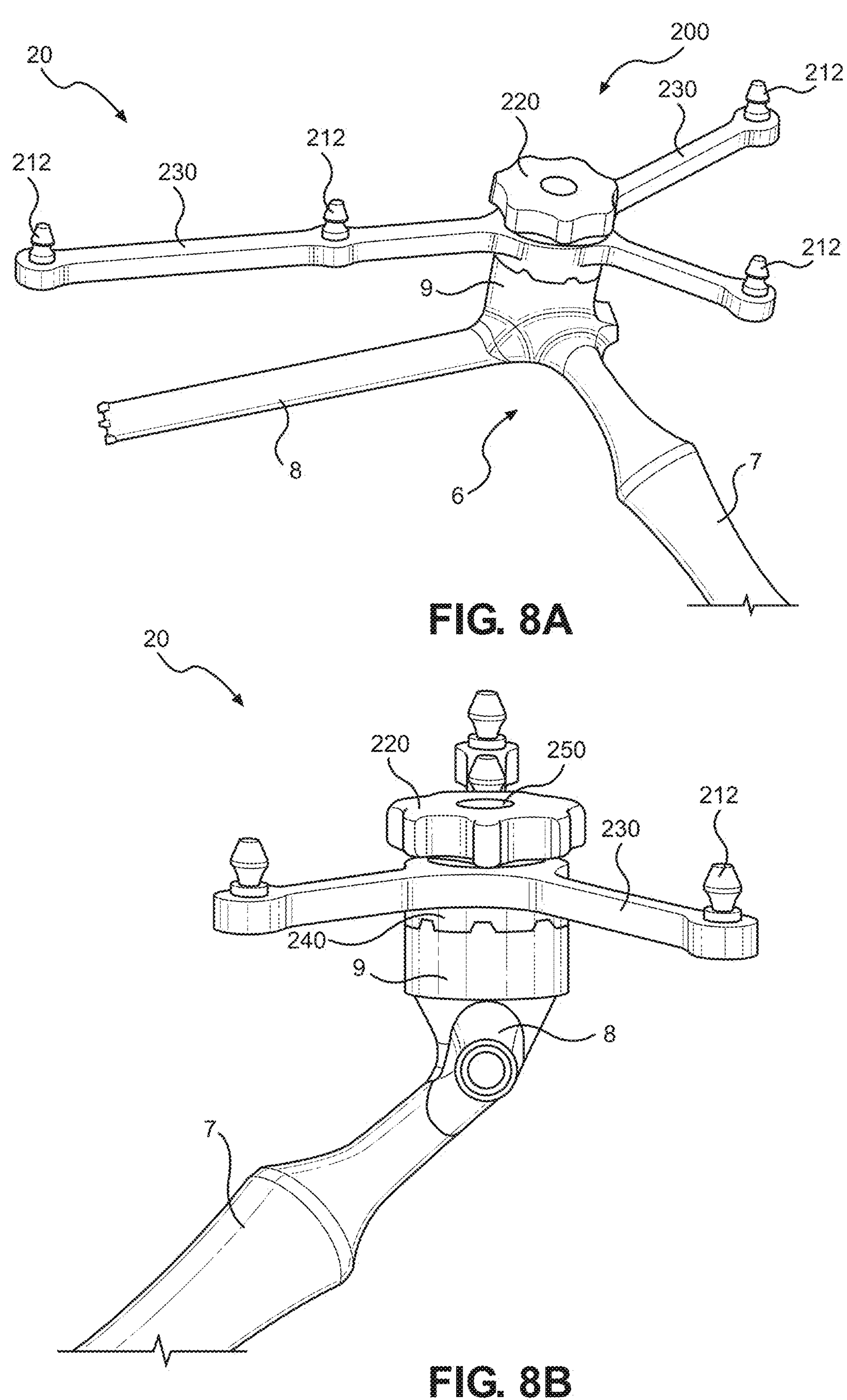
FIG. 8A illustrates in top perspective view an example alternative medical fiducial marker system with the rotatable fiducial marker array of FIG. 7 coupled to a separate surgical drill sheath according to one embodiment of the present disclosure.
FIG. 8B illustrates in rear elevation view the alternative medical fiducial marker system of FIG. 8A according to one embodiment of the present disclosure.

FIGS. 8A and 8B illustrate an example alternative medical fiducial marker system with the rotatable fiducial marker array of FIG. 7 coupled to a separate surgical drill sheath in top perspective and rear elevation views respectively. While rotatable fiducial marker array 200 can be designed and configured to operate with respect to a pivotable medical device clamp such as that which is illustrated and described above, it will be understood that the disclosed rotatable fiducial marker array can also be configured for use with other medical devices and tools. For example, alternative medical fiducial marker system 20 can include rotatable fiducial marker array 200 rotatably coupled to separate surgical drill sheath 6. Rotatable fiducial marker array 200 can be identical or substantially similar to that which is shown and described above, and as such can include thumbwheel 220, array arms 230, array central region 240, array shaft 250, and marker posts 212 configured for the removable mounting of fiducial markers (not shown).

Surgical drill sheath 6 can generally include handle 7, hollow cylindrical sheath 8, and crown coupling component 9 that can be attached atop or integrally formed with the hollow cylindrical sheath. Crown coupling component 9 can be similar to clamp coupling component 170 above in that it can have a central threaded opening and crown attachment with mating features configured to rotatably couple and lock in place with rotatable fiducial marker array 200. As in the foregoing medical fiducial marker system 20 above, rotatable fiducial marker array 200 can be removably coupled from crown coupling component 9, such as by rotating thumbwheel 220 to completely remove a bottom threaded portion of array shaft 250 from a central threaded opening of crown coupling component 9. It will be understood that separate surgical drill sheath 6 can be replaced by any number of different medical devices, tools, or other separate objects having a coupling arrangement similar to crown coupling component 9 or clamp coupling component 170 above.

Figure 9A:
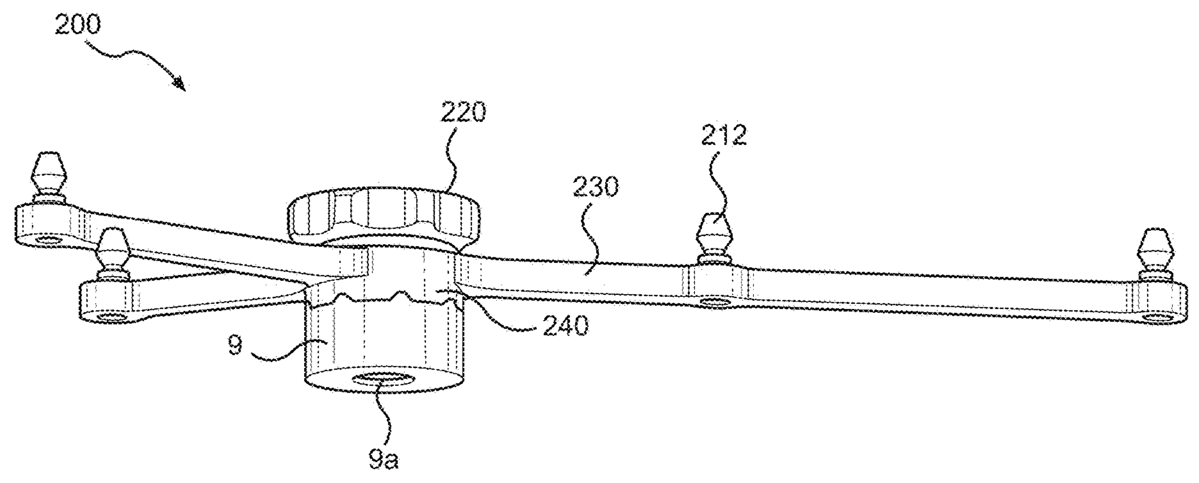
FIG. 9A illustrates in side perspective view the rotatable fiducial marker array of FIG. 7 as being interfaced with a separate crown coupling component according to one embodiment of the present disclosure.

Continuing with FIG. 9A the rotatable fiducial marker array of FIG. 7 is illustrated in side perspective view as being interfaced with a separate crown coupling component. In some arrangements, crown coupling component 9 itself can be removably coupled to and from a surgical drill sheath other separate medical device or object. In such arrangements, central threaded opening 9*a* can extend all the way through crown coupling component 9 so that this threaded opening can also be used for removably coupling a combined unit of rotatable fiducial marker array 200 and crown coupling component 9 to the separate object while the marker array is already rotatably coupled to the crown coupling component.

Figure 9B:
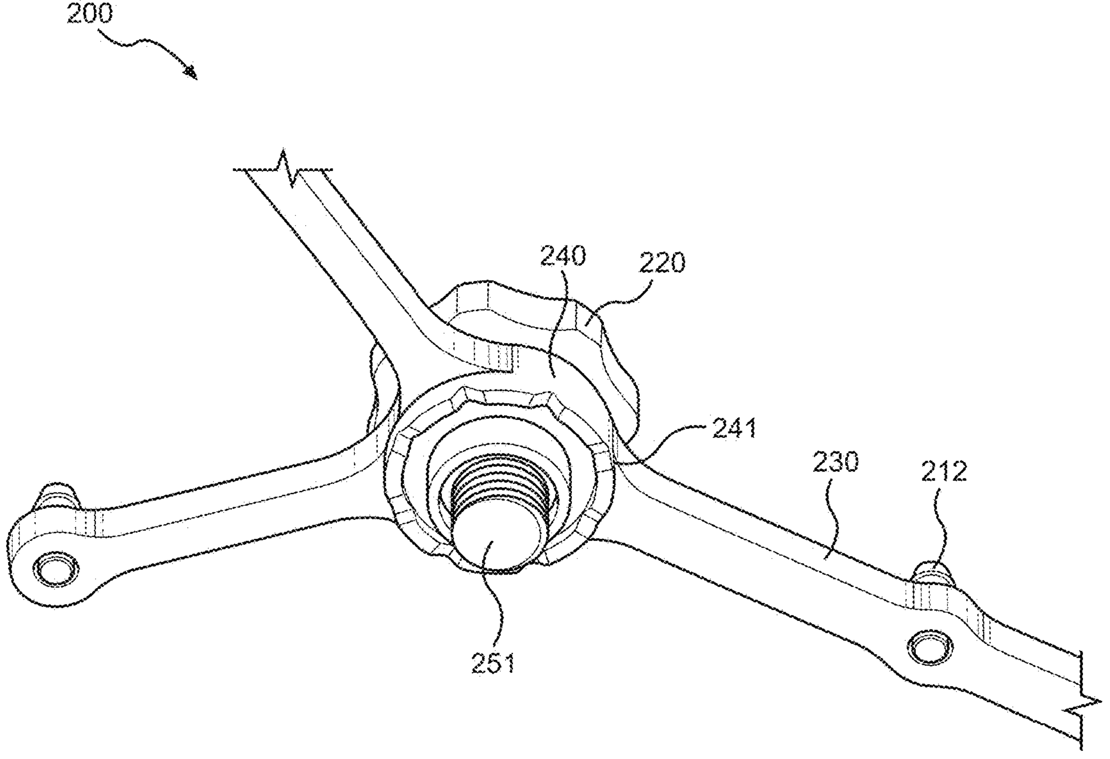
FIG. 9B illustrates in bottom perspective view the rotatable fiducial marker array of FIG. 7 according to one embodiment of the present disclosure.

FIG. 9B illustrates in bottom perspective view the rotatable fiducial marker array of FIG. 7 as being removed from any coupling component such as crown coupling component 9 or clamp coupling component 170. As noted above, rotatable fiducial marker array 200 can include thumbwheel 220 or other rotatable item coupled to an array shaft having a bottom threaded portion 251 that is configured to be inserted into a threaded opening within a clamp coupling component or crown coupling component of a separate medical device or object. Array locking features 241 can be located along a bottom surface of array central region 240, and these locking features can be sized and shaped to mate with ridges or other locking features on the separate object, such as the crown attachment on clamp coupling component 170 above.

Again, a loose coupling with bottom threaded portion into the threaded opening can allow array arms 230, marker posts 212 with coupled fiducial markers (not shown), and array central region 240 to rotate together around the shaft with bottom threaded portion 251. When a desired rotational orientation is achieved, then thumbwheel 220 or other rotational item can be rotated to engage bottom threaded portion 251 further into the threaded opening within a clamp coupling component or crown coupling component. This can then close together locking features 241 onto mating ridges or other locking features of the separate crown arrangement so that rotatable fiducial marker array 200 is rotationally locked in place.

Figure 10:
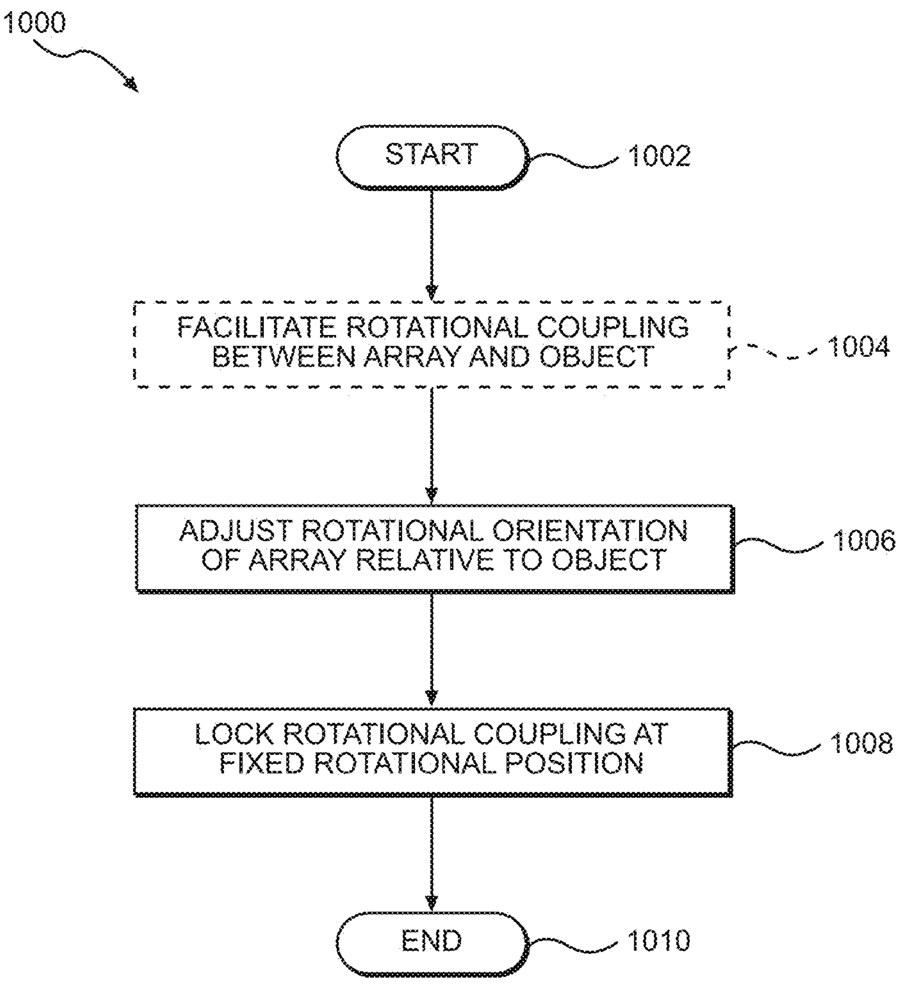
FIG. 10 illustrates a flowchart of an example summary method of using a rotatable fiducial marker array according to one embodiment of the present disclosure.

Moving next to FIG. 10, a flowchart of an example summary method of using a rotatable fiducial marker array is provided. Summary method 1000 can represent one broad aspect for overall methods of use for a rotatable fiducial marker array, and it will be understood that various other steps, features, and details of such a broad aspect and overall methods of use are not provided here for purposes of simplicity. While the rotatable fiducial marker array can be designed for use with a pivotable medical device clamp as disclosed herein, it is contemplated that the disclosed rotatable fiducial marker array can also be used with other medical devices, tool, and objects, and also in other environments and applications.

After a start step 1002, a first optional process step 1004 can involve facilitating a rotational coupling between a rotatable fiducial marker array and a separate object, such as a pivotable clamp, for example. As noted above, the rotatable fiducial marker array can include a rigid body having a central region and multiple array arms extending therefrom and configured to support a plurality of fiducial markers at fixed locations relative to each other to form an asymmetrical fixed positional arrangement of fiducial markers. Step 1004 can be optional in some situations, such as where the rotatable fiducial marker array is already rotationally coupled to the separate object. Step 1004 can be performed manually or automatically in some cases, such as where a separate robotic system can be configured to handle and rotationally couple the fiducial marker array to the separate object.

At the following process step 1006, a rotational orientation of the fiducial marker array can be adjusted from a first rotational position to a second rotational position. This can involve rotating the rotatable fiducial marker array body about an axis extending through its central shaft such that its arms and fiducial markers rotate together to a different rotational position relative to the separate object to which it is rotationally coupled. Step 1006 can be manually or automatically performed, such as where a separate robotic system can be configured to handle and rotate the fiducial marker array.

At subsequent process step 1008, the rotational coupling can be locked at a fixed rotational position between the rotatable fiducial marker array and the separate object, such that the locked rotational coupling prevents rotational movement of the rotatable fiducial marker array relative to the separate object. This can involve the use of locking features on one or both of the coupling components of the fiducial marker array and the separate object, and these can be crown attachments as detailed above, for example. Locking the fiducial marker array in place rotationally can involve twisting or rotating a thumbwheel or other screw device such that a threaded portion of the fiducial marker array shaft is rotated deeper into a threaded opening of the separate object, for example. Step 1008 can be manually or automatically performed, such as where a separate robotic system can be configured to further rotate a thumbwheel or thumbscrew of the rotatable fiducial marker array. The method can then end at end step 1010.

Figure 11A:
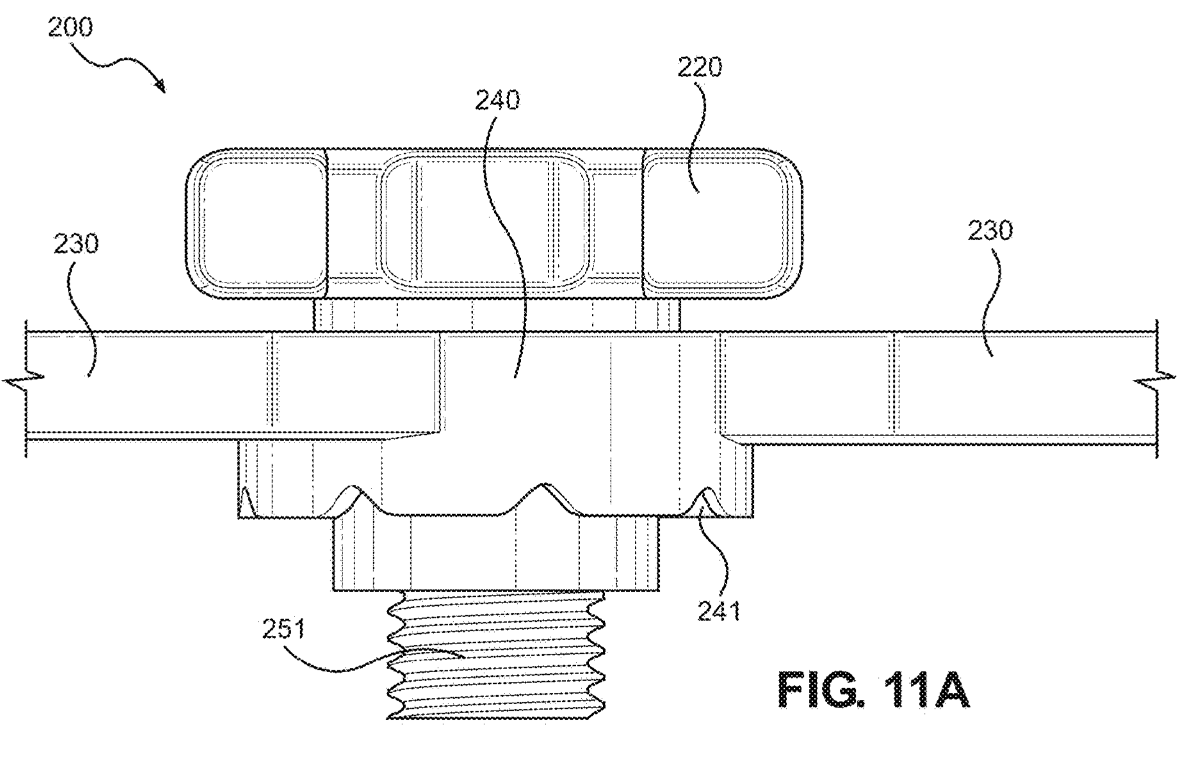
FIG. 11A illustrates in side elevation view an array coupling arrangement of the rotatable fiducial marker array of FIG. 7 according to one embodiment of the present disclosure.
Figure 11B:
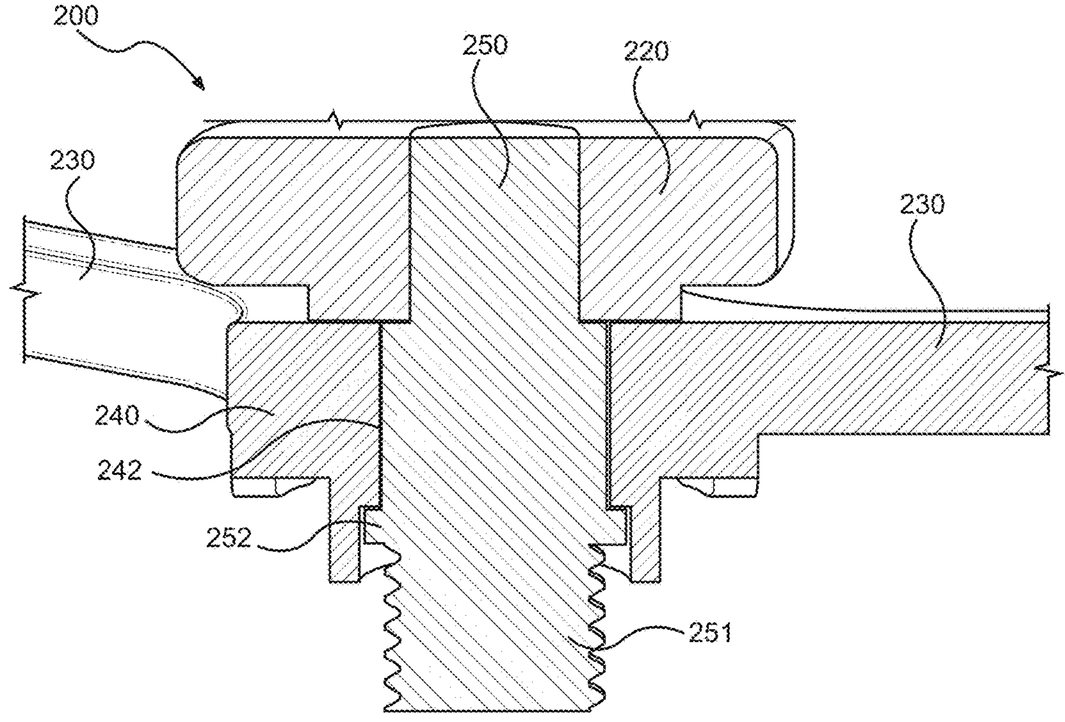
FIG. 11B illustrates in side cross-section view the array coupling arrangement of FIG. 11A according to one embodiment of the present disclosure.

Continuing with FIGS. 11A and 11B, an array coupling arrangement of the rotatable fiducial marker array of FIG. 7 is illustrated in side elevation and side cross-section views respectively. Again, an array coupling arrangement of rotatable fiducial marker array 200 can be coupled to the rigid body of the array at its central region 240 and can be configured to couple the rigid body at its central region to a separate object such that the rigid body is rotatable relative to the separate object about a rotational axis extending through the central region. The array coupling arrangement can be further configured to facilitate locking the rigid body in place at one or more fixed rotational positions relative to the separate object. This array coupling arrangement can include a shaft 250 having a threaded portion 251, with the shaft being extendable through an opening 242 in the rigid body central region 240 and configured such that its threaded portion mates within a threaded opening at the separate object. The rigid body can be configured to rotate about shaft 250 when the shaft is extended through the rigid body central region opening and is mated within the threaded opening of the separate object.

This array coupling arrangement can further include thumbwheel 220 coupled to shaft 250 at an end opposite the threaded portion 251, with the thumbwheel being configured to rotate the shaft to couple and uncouple the shaft from the threaded opening of the separate object. Thumbwheel 240 can be press fit or otherwise attached or coupled onto shaft 250. The array coupling arrangement can also include one or more array locking features 241 along a bottom surface of the rigid body at its central region 240. These array locking features 241 can be configured to interact with one or more separate locking features on the separate object to facilitate locking the rigid body in place at a fixed rotational position relative to the separate object. As shown, array locking features 241 can be divots or depressions in a crown attachment that are configured to receive ridges 174 in a mating crown attachment of the separate object.

In some arrangements, shaft 250 can also include extension ring 252 or another enlarged portion integrally formed with the shaft or coupled thereto. Shaft 250 can be arranged such that this extension ring 252 cannot pass through opening 242 in the rigid body central region 240, as shown in FIG. 11B. This can result in shaft 250 being held captive within opening 242 at the rigid body central region 240. This arrangement can allow shaft 250 to rotate freely with respect to the marker array main body without allowing the shaft to fall out of or be readily removed therefrom.

Figure 12:
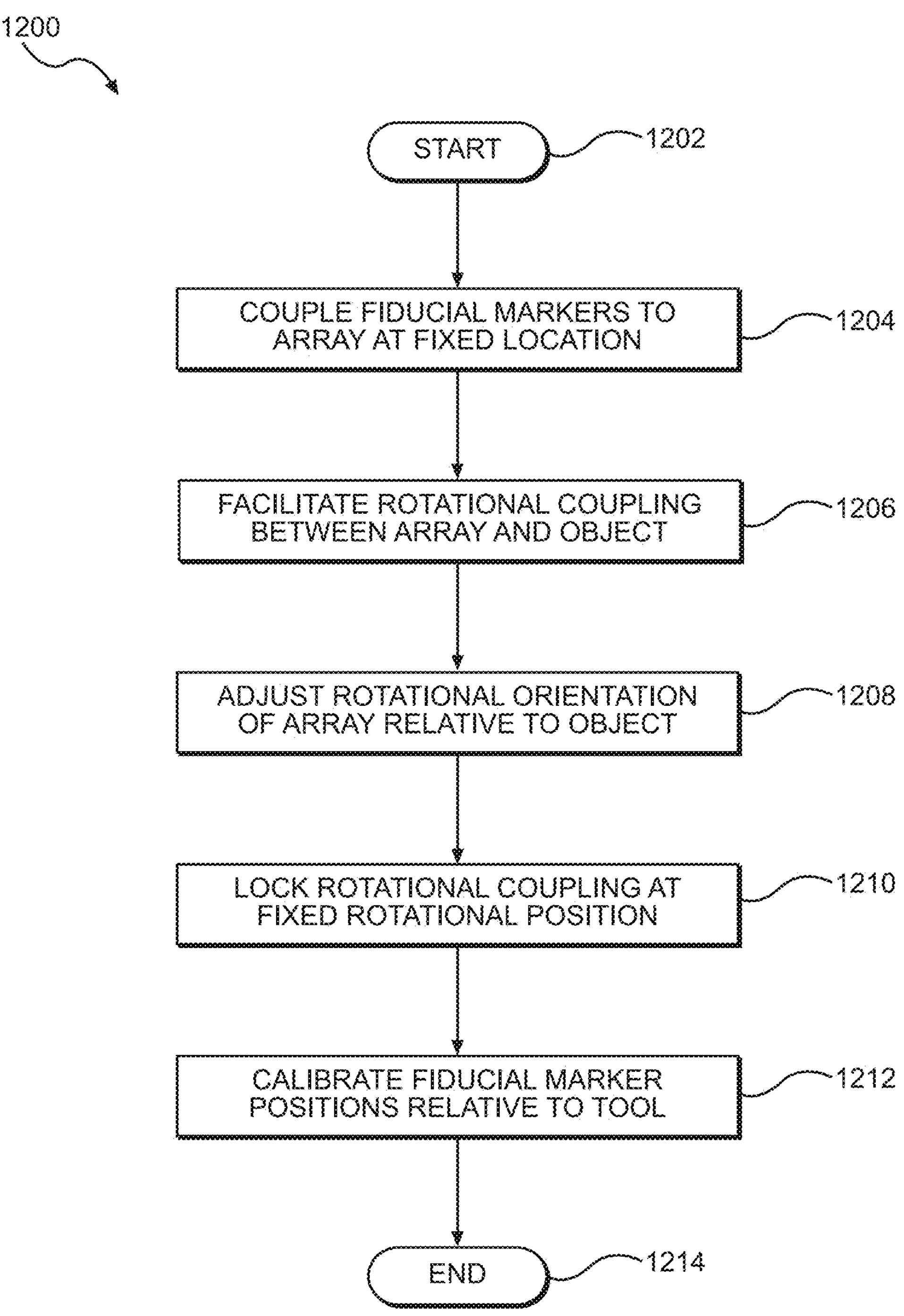
FIG. 12 illustrates a flowchart of an example detailed method of using a rotatable fiducial marker array according to one embodiment of the present disclosure.

Next, FIG. 12 illustrates a flowchart of an example detailed method of using a rotatable fiducial marker array. Detailed method 1200 can represent one possible detailed way of using a rotatable fiducial marker array, and it will be understood that various other steps, features, and details of such a detailed method are not provided here for purposes of simplicity. Detailed method 1200 can also include some or all steps and details of summary method 1000 above, as will be readily appreciated. After a start step 1202, a first process step 1204 can involve coupling fiducial markers to the rotatable fiducial marker array at fixed locations. This can involve the use of removable and replaceable fiducial markers, which can be mounted onto marker posts along arms of the fiducial marker array, as will be readily appreciated. Step 1204 can be manually or automatically performed, such as where a robotic system can be configured to remove and/or install fiducial markers onto marker posts along a fiducial marker array.

A following process step 1206 can involve facilitating a rotational coupling between a rotatable fiducial marker array and a separate object, such as a pivotable clamp, for example. This step can be identical or similar to step 1004 above and can also involve a rotatable fiducial marker array as illustrated and described above. Step 1206 can be performed manually or automatically in some cases, such as where a separate robotic system can be configured to handle and rotationally couple the fiducial marker array to the separate object.

At subsequent process step 1208, a rotational orientation of the fiducial marker array can be adjusted relative to the separate object. This can involve rotating the rotatable fiducial marker array body about an axis extending through its central shaft such that its arms and fiducial markers rotate together to a different rotational position relative to the separate object to which it is rotationally coupled. Step 1208 can be manually or automatically performed, such as where a separate robotic system can be configured to handle and rotate the fiducial marker array.

The next process step 1210 can involve locking the rotational coupling at a fixed rotational position between the rotatable fiducial marker array and the separate object such that the locked rotational coupling prevents rotational movement of the rotatable fiducial marker array relative to the separate object. This can involve the use of locking features on one or both of the coupling components of the fiducial marker array and the separate object, and these can be crown attachments as detailed above, for example. Locking the fiducial marker array in place rotationally can involve twisting or rotating a thumbwheel or other screw device such that a threaded portion of the fiducial marker array shaft is rotated deeper into a threaded opening of the separate object, for example. Step 1210 can be manually or automatically performed, such as where a separate robotic system can be configured to further rotate a thumbwheel or thumbscrew of the rotatable fiducial marker array.

A following process step 1212 can involve calibrating fiducial marker positions on the rotatable fiducial marker array relative to both a longitudinal axis of the separate tool cylindrical portion and a tip of the separate tool. This step can be done when the rotational coupling is locked at the fixed rotational position. In the event that the separate object is a pivotable clamp as disclosed herein, this step can also be done when the pivotable clamp is clamped onto the separate tool cylindrical portion. Step 1212 can be manually or automatically performed, such as where a separate augmented reality system having cameras, detectors, software, and the like can be configured to detect and locate the relative positions of the fiducial markers once the fiducial marker array is locked in place relative to the separate object, as will be readily understood by those of skill in the art. The method can then end at end step 1214.

For foregoing method 1200, it will be appreciated that not all process steps are necessary, and that other process steps may be added in some arrangements. For example, the rotatable fiducial marker array can be removed from the separate object after a given procedure involving both devices is finished. Furthermore, the order of steps may be altered in some cases, and some steps may be performed simultaneously. For example, step 1204 may be performed later in the process in some cases. As another example, steps 1206 and 1208 can be performed simultaneously. Although known process steps are provided for the various techniques in detailed method 1200, it will be appreciated that any other suitable similar method for using a rotatable fiducial marker array can also be used. Other variations and extrapolations of the disclosed methods will also be readily appreciated by those of skill in the art.

Alternative Clamp and Array Embodiments

Figure 13A:
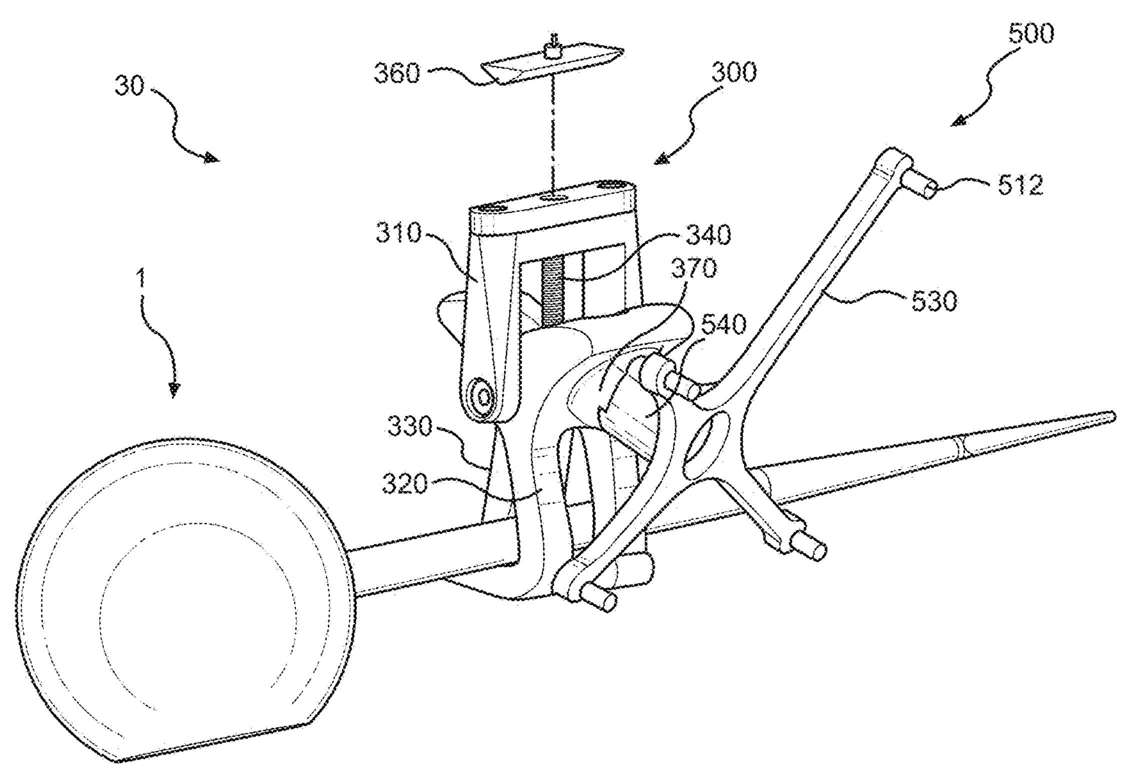
FIG. 13A illustrates in front perspective view an example alternative medical fiducial marker system having an alternative rotatable fiducial marker array and an alternative pivotable medical device clamp as being clamped to a separate medical device according to one embodiment of the present disclosure.
Figure 13B:
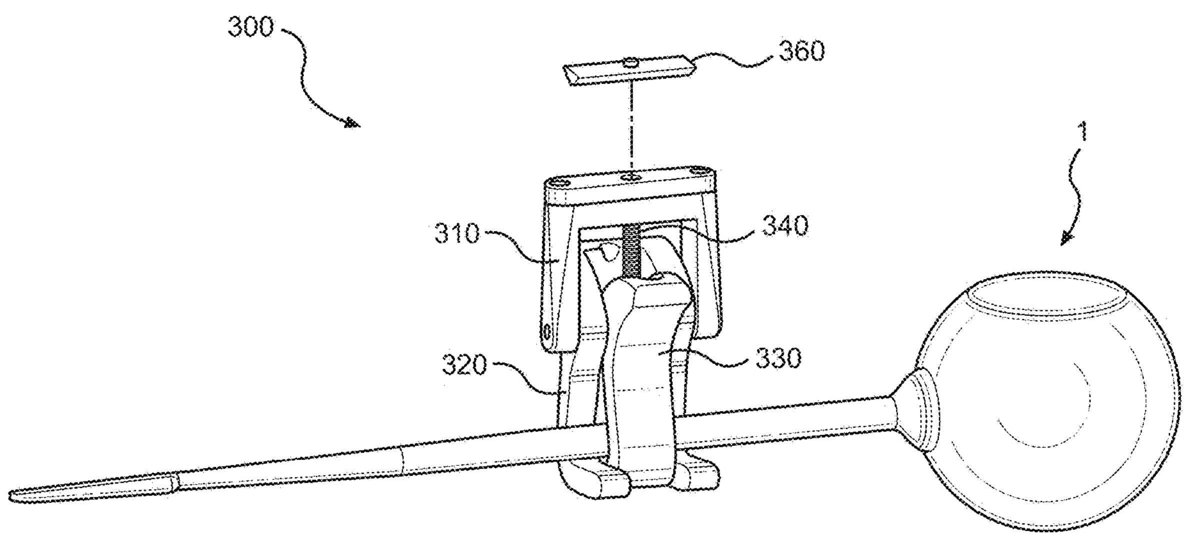
FIG. 13B illustrates in rear perspective view the alternative pivotable medical device clamp of FIG. 13A as being clamped to a separate medical device according to one embodiment of the present disclosure.

Moving next to FIGS. 13A through 14D, alternative pivotable clamp and rotatable fiducial marker array embodiments will now be provided. FIG. 13A depicts an example alternative medical fiducial marker system having an alternative rotatable fiducial marker array and an alternative pivotable medical device clamp as being clamped to a separate medical device is shown in front perspective view. FIG. 13B shows the same system without the rotatable fiducial marker array in rear perspective view. As in the foregoing system embodiments 10 and 20 above, alternative medical fiducial marker system 30 can be configured to fix multiple fiducial markers at set locations in three-dimensional space with respect to a separate object such as separate medical device 1, which again can be a pedicle probe, for example. Alternative medical fiducial marker system 30 can generally include an alternative pivotable medical device clamp 300 and an alternative rotatable fiducial marker array 500.

Similar to foregoing embodiments, alternative pivotable medical device clamp 300 can include at least main body 310, first arm arrangement 320, second arm arrangement 330, shaft 340, traveling component (not shown), twisting component 360, and clamp coupling component 370, among various other components and features. Alternative pivotable medical device clamp 300 can generally be designed and configured to perform the same or similar functions as pivotable medical device clamp 100 above regarding clamping onto a cylindrical portion of an object in a pivotable but non-slidable manner, as well as providing a coupling component for an associated rotatable fiducial marker array. As such, many components, features, and functions of alternative pivotable medical device clamp 300 can be identical or substantially similar to those of pivotable medical device clamp 100 above, with notable differences and variations being discussed in detail with respect to FIGS. 14A-14D below.

Also similar to foregoing embodiments, alternative rotatable fiducial marker array 500 can include multiple array arms 530 extending in multiple directions from array central region 540, multiple marker posts 512 configured to couple a plurality of removable fiducial markers (not shown), and an array coupling arrangement that can include an array thumbwheel (not shown) coupled to an array shaft (not shown) having a threaded portion and array locking features (not shown) located along a bottom surface of the array central region 540. Alternative rotatable fiducial marker array 500 can generally be designed and configured to perform the same or similar functions as rotatable fiducial marker array 200 above regarding having multiple fiducial markers at fixed locations in space relative to each other, being configurable for use with multiple different and disparate separate objects (e.g., pivotable clamp, surgical drill sheath, etc.), being rotatable with respect to an associated separate object, and being readily removable from and installable onto the associated separate object.

In some embodiments, alternative rotatable fiducial marker array 500 can include an array coupling arrangement that is identical or similar enough to the array coupling arrangement of rotatable fiducial marker array 200 above such that these arrays can be interchangeable with each other with respect to being coupled to the same pivotable clamps or other separate objects. Unlike the foregoing embodiments, alternative rotatable fiducial marker array 500 can have four array arms 530 rather than three arms and can have an alternative shape, as shown. It will be readily appreciated that rotatable fiducial marker array 500 can alternatively have more or fewer array arms, more or fewer marker posts, and various alternative shapes, sizes, and marker post locations, as may be desired for various parameters involving varying fiducial marker array uses.

Next, FIGS. 14A-14D illustrate an example alternative pivotable medical device clamp in front perspective, side perspective, and side cross-section views respectively. It will be understood that alternative pivotable medical device clamp 300 can be similar in many regards to pivotable medical device clamp 100 above, such that many similar details need not be repeated. For example, first arm arrangement 320 can have multiple bottom portions while second arm arrangement 330 has a single bottom portion, and both arm arrangements can be configured to rotate about pin 314 that extends through main body 310. Unlike clamp 100 above, alternative pivotable medical device clamp can include differently shaped arm arrangements 320, 330 and a different clamp coupling component 370 with alternative features.

As shown, the bottom portions of first and second arm arrangements 320, 330 do not have the same curved nature of the foregoing arm bottom portions, although these arm bottom portions are still nonlinear in nature. These arm bottom portions can be configured in the extended and nonlinear arrangements shown to accommodate a wider range of cylindrical sizes and can also include additional laterally extended surface areas to prevent or limit lateral sliding of cylindrical objects along the arm bottom portion surfaces.

Figures 14A, 14B:
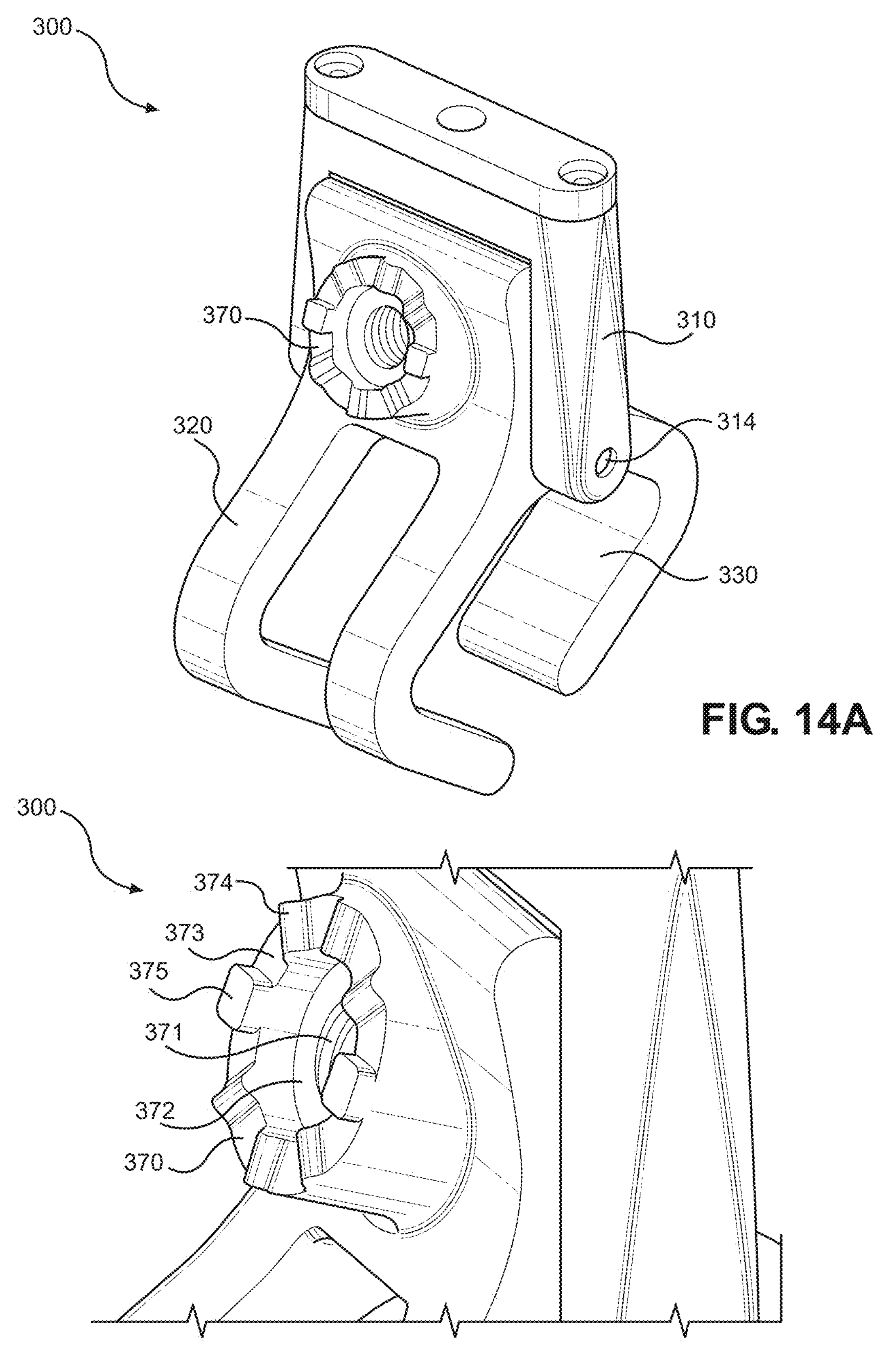
FIG. 14A illustrates in front perspective view the alternative pivotable medical device clamp of FIG. 13A according to one embodiment of the present disclosure.
FIG. 14B illustrates in side perspective view an example clamp coupling component for the alternative pivotable medical device clamp of FIG. 14A according to one embodiment of the present disclosure.

Referencing FIG. 14B, alternative clamp coupling component 370 can be similar to clamp coupling component 170 above in that it can similarly include or involve a threaded central opening 371, larger center opening 372, mating face 373, and ridges 374 extending therefrom. Alternative clamp coupling component 370 can similarly include a crown attachment having the larger center opening 372, mating face 373, and ridges 374, with threaded central opening 371 extending into an arm arrangement on the overall clamp. In addition, alternative clamp coupling component can include raised pegs 375 that facilitate exact rotational positions when mated with another accommodating coupling component. In some arrangements, two raised pegs 375 can be opposite each other on the crown arrangement mating face 373, such that only two rotational positions of a separate mating crown arrangement are possible. These can be forward and backward rotational positions for the separate mating device or object, for example. Other crown arrangements and mating features are also possible to support any number of discrete rotational positions of the separate object, as will be readily appreciated.

Figure 14C:
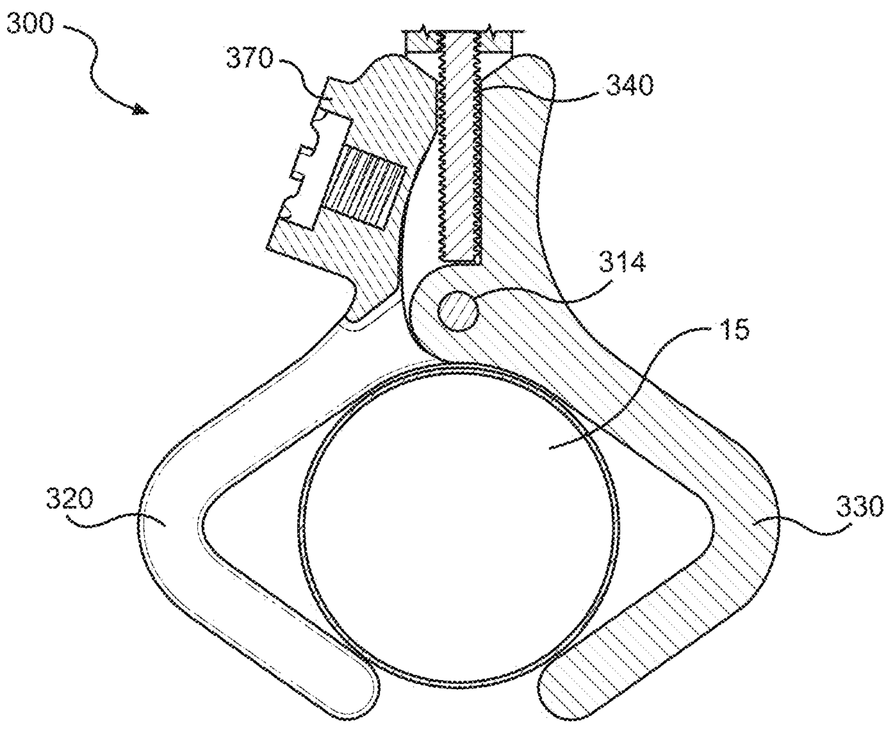
FIG. 14C illustrates in side cross-section view the alternative pivotable medical device clamp of FIG. 14A as being clamped to a separate object having a cylindrical portion with a large cross sectional diameter according to one embodiment of the present disclosure.
Figure 14D:
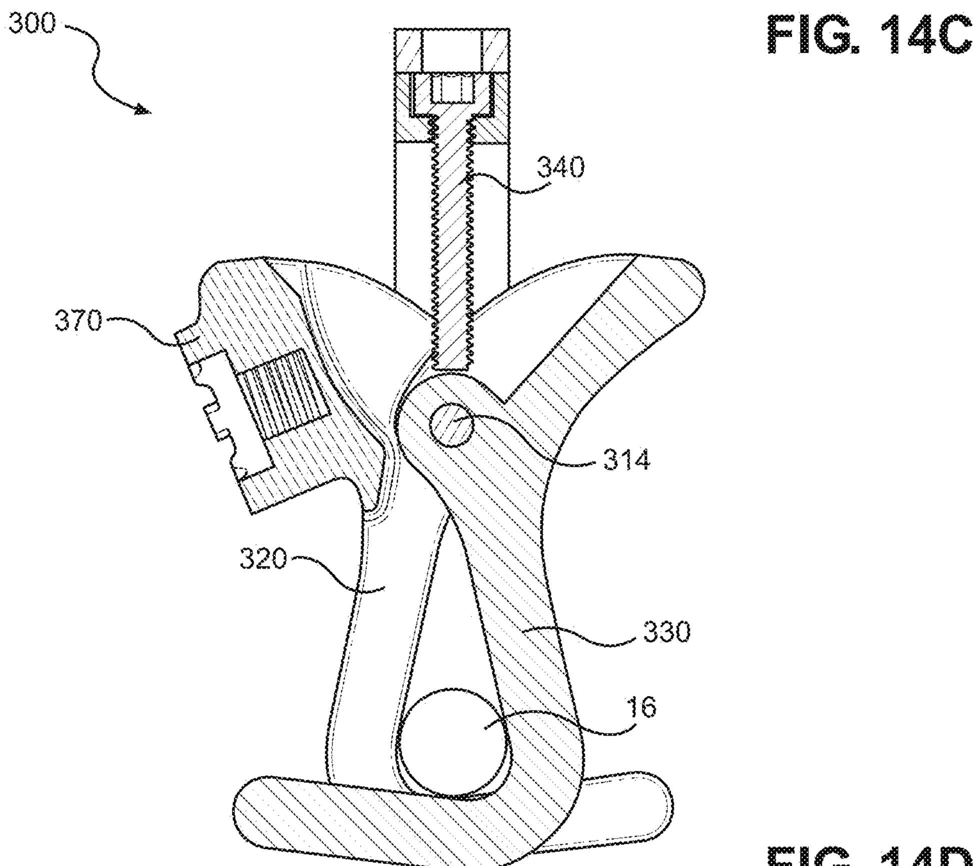
FIG. 14D illustrates in side cross-section view the alternative pivotable medical device clamp of FIG. 14A as being clamped to a separate object having a cylindrical portion with a small cross sectional diameter according to one embodiment of the present disclosure.

FIG. 14C illustrates alternative pivotable medical device clamp 300 as being clamped to a separate object 15 having a cylindrical portion with a large cross sectional diameter, while FIG. 14D illustrates the alternative pivotable medical device clamp as being clamped to a separate object 16 having a cylindrical portion with a small cross sectional diameter. As shown in these figures, first and second arm arrangements 320, 330 can be specifically sized and shaped so as to facilitate clamping onto a wider range of cylindrical diameters. As in the foregoing embodiments, arm arrangements 320, 330 can be pushed on simultaneously and evenly so that they rotate symmetrically about pin 314. This can serve to keep the cylindrical portions of the separate objects being clamped centered between arm arrangements 320, 330 such that the longitudinal axis of any cylindrical portion remains directly beneath pin 314. This can also cause the axis of a given cylindrical portion to rise or fall along a vertical line extending downward from pin 314 such that the exact distance away from the pin can vary depending upon the exact diameter of the cylindrical portion, as shown in FIGS. 14C and 14D. This distance can be accounted for, however, by calibrating the positions of the fiducial markers on a coupled fiducial marker array after clamping and rotational orientation locking has occurred, as noted above.

Medical Device Chuck with Rotating Fiducial Marker Array

Figures 15A, 15B:
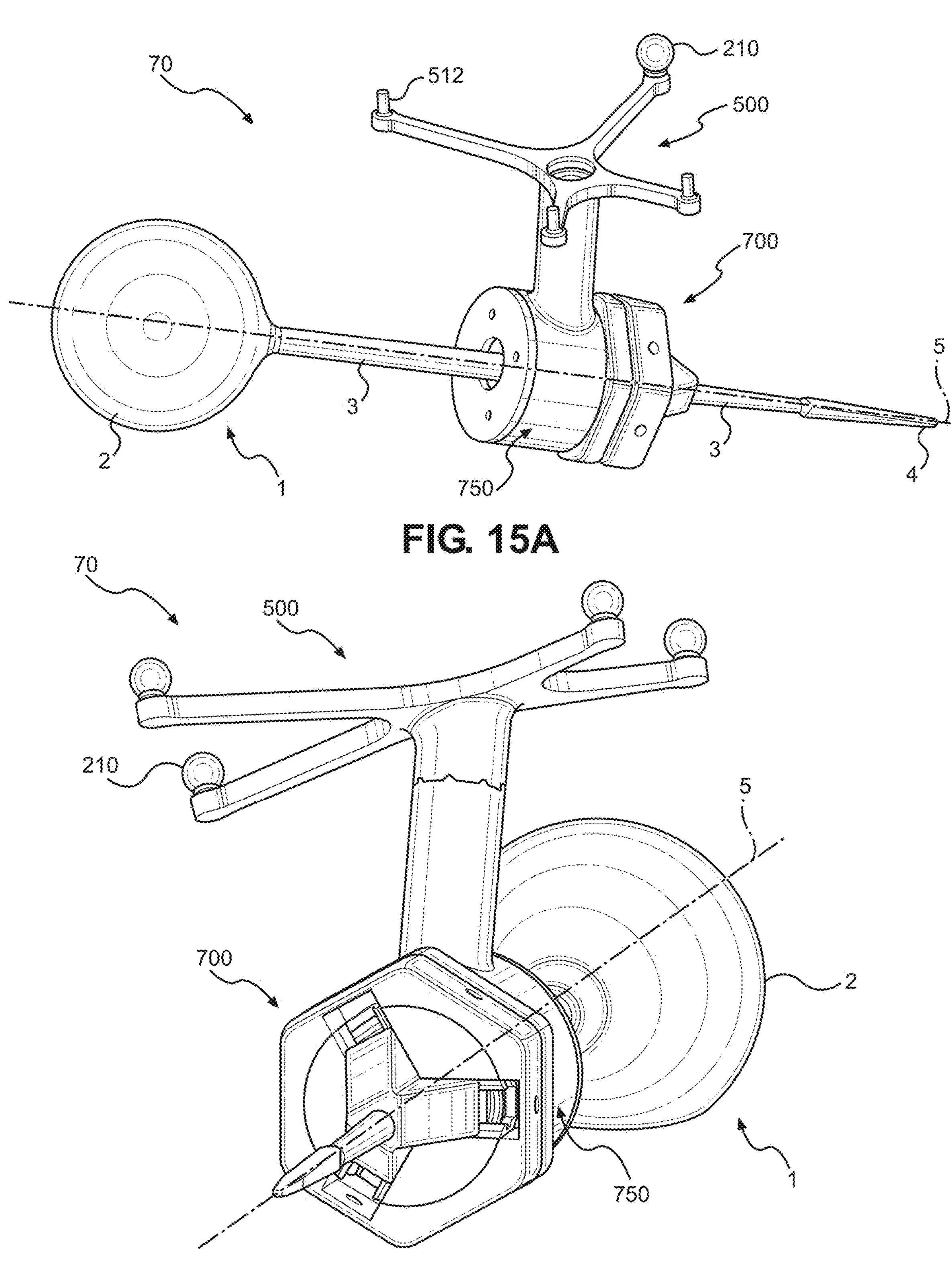
FIG. 15A illustrates in side perspective view an example alternative medical fiducial marker system having a rotating fiducial marker array and a medical device chuck as being clamped to a separate medical device according to one embodiment of the present disclosure.
FIG. 15B illustrates in front end perspective view the alternative medical fiducial marker system of FIG. 15A according to one embodiment of the present disclosure.

Transitioning next to FIGS. 15A through 22B, example medical device chucks with rotating fiducial marker arrays will now be illustrated and discussed. FIGS. 15A and 15B depict an example alternative medical fiducial marker system having a rotating fiducial marker array and a medical device chuck as being clamped to a separate medical device in side perspective and front end perspective views respectively. Alternative medical fiducial marker system 70 can generally include a rotatable fiducial marker array 500 that can be removably coupled to a medical device chuck 700, which can be clamped onto a separate medical device 1 by way of a chuck arrangement having jaws or other suitable clamping components. In some arrangements, medical device chuck 700 can be referred to as just a mechanical chuck, such as for applications that do not involve a separate medical device or that are not medical in nature. As in the foregoing embodiments, separate medical device 1 can include a handle 2, shaft or cylindrical portion 3, and endpoint or tip 4, with at least the cylindrical portion defining a longitudinal axis 5 therethrough. While separate medical device 1 can again be a pedicle probe, for example, it will be appreciated that other types of probes, tools, instruments, other medical devices, and other non-medical devices can alternatively be separate objects with which alternative medical fiducial marker system 70 can be used.

Similar to foregoing system embodiments 10, 20, and 30 above, alternative medical fiducial marker system 70 can generally be configured to position multiple fiducial markers 210 at known locations in three-dimensional space relative to a separate object, such as separate medical device 1, so that a surgery, other medical procedure, or other function can be performed while tracking the separate device within an augmented reality environment using the fiducial markers. In some arrangements, fiducial markers 210 can be positioned at known locations relative to longitudinal axis 5 and endpoint or tip 4 of separate medical device 1. Unlike the foregoing pivotable clamp based system embodiments 10 and 30 above, alternative medical fiducial marker system 70 can utilize a medical device chuck 700 configured to clamp onto cylindrical portion 3 such that the clamped cylindrical portion does not slide laterally along and does not pivot or rotate with respect to the jaws or other clamping components of the chuck.

Rather than allowing the jaws or clamping components of medical device chuck 700 to be able to pivot or rotate directly against cylindrical portion 3 while clamped as in the above system embodiments, rotatable fiducial marker array 500 can be arranged such that it can be rotated or pivoted about longitudinal axis 5 by way of being coupled to a rotating sleeve component 750 that is coupled to and rotates around a main body of medical device chuck 700. This alternative arrangement using rotating sleeve component 750 creates a "rotating fiducial marker array" that allows for relative rotation between one combined unit of the rotating sleeve component and rotatable fiducial marker array 500 and another combined unit of cylindrical portion 3 and the jaws and main body of medical device chuck 700, which relative rotation can take place while the chuck jaws are firmly clamped onto the cylindrical portion.

Rotatable fiducial marker array 500 can be rotatably coupled to rotating sleeve component 750 and can be configured to position multiple fiducial markers 210 with respect to separate medical device 1. Although only one fiducial marker 210 is shown in FIG. 15A for purposes of illustration, it will be understood that identical or similar fiducial markers can be removably mounted or otherwise coupled to each of the remaining marker posts 512 on rotatable fiducial marker array 500. Similar to foregoing embodiments, each of multiple fiducial markers 210 can be arranged such that it is located at fixed distances from both tip 4 and longitudinal axis 5 of separate medical device 1. These fixed distances from each fiducial marker 210 to tip 4 and longitudinal axis 5 do not change even as rotatable fiducial marker array 500 and rotating sleeve component 750 rotate together around the main body of medical device chuck 700.

Rotatable fiducial marker array 500 of medical fiducial marker system 70 can be identical or substantially similar to rotatable fiducial marker array 500 disclosed in system 30 of FIG. 13A above. A different rotatable fiducial marker array can alternatively be used with medical fiducial marker system 70, such as rotatable fiducial marker array 200 disclosed in system 10 of FIG. 1A. Various components, details, features, and functions of the rotatable fiducial marker arrays above can identically apply with respect to rotatable fiducial marker array 500 of medical fiducial marker system 70 and need not be repeated. Rather than being rotatably coupled directly to the body of medical device chuck 700, rotatable fiducial marker array 500 can be rotatably coupled to a rotating post of rotating sleeve component 750. As such, rotatable fiducial marker array can be "rotatable" with respect to the rotating post and can rotate or spin about a center region of the array as in foregoing embodiments. In addition to being rotatable about the rotating post, rotatable fiducial marker array 500 can also be a "rotating" fiducial marker array in that the marker array, rotating post, and rotating sleeve component 750 can all be rotating together around the main body of medical device chuck 700.

Figure 15C:
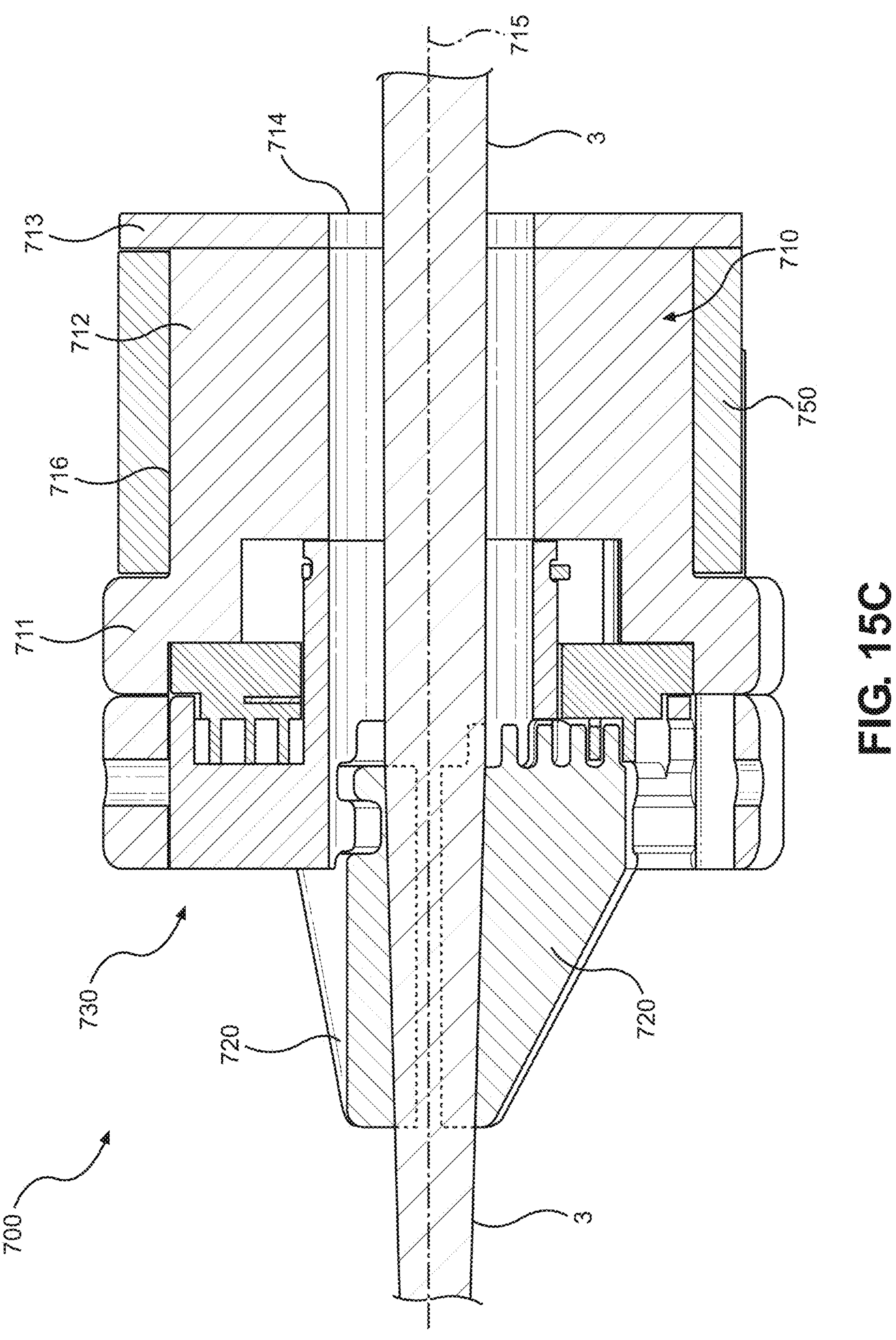
FIG. 15C illustrates in side cross-section view an example medical device chuck of the alternative medical fiducial marker system of FIG. 15A according to one embodiment of the present disclosure.

Continuing with FIG. 15C, an example medical device chuck from the alternative medical fiducial marker system 70 is shown in side cross-section view. While a portion of rotating sleeve component 750 is provided for reference, the rotatable fiducial marker array is not shown here for purposes of simplicity in illustration. Medical device chuck 700 can include at least a main body 710, a plurality of jaws 720, and a chuck adjustment mechanism 730. In some arrangements rotating sleeve component 750 and its various features can be considered as part of medical device chuck 700, while in other arrangements the rotating sleeve component can be a separate component or item from the overall chuck. Rotating sleeve component 750 can be removable with some disassembly of medical device chuck 700 in some arrangements Main body 710 of medical device chuck 700 can include a front region 711, middle region 712, back region 713, and central opening 714. Central opening 714 can extend through the entire main body 710 from front region 711 to back region 713 along main body longitudinal axis 715. In some arrangements, front region 711, middle region 712, and back region 713 of main body 710 can be integrally formed, and in other arrangements these can be separate items that are assembled together to form the main body. For example, back region 713 can be a scroll plate that is fastened to a rear edge of middle region 712.

Middle region 712 of main body 710 can include a captive collar arrangement 716 configured to hold rotating sleeve component 750 at the middle region while allowing the rotating sleeve component to rotate around main body longitudinal axis 715 relative to the main body. Captive collar arrangement 716 can include a cylindrical outer surface around at least a portion of middle region 712 and raised features at the front and back of the middle region outer surface that prevent rotating sleeve component 750 from sliding laterally off the front or back of the middle region outer surface. These raised features can be, for example, one or more portions of front region 711 at the front of middle region 712 and one or more portions of back region 713 at the back of the middle region, such as where the front region and back region have larger diameters than the middle region. In some arrangements, rotating sleeve component 750 can be sufficiently long such that it extends the full length of middle region 712, such that the front and back regions 711, 713 and/or other raised portions prevent the rotating sleeve component from sliding laterally along the middle region outer surface. As shown rotating sleeve component 750 can have an inner diameter that matches the outer diameter of middle region 712 outer surface.

A plurality of jaws 720 can be located at front region 711 of main body 710 and can be configured to clamp onto a cylindrical portion 3 of a separate object that extends through the central opening 714 along the main body longitudinal axis 715 and past both the front region and back region 713 of the main body. Cylindrical portion 3 can define a cylindrical longitudinal axis 5 running therethrough, as noted above. In some arrangements, there can be three jaws 720 that are spaced equal distances apart from each other and that can be configured to move radially inward to clamp onto an object and radially outward to release a clamped object or otherwise increasing the spacing between the jaws. It will be understood that four or more jaws 720 are also possible in some arrangements.

Chuck adjustment mechanism 730 can be coupled to the plurality of jaws 720 and can be configured to adjust the spacing of each of the plurality of jaws relative to the main body longitudinal axis 715. For example, adjusting the spacing of the plurality of jaws 720 can clamp the jaws onto the cylindrical portion 3 of the separate object when the separate object is located or placed between the jaws and the jaws are all moved radially inward. This can result in a firm clamping such that the cylindrical portion 3 is unable to pivot or rotate and is also unable to move laterally relative to the plurality of jaws 720 and the main body 710 of medical device chuck 700. Chuck adjustment mechanism 730 can include various parts and features of a scroll chuck, for example, further details for which are provided below.

In various embodiments, each medical device chuck 700 can be configured for use with different separate objects having a range of sizes. For example, a given medical device chuck 700 can be suitable for use with separate objects with a cylindrical portion having a cross-section diameter of about 1-12 mm. In some arrangements, a more tailored medical device chuck can be suitable for use with cylindrical portions having a diameter of about 1-8 mm, while another tailored medical device chuck can be suitable for use with cylindrical portions having a diameter of about 5-12 mm. Other sizes and ranges are also possible.

As will be readily appreciated, the cylindrical longitudinal axis 5 of cylindrical portion 3 can coincide with the main body longitudinal axis 715 such that these axes are on top of each other when the plurality of jaws 720 are clamped onto the cylindrical portion of the separate object 1. Such an arrangement for medical device chuck 700 can be advantageous over the foregoing clamp based embodiments since the cylindrical longitudinal axis 5 will always be at the same location within the medical device chuck regardless of the size of the separate object and the diameter of its cylindrical portion that is used with the chuck. Conversely, the axis of the cylindrical portion can rise or fall within the clamp arm arrangements depending on the diameter of the cylindrical portion, as noted above with respect to FIGS. 14C-14D.

Figure 16A:
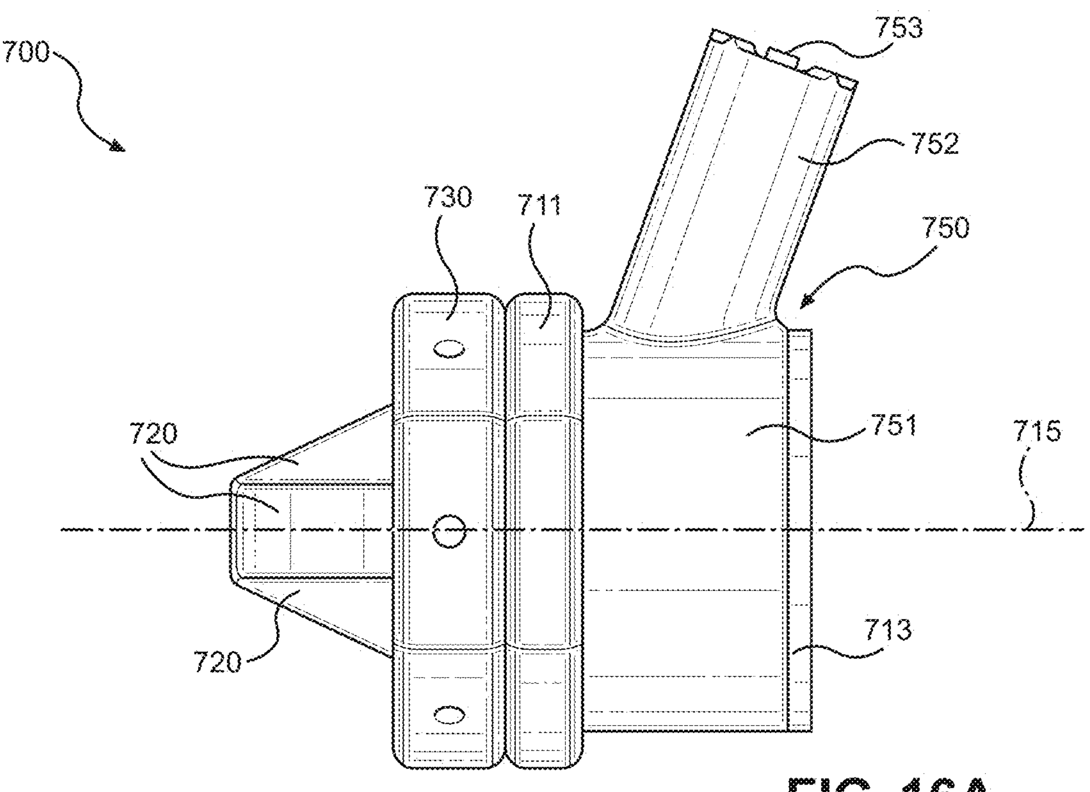
FIG. 16A illustrates in side elevation view an example medical device chuck and rotating sleeve component according to one embodiment of the present disclosure.
Figure 16B:
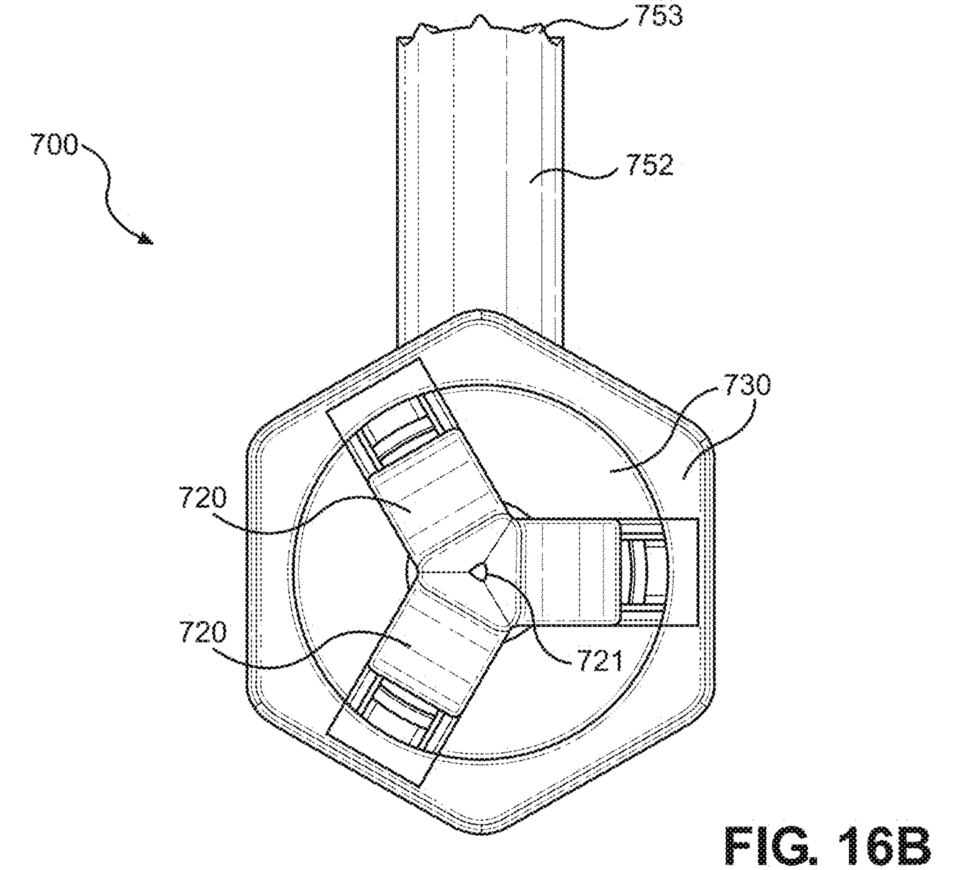
FIG. 16B illustrates in front elevation view the medical device chuck and rotating sleeve component of FIG. 16A according to one embodiment of the present disclosure.

Turning next to FIGS. 16A and 16B, an example medical device chuck and rotating sleeve component is illustrated in side elevation and front elevation views respectively. As in the case of FIG. 15C, a rotatable fiducial marker array is not shown here for purposes of simplicity in illustration. It will be understood that any suitable rotatable fiducial marker array, such as array 200 or array 500 above, for example, can be rotatably coupled to crown coupling component 753 of rotating sleeve component 750 in an identical or similar manner to that which is shown and described for clamp coupling component 170 in FIG. 2C above or crown coupling component 9 in FIG. 9A above.

Again, medical device chuck 700 can include a main body having front and back regions 711, 713, a plurality of jaws 720, and a chuck adjustment mechanism 730. Rotating sleeve component 750 can be a separate item rotationally coupled to medical device chuck 700 or can be considered as part of the medical device chuck in some arrangements. Rotating sleeve component 750 can include a rotating sleeve 751, a rotating post 752 coupled to and extending outward from the rotating sleeve, and a crown coupling component 753 located at a distal end of the rotating post. Rotating sleeve 751 can be captured or held within a captive collar arrangement between front region 711 and back region 713 of the main body of medical device chuck 700, and this rotating sleeve can be configured to rotate freely around the main body. As such, rotating sleeve 751, rotating post 752, crown coupling component 753, and a rotatable fiducial marker array coupled to the crown coupling component can all be considered as rotating items that rotate freely together around the main body of medical device chuck 700. Such free rotation can be about main body longitudinal axis 715. As shown in FIG. 16B, each of the plurality of jaws 720 can include an indent 721 at a top inner surface thereof, with these indents being collectively sized and shaped to facilitate clamping onto a cylindrical portion of a separate medical device or other object that extends along main body longitudinal axis 715.

Figures 17A, 17B:
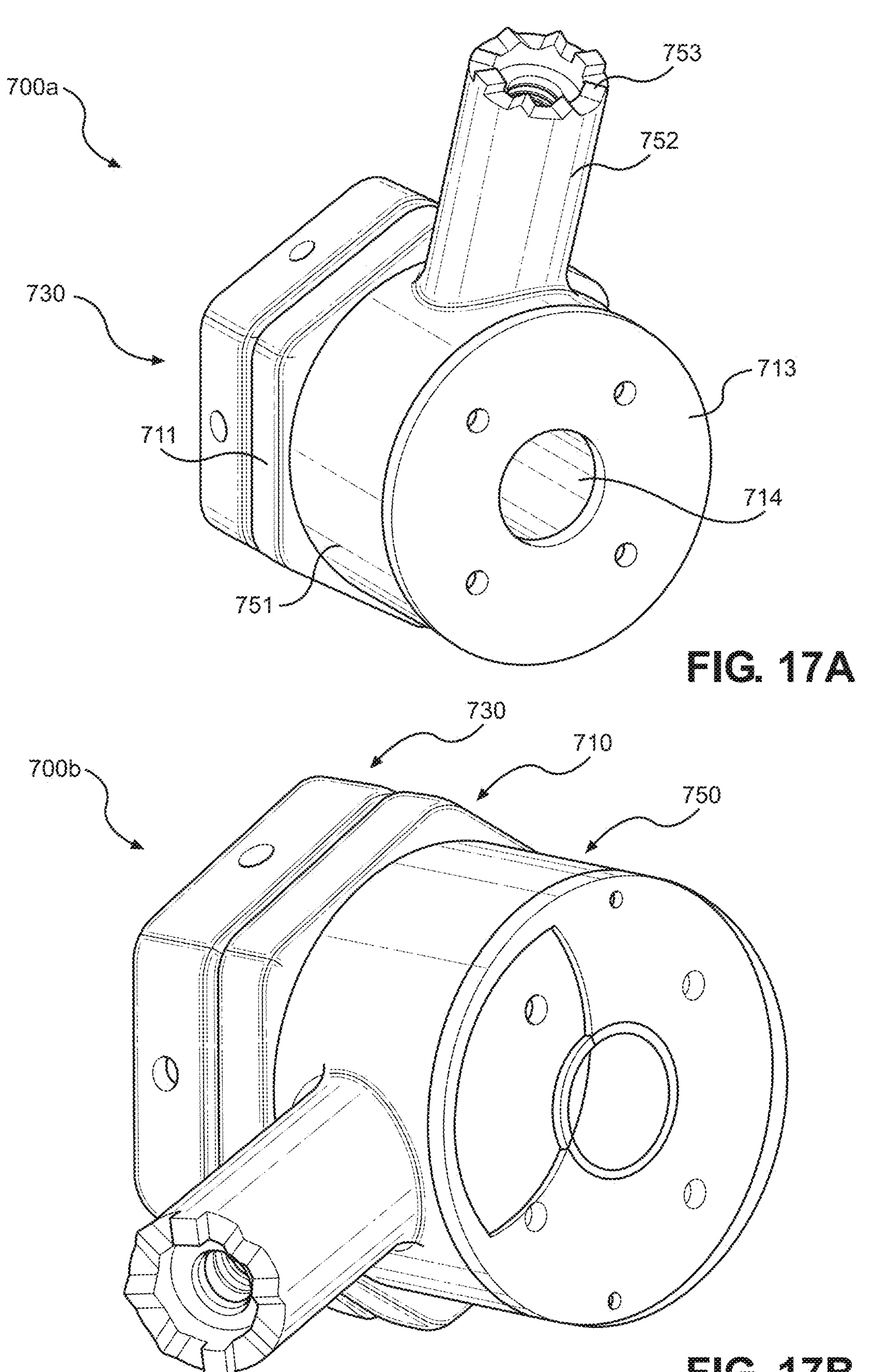
FIG. 17A illustrates in rear perspective view the medical device chuck and rotating sleeve component of FIG. 16A with its rotating post extending upward according to one embodiment of the present disclosure.
FIG. 17B illustrates in rear perspective view the medical device chuck and rotating sleeve component of FIG. 17A with its rotating post extending sideways according to one embodiment of the present disclosure.

Continuing with FIGS. 17A and 17B, medical device chuck 700 and rotating sleeve component 750 are illustrated in rear perspective views with the rotating post 752 extending in different directions. FIG. 17A shows medical device chuck configuration 700*a* with rotating post 752 extending upward, while FIG. 17B shows medical device chuck configuration 700*b* with the rotating post extending sideways. Again, a separate rotatable fiducial marker array (not shown) can be rotatably coupled to and rotationally locked in place with respect to crown coupling component 753 at the extended distal end of rotating post 752. As shown in FIG. 17B, configuration 700*b* can reflect rotating sleeve component 750 being rotated about 90 degrees counterclockwise from its position in configuration 700*a*. As such, rotating post and the attached rotatable fiducial marker array are also rotated this same 90 degrees. It will be understood that rotating sleeve component can be configured such that it can freely rotate in either direction completely around main body 710 of medical device chuck 700. In some arrangements, one or more bearings or friction elements can be used to facilitate a smooth rotational ability between rotating sleeve 751 and the middle region of main body 710.

As noted in the foregoing embodiments, it can be advantageous to know exactly where some or all of the fiducial markers are located or fixed in three-dimensional space when using the disclosed medical fiducial marker systems. As such, calibration of fiducial marker locations can be a common process step after the fiducial marker array is locked in place rotationally to a respective coupling component, such as crown coupling component 753. Again, medical device chuck 700 is arranged such that its main body longitudinal axis 715 can always coincide with the cylindrical longitudinal axis 5 of whatever separate object is clamped within the jaws of its chuck regardless of the size of the separate object and the diameter of its cylindrical portion. This advantageous feature can allow for calibrating fiducial marker locations with respect to the longitudinal axis before the separate object is even located and clamped within the medical device chuck. Accordingly, so long as the fiducial marker array is not replaced or repositioned rotationally, recalibration of fiducial marker locations need only be performed with respect to the separate object tip when the separate object is replaced or adjusted lengthwise within the medical device chuck.

Figure 18:
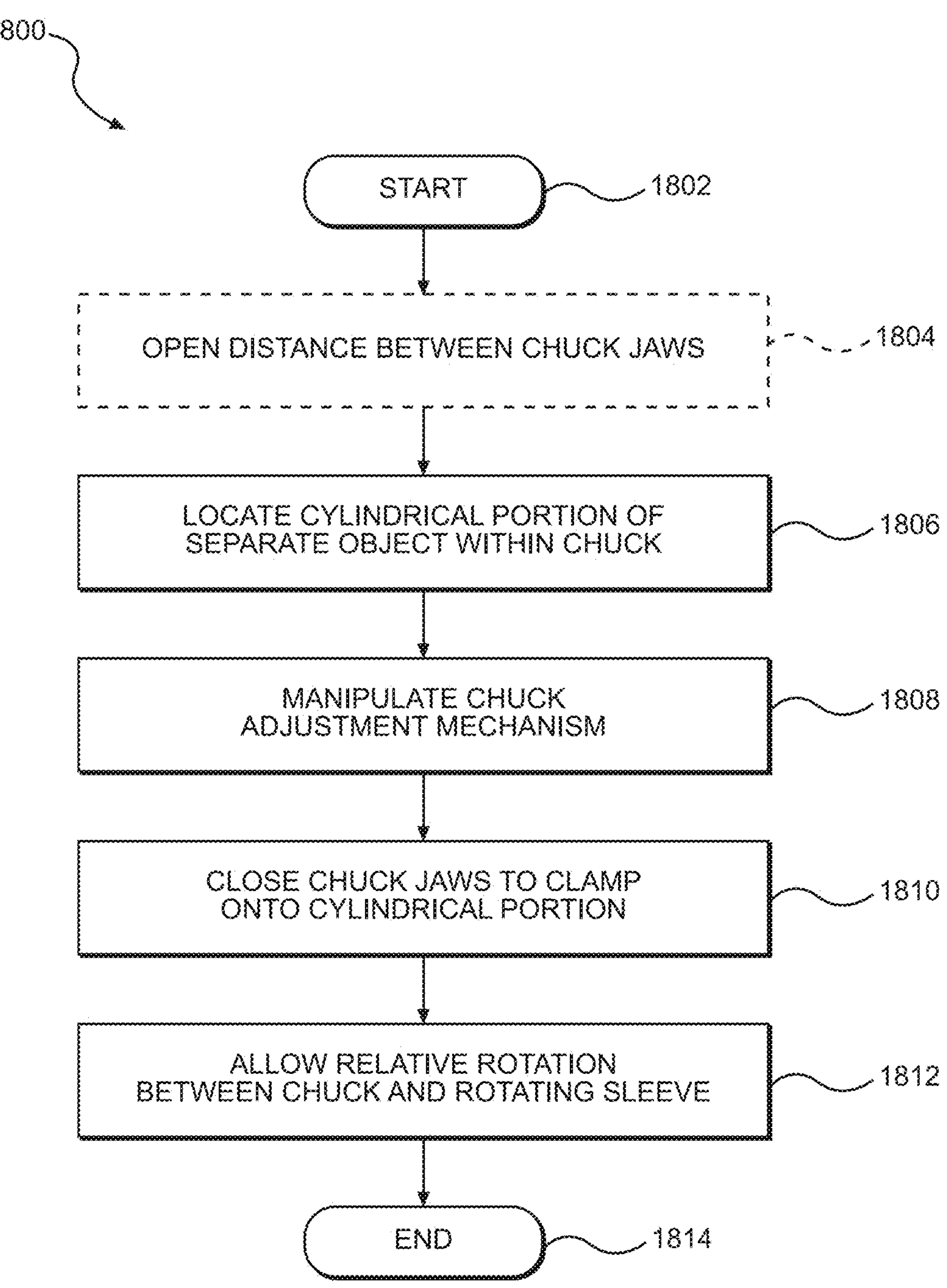
FIG. 18 illustrates a flowchart of an example summary method of using a mechanical chuck according to one embodiment of the present disclosure.

FIG. 18 provides a flowchart of an example summary method of using a mechanical chuck. Summary method 1800 can represent one broad aspect for overall methods of use for a mechanical chuck, and it will be understood that various other steps, features, and details of such a broad aspect and overall methods of use are not provided here for purposes of simplicity. While the mechanical chuck can be a medical device chuck designed for use with a pedicle probe or other medical probe or device as disclosed herein, it is contemplated that the mechanical chuck can also be used with other objects and in other environments and applications as will be appreciated by those of skill in the art.

After a start step 1802, an optional first process step 1804 can involve opening the distance between a plurality of jaws on the mechanical chuck. This can involve rotating an outer adjustment ring or otherwise manipulating a chuck adjustment mechanism backwards so as to move the jaws radially apart from each other. This can be done in situations where the jaws are too close together to be able to accept a cylindrical portion of a desired separate object between the jaws. The separate object can be a medical device such as a pedicle probe, for example, although other types of objects are also possible. Step 1804 can be optional in some situations, such as where the jaws are already situated such that the jaws are sufficiently far apart to be able to locate the cylindrical portion of the separate object between the jaws. Step 1804 can be performed manually or automatically in some cases, such as where a separate robotic system can be configured to manipulate the chuck adjustment mechanism.

At the following process step 1806, the separate object can be located within the mechanical chuck. This can involve placing a cylindrical portion of the separate object between the plurality of jaws, and can also involve placing the cylindrical portion along a central opening extending through an entire main body of the mechanical chuck such that the cylindrical portion extends past both a front side or region and a back side or region of the mechanical chuck. Step 1806 can be manually or automatically performed, such as where a separate robotic system can be configured to move and locate the separate object appropriately.

At subsequent process step 1808, an adjustment mechanism of the chuck can be manipulated in an appropriate direction while the cylindrical portion is located between the plurality of jaws and extends past both the front and back sides of the main body. Step 1808 can be manually or automatically performed, such as where a separate robotic system can be configured to rotate an outer adjustment ring of the adjustment mechanism in the right direction.

The next process step 1810 can involve closing the plurality of jaws radially inward and onto the cylindrical portion, which can take place as a result of manipulating the adjustment mechanism. The plurality of jaws include can contact regions that clamp onto the cylindrical portion such that the mechanical chuck cannot slide laterally along the cylindrical portion or pivot or rotate about the longitudinal axis relative to the cylindrical portion. Step 1810 can be manually or automatically performed, such as where closing the jaws toward each other and onto the cylindrical portion is a natural physical consequence of manipulating the adjustment mechanism on the chuck.

At the following process step 1812, relative rotation can be allowed between the mechanical chuck and a rotating sleeve component coupled to the mechanical chuck. This can be done while the contact regions of the jaws are clamped onto the cylindrical portion, and the relative rotation can be about a longitudinal axis, which can be both the longitudinal axis of the cylindrical portion and the longitudinal axis of the mechanical chuck main body. This can include the separate object forming a combined unit with the mechanical chuck regarding the relative rotation with the rotating sleeve component. Step 1812 can be manually or automatically performed, such as where the relative rotation is a natural physical consequence of a physical arrangement between the mechanical chuck and the rotating sleeve component.

In some arrangements, the rotating sleeve component can be held within a captive collar arrangement at the main body of the mechanical chuck such that the rotating sleeve component is configured to facilitate a full range of rotational motion between the main body and the rotating sleeve component. In some arrangements, the rotating sleeve component can include another object such as a fiducial marker array rotatably coupled thereto. The method can then end at end step 1814.

Figure 19A:
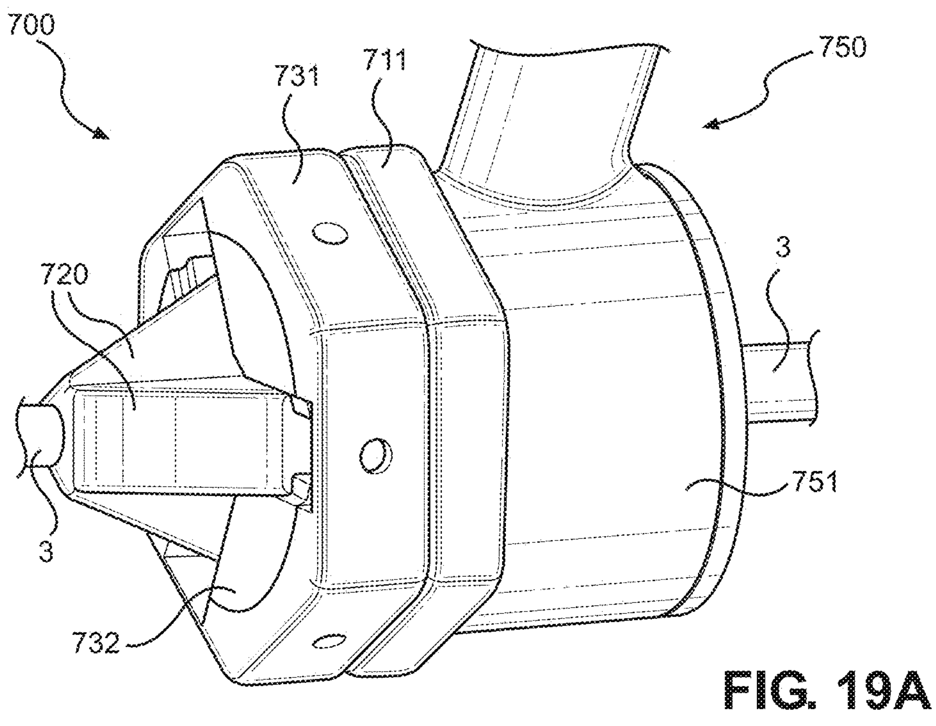
FIG. 19A illustrates in side perspective view an example medical device chuck and rotating sleeve component according to one embodiment of the present disclosure.

Moving next to FIGS. 19A-19D, a medical device chuck is shown in side perspective views at various stages of disassembly. FIG. 19A illustrates a fully assembled medical device chuck 700 and rotating sleeve component 750 coupled thereto. As detailed above, the rotating sleeve component 750 can be held within a captive collar arrangement such that its rotating sleeve 751 can rotate freely around a main body of medical device chuck 700. Again, medical device chuck 700 can include a plurality of jaws 720 that can clamp onto a cylindrical portion 3 of a separate object held by the chuck, a main body including a front region 711, and a chuck adjustment mechanism that can include a rotatable outer adjustment ring 731 that surrounds and rotates a chuck adjustment body 732 that in turn holds and rotates the plurality of jaws.

Figure 19B:
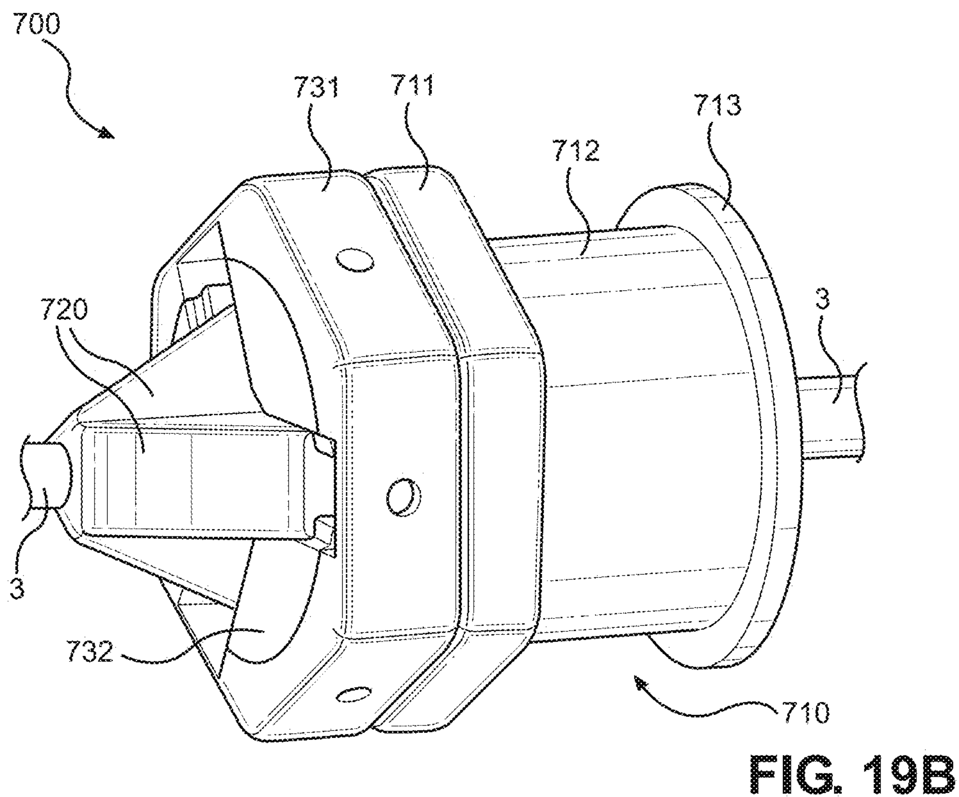
FIG. 19B illustrates in side perspective view the medical device chuck of FIG. 19A with no rotating sleeve component according to one embodiment of the present disclosure.

FIG. 19B depicts the medical device chuck 700 without the rotating sleeve component coupled thereto. As detailed above, main body 710 can include front region 711, middle region 712, and back region 713, which can combine to form the captive collar arrangement to hold the rotating sleeve component therein. Rotatable outer adjustment ring 731 can be rotated with respect to main body front region 711 in one direction to open the plurality of jaws 720 and in the other direction to close together the plurality of jaws.

Figure 19C:
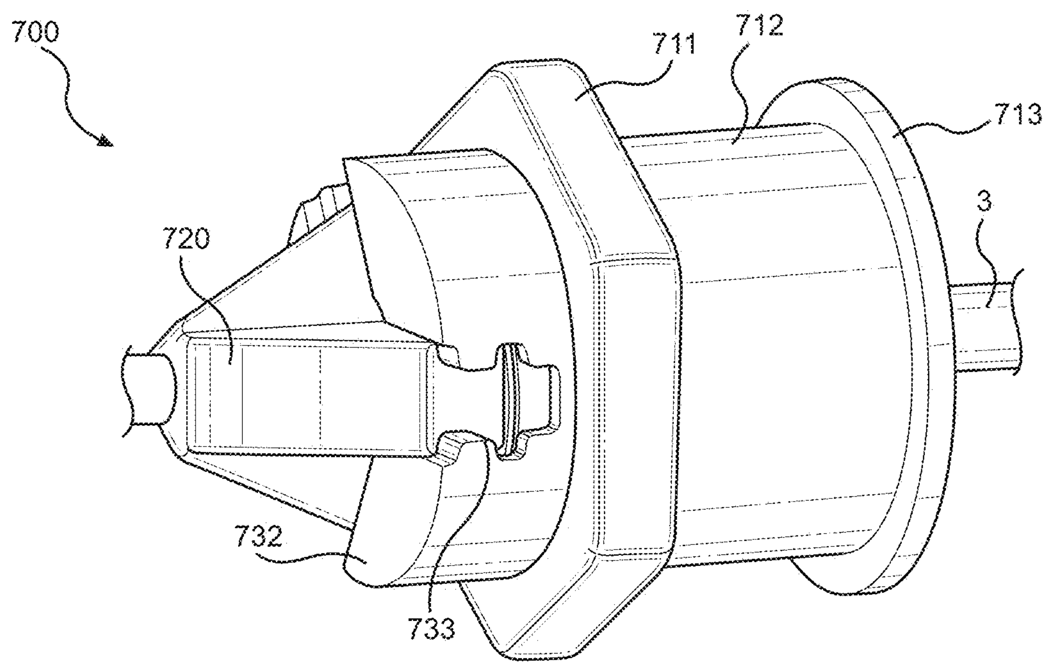
FIG. 19C illustrates in side perspective view the medical device chuck of FIG. 19B with its outer adjustment ring removed according to one embodiment of the present disclosure.

FIG. 19C shows the medical device chuck 700 with its outer adjustment ring removed. Chuck adjustment body 732 can be arranged to hold the plurality of jaws 720 therein while allowing the jaws to move radially inward to close together and radially outward to open or separate the jaws apart. Such jaw movement can be facilitate by way of a radial opening 733 through the chuck adjustment body 732 for each of the individual jaws.

Figure 19D:
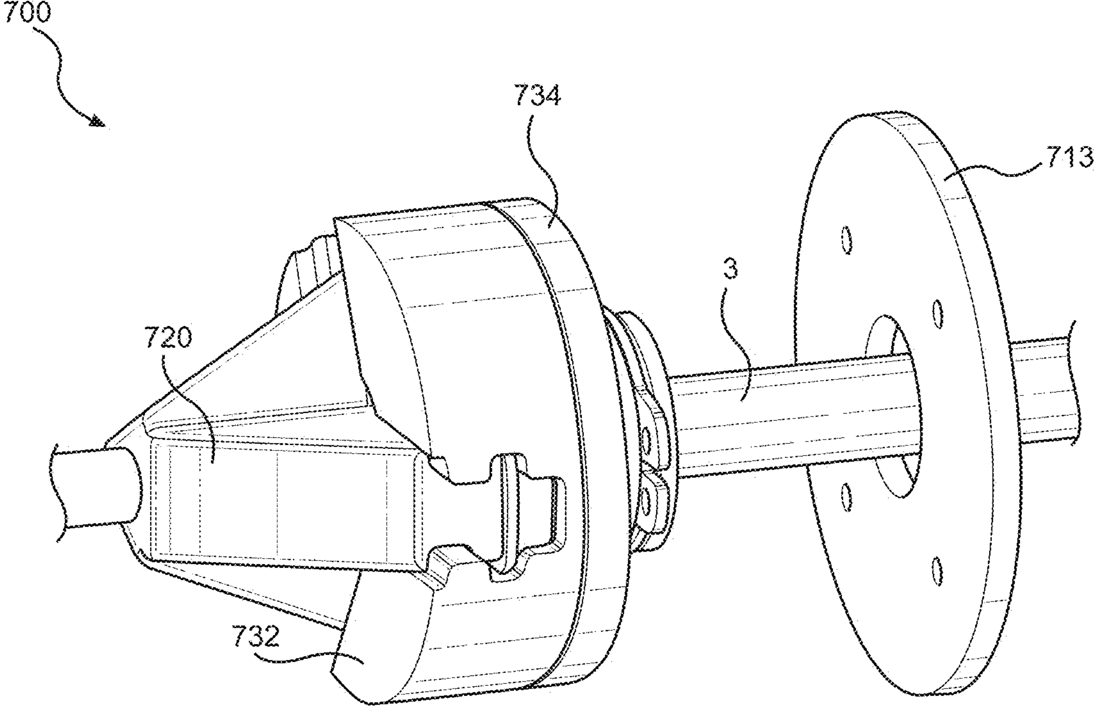
FIG. 19D illustrates in side perspective view the medical device chuck of FIG. 19C with the front and middle regions of its main body removed according to one embodiment of the present disclosure.

FIG. 19D illustrates the medical device chuck 700 with the front and middle regions of its main body removed. As shown, removing the front and middle regions 711, 712 of the main body 710 exposes a scroll plate 734 of the chuck adjustment mechanism and the cylindrical portion 3 of the separate object that extends all the way through and beyond both ends of medical device chuck 700.

Figure 20A:
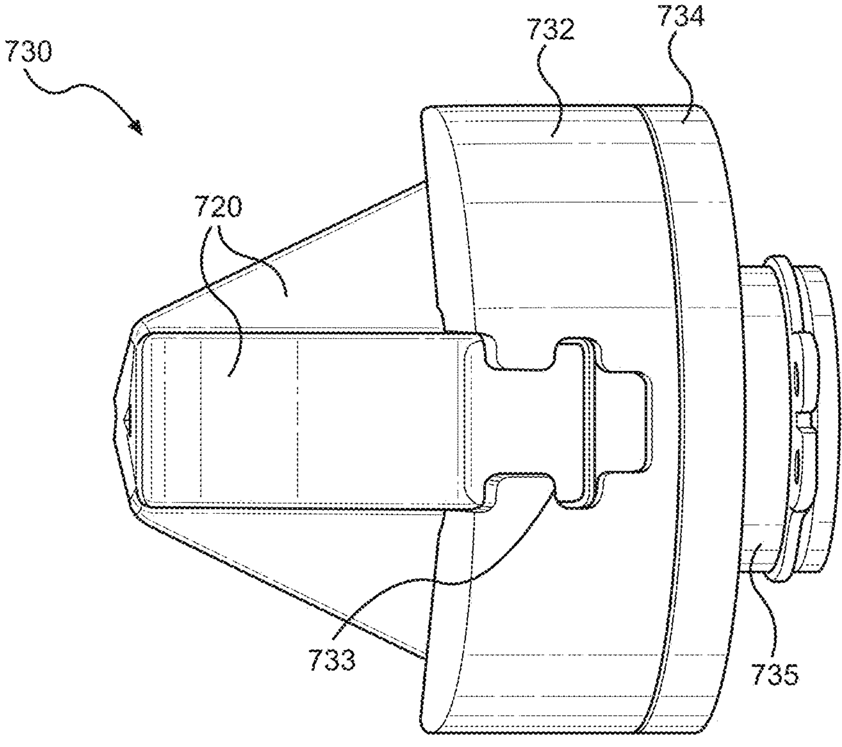
FIG. 20A illustrates in side elevation view an example chuck mechanism for a medical device chuck according to one embodiment of the present disclosure.
Figure 20B:
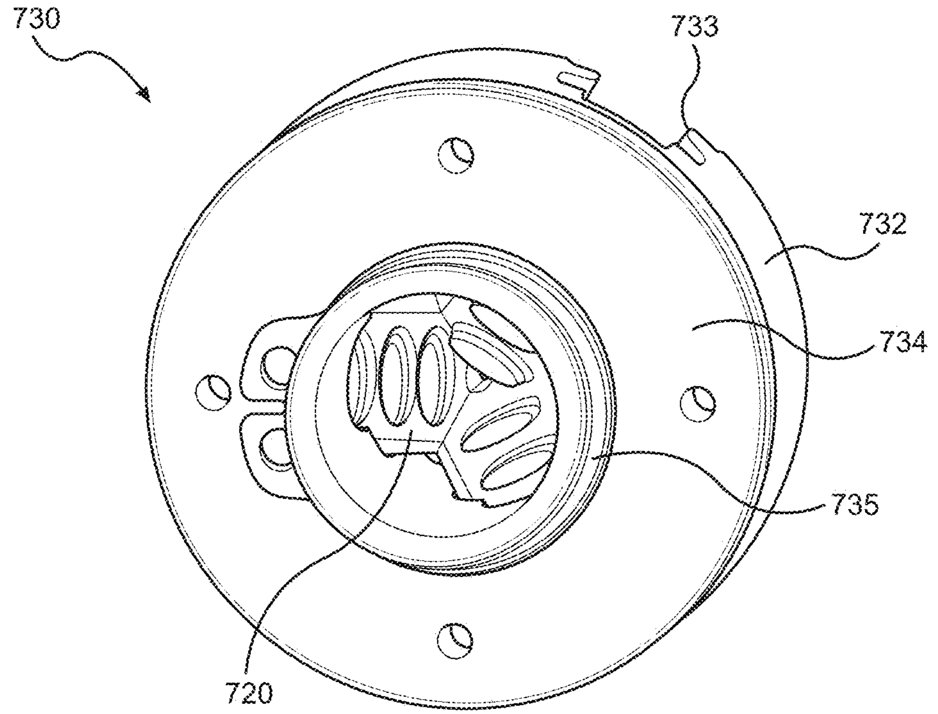
FIG. 20B illustrates in rear perspective view the chuck mechanism of FIG. 20A according to one embodiment of the present disclosure.

Continuing with FIGS. 20A-20F various components and features of a chuck adjustment mechanism for a medical device chuck are shown. FIGS. 20A and 20B illustrate chuck adjustment mechanism 730 in side elevation and rear perspective views respectively. In various embodiments, medical device chuck 700 can operate as a self-centering scroll chuck, and as such chuck adjustment mechanism 730 can have various components and features that are the same or similar to those found in a scroll chuck. For example, chuck adjustment mechanism 730 can include a rotatable outer adjustment ring (not shown) that surrounds and functions to rotate a chuck adjustment body 732 with a radial opening 733 therethrough for each of the plurality of jaws 720. The outer adjustment ring and chuck adjustment body 732 can rotate together with respect to a stationary scroll plate 734. A cylindrical shell portion 735 of chuck adjustment body 732 can extend through and behind scroll plate 734 to facilitate proper alignment and smooth relative rotation of the adjustment body against the scroll plate, and this assembly can be kept in place by one or more snap rings or clips, as shown.

Figure 20C:
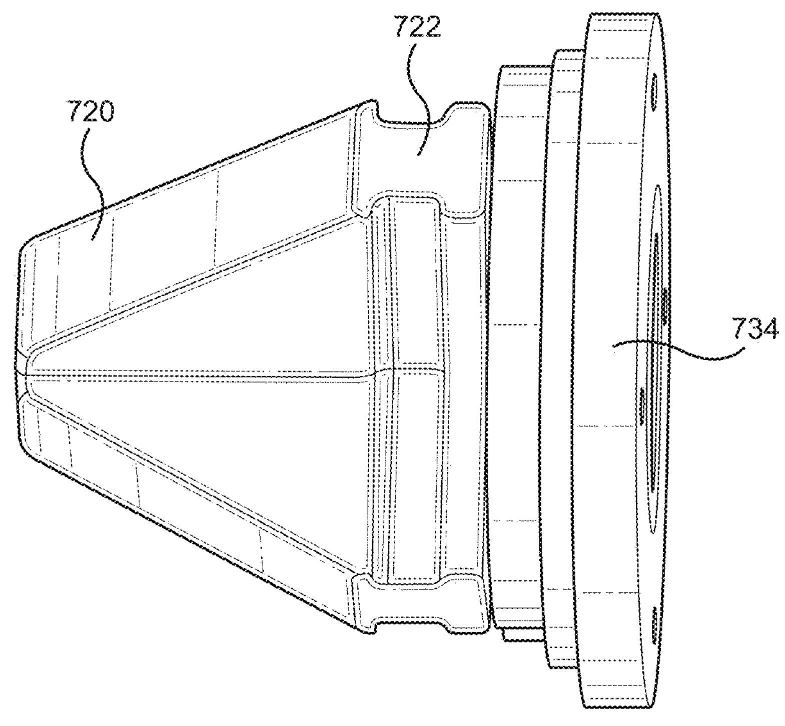
FIG. 20C illustrates in side elevation view the chuck mechanism of FIG. 20A with its adjustment body removed according to one embodiment of the present disclosure.
Figure 20D:
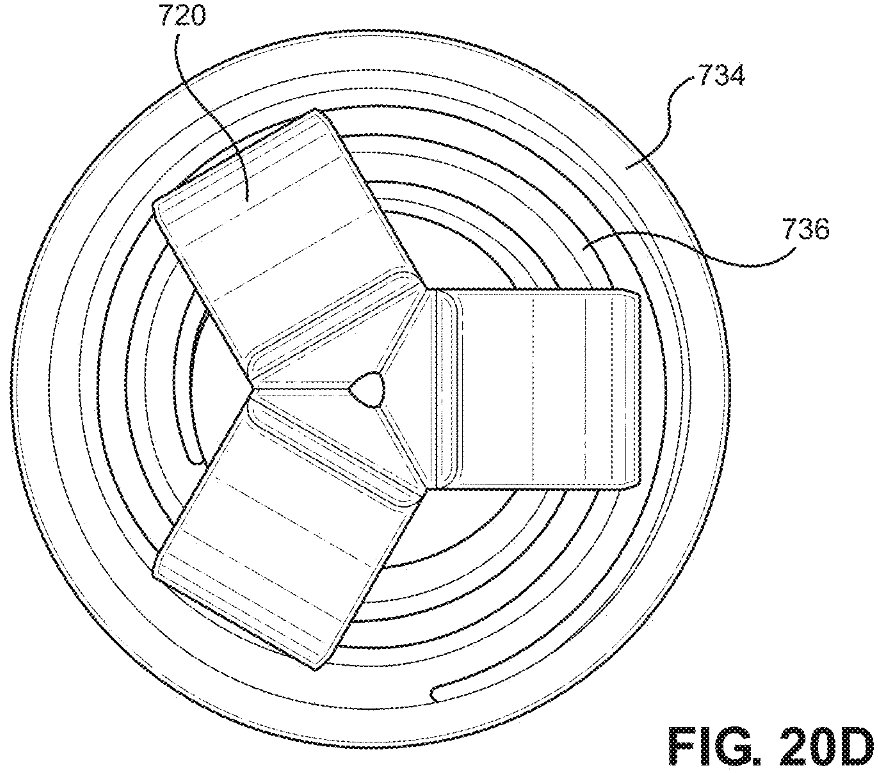
FIG. 20D illustrates in front elevation view the chuck mechanism of FIG. 20C with the adjustment body removed according to one embodiment of the present disclosure.

FIGS. 20C and 20D illustrate chuck mechanism 730 with its chuck adjustment body removed in side elevation and front elevation views respectively. As shown, all that remains for purposes of illustration here are the plurality of jaws 720 as arranged against scroll plate 734. Each of the plurality of jaws 720 can have a grooved base portion 722 that is sized and shaped to facilitate radial movement of the jaw back and forth along a respective radial opening in the chuck adjustment body (not shown), as will be readily appreciated. The base portion of each of the plurality of jaws 720 can mate with a spiral groove 736 located along an inner face of scroll plate 734, such that rotation of the jaws with respect to the scroll plate forces the jaws to move radially inward or outward with respect to each other depending on the direction of rotation.

Figure 20E:
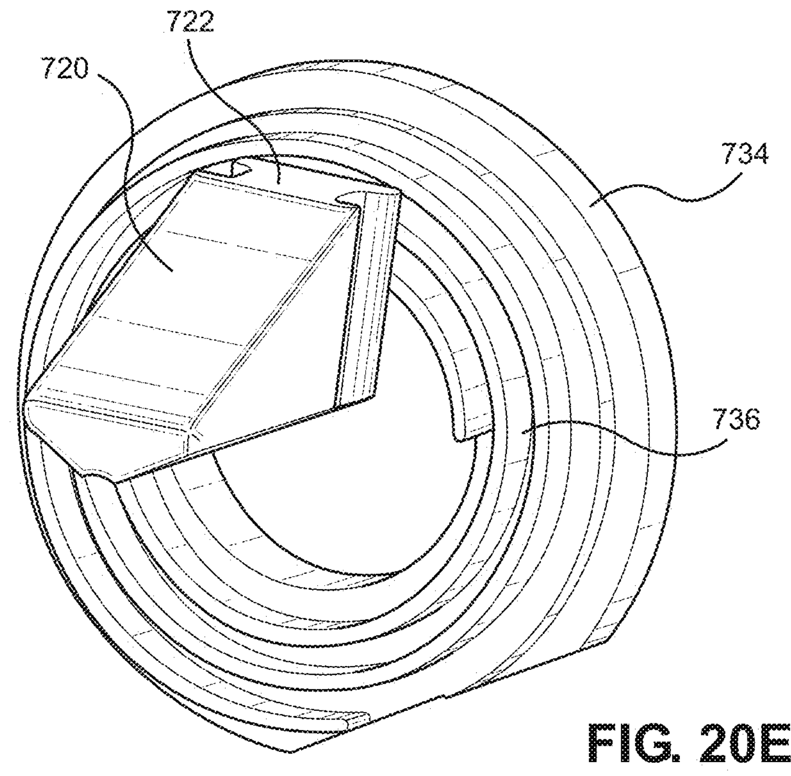
FIG. 20E illustrates in front perspective view an example scroll plate and single jaw for the chuck mechanism of FIG. 20A according to one embodiment of the present disclosure.
Figure 20F:
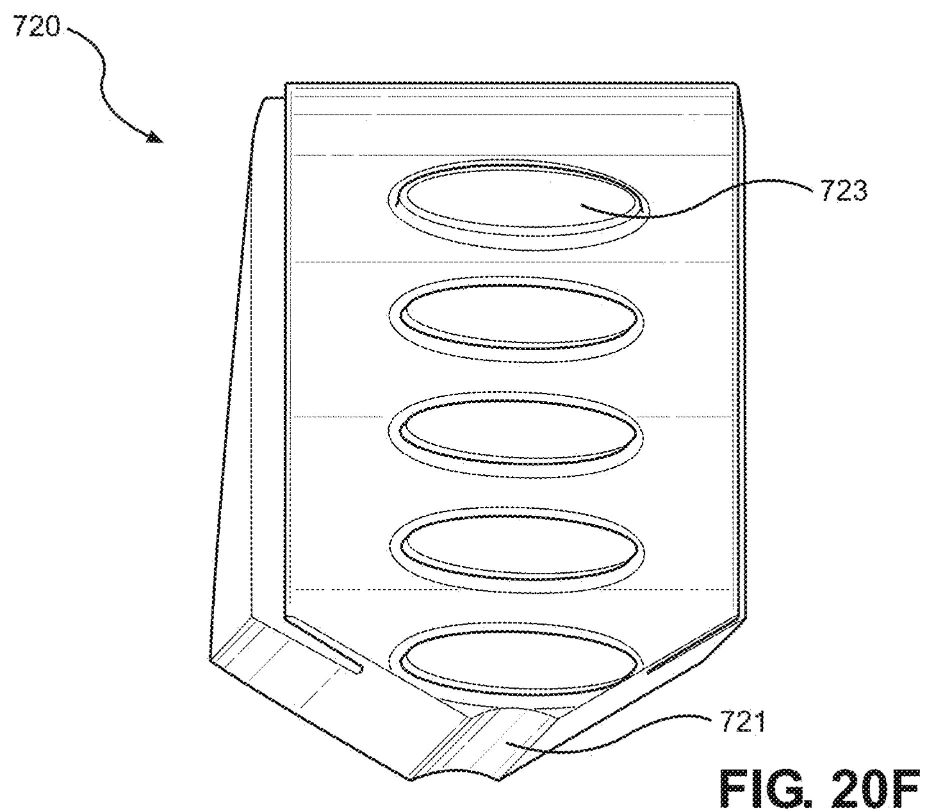
FIG. 20F illustrates in rear perspective view an example single jaw for the chuck mechanism of FIG. 20A according to one embodiment of the present disclosure.

FIG. 20E illustrates in front perspective view an example scroll plate and single jaw for the chuck adjustment mechanism of a medical device chuck, while FIG. 20F illustrates in rear perspective view an example single jaw configured for interaction with the chuck adjustment mechanism. In addition to its grooved base portion 722 that forces each jaw 720 to move radially inward or outward along a respective radial opening in the chuck adjustment body, each of the plurality of jaws can also have a plurality of teeth or protrusions 723 along a bottom surface thereof. These protrusions 723 can be sized, shaped, and dimensioned to fit within the internal spiral groove 736 on scroll plate 734, such that the internal spiral groove is configured to radially move each of the plurality of jaws simultaneously and symmetrically inward or outward when the chuck adjustment body holding the plurality of jaws is rotated with respect to the scroll plate, as will be readily understood by those of skill in the art.

Figure 21:
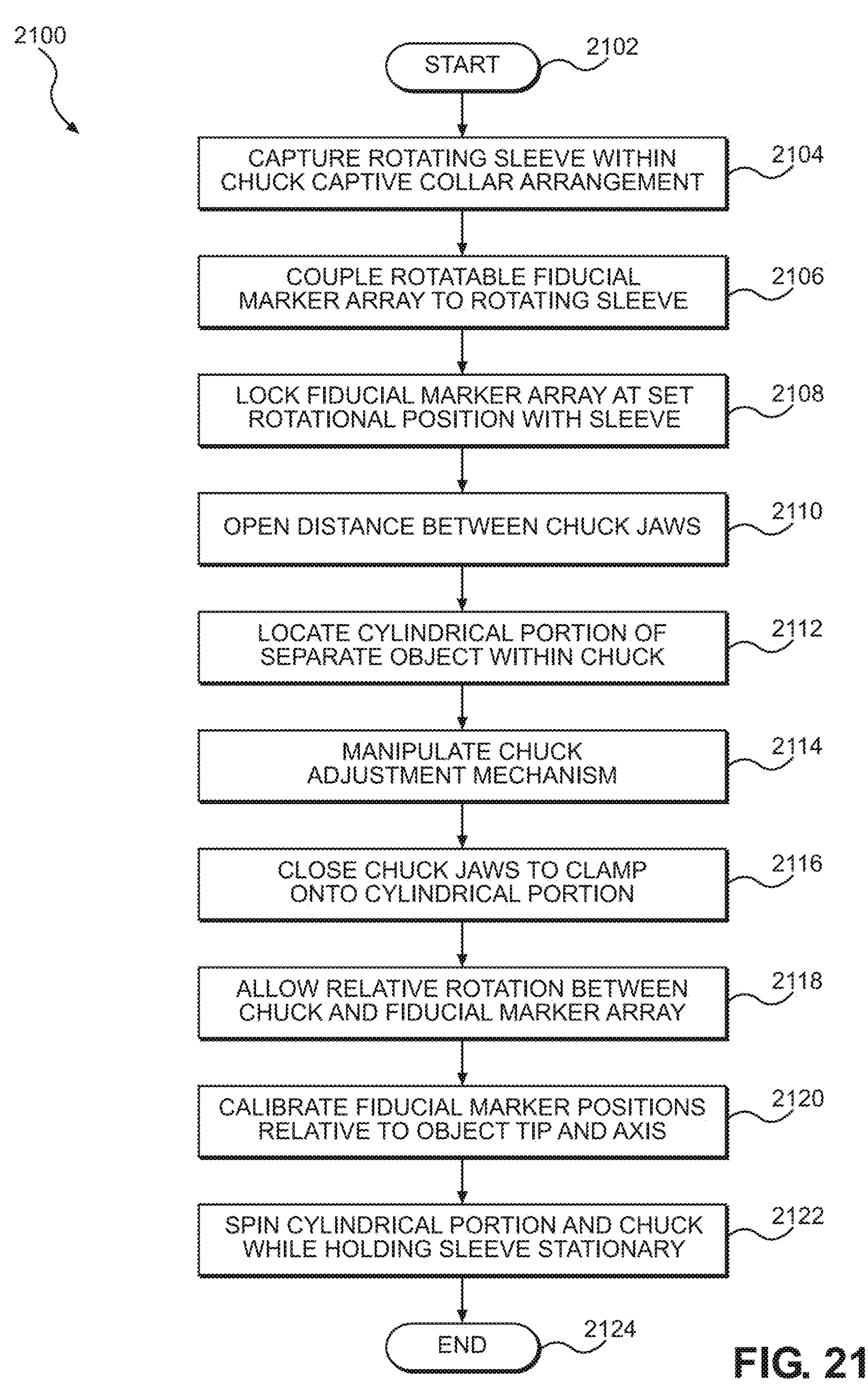
FIG. 21 illustrates a flowchart of an example detailed method of using a mechanical chuck according to one embodiment of the present disclosure.

Moving now to FIG. 21, a flowchart of an example detailed method of using a mechanical chuck is provided. Detailed method 2100 can represent one possible way of using a mechanical chuck, and it will be understood that various other steps, features, and alternatives for such a detailed method are not provided here for purposes of simplicity. Detailed method 2100 can include some or all of the steps and features of summary method 1800 above, as will be readily appreciated. In some arrangements, the mechanical chuck can be a medical device chuck configured for use with a medical device during a medical procedure. After a start step 2102, a first process step 2104 can involve capturing a rotating sleeve component within a captive collar arrangement at the main body of the mechanical chuck. This can involve some or all of the components and features illustrated and described above with respect to mechanical chuck 700. Step 2104 can be manually or automatically performed, such as where a separate robotic system can be configured to handle the rotating sleeve component to capture it in place on the chuck.

A following process step 2106 can involve coupling a rotatable fiducial marker array to the rotating sleeve component. In particular, the fiducial marker array can be coupled to a rotating post of the rotating sleeve component, as noted above. This coupling step can be similar to step 604 above where a fiducial marker array is rotationally coupled to a pivotable clamp or step 1204 above where a fiducial marker array is rotationally coupled to another object. Step 2106 can be performed manually or automatically in some cases, such as where a separate robotic system can be configured to handle the fiducial marker array and effect its coupling to the rotating sleeve component.

At subsequent process step 2108, the rotatable fiducial marker array can be locked at a set rotational position with respect to the rotating sleeve component. This step can be similar to steps 618 or 1210 in the detailed methods above regarding locking a fiducial marker array in place relative to the component to which it is coupled. Step 2108 can be manually or automatically performed, such as where a separate robotic system can be configured to handle the fiducial marker array and lock its rotational position in place with respect to the rotating sleeve component.

The next process step 2110 can involve opening the distance between a plurality of jaws on the mechanical chuck. This can be identical or similar to step 1804 in summary method 1800 above in that it can involve rotating an outer adjustment ring or otherwise manipulating a chuck adjustment mechanism backwards so as to move the jaws radially apart from each other. Again, the separate object can be a medical device such as a pedicle probe, for example, although other types of objects are also possible. Step 2110 can be performed manually or automatically in some cases, such as where a separate robotic system can be configured to manipulate the chuck adjustment mechanism.

At a following process step 2112, the separate object can be located within the mechanical chuck. Like step 1806 above, this can involve placing a cylindrical portion of the separate object between the plurality of jaws and can also involve placing the cylindrical portion along a central opening extending through an entire main body of the mechanical chuck such that the cylindrical portion extends past both a front side or region and a back side or region of the mechanical chuck. Step 2112 can be manually or automatically performed, such as where a separate robotic system can be configured to move and locate the separate object appropriately.

Subsequent process step 2114 can involve manipulating an adjustment mechanism of the chuck in an appropriate direction while the cylindrical portion is located between the plurality of jaws and extends past both the front and back sides of the main body. Step 2114 can correlate to step 1808 above, and can be manually or automatically performed, such as where a separate robotic system can be configured to rotate an outer adjustment ring of the adjustment mechanism in the right direction.

At the next process step 2116, the plurality of jaws can be closed radially inward and onto the cylindrical portion, which can take place as a result of manipulating the adjustment mechanism. As in the case of step 1810 above, the plurality of jaws include can contact regions that clamp onto the cylindrical portion such that the mechanical chuck cannot slide laterally along the cylindrical portion or pivot or rotate about the longitudinal axis relative to the cylindrical portion. Step 2116 can be manually or automatically performed, such as where closing the jaws toward each other and onto the cylindrical portion is a natural physical consequence of manipulating the adjustment mechanism on the chuck.

At the following process step 2118, relative rotation can be allowed between the mechanical chuck and a rotating sleeve component coupled to the mechanical chuck, similar to that which is set forth in summary method step 1812 above. This can again be done while the contact regions of the jaws are clamped onto the cylindrical portion, and the relative rotation can be about a longitudinal axis, which can be both the longitudinal axis of the cylindrical portion, the longitudinal axis of the mechanical chuck main body, or both. This can include the separate object forming a combined unit with the mechanical chuck regarding the relative rotation with the rotating sleeve component. Step 2118 can be manually or automatically performed, such as where the relative rotation is a natural physical consequence of a physical arrangement between the mechanical chuck and the rotating sleeve component.

At the next process step 2120, the positions of fiducial markers located on the rotatable fiducial maker array can be calibrated relative to both the longitudinal axis of the cylindrical portion and the tip of the separate medical device or other separate object when it is clamped within the mechanical chuck. These calibrated positions can then be known fiducial marker positions in three dimensional space for any use of the separate medical device or other object so long as the separate medical device or object remains clamped within the chuck and the fiducial marker array remains locked at its set rotational position. Step 2120 can be manually or automatically performed, such as where a separate augmented reality system having cameras, detectors, software, and the like can be configured to detect and locate the relative positions of the fiducial markers once the fiducial marker array is locked in place relative to the separate object and the separate object is clamped within the mechanical chuck.

The next step 2122 can involve spinning the cylindrical portion of the separate medical device and the medical device chuck as a combined unit while holding the rotating sleeve component stationary. This can involve, for example, a surgeon or other operator to hold the rotating post of the rotating sleeve component in place while spinning or rotating the cylindrical portion of a surgical probe or other separate object while the cylindrical portion is clamped in place with the medical device chuck. Of course, holding the rotating post in place results in holding the fiducial marker array in place as well. As will be readily appreciated, this inverse relative rotational or spinning action between the cylindrical portion and the rotating fiducial marker array has the same effect with respect to knowing the calibrated locations of the fiducial markers as holding the cylindrical portion in place and rotating the fiducial marker array around the mechanical chuck and cylindrical portion. Either way of facilitating relative rotational motion is acceptable for purposes of the disclosed arrangements and allowing the surgeon or operator to spin the cylindrical portion of a medical probe or tool provide added flexibility in using the disclosed mechanical chuck and its medical fiducial marker system, as may be desired. The method can then end at end step 2124.

For foregoing method 2100, it will be appreciated that not all process steps are necessary, and that other process steps may be added in some arrangements. For example, replacing the fiducial marker array, the rotating sleeve arrangement, the mechanical chuck, or any combination thereof might be desirable added steps. This can allow for interchangeable use with arrays, chucks, and separate medical devices or objects of different sizes and/or geometries. Furthermore, the order of steps may be altered in some cases, and some steps may be performed simultaneously. For example, step 2120 may be performed earlier in the process in some cases, or step 2120 may be bifurcated so that calibration with respect to the longitudinal axis can be performed once the fiducial marker array is rotationally locked into place and before any cylindrical object is clamped within the chuck. As another example, steps 2114 and 2116 can be performed simultaneously. Although known process steps are provided for various techniques in detailed method 2100, it will be appreciated that any other suitable similar method for using a medical device chuck or other mechanical chuck can also be used. Other extrapolations and variations of the disclosed methods will also be readily appreciated by those of skill in the art.

Figure 22A:
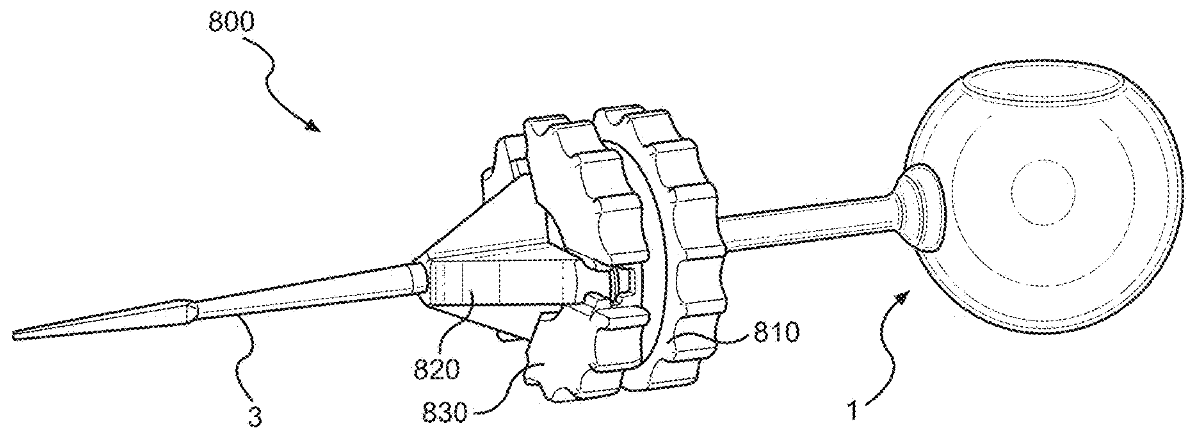
FIG. 22A illustrates in side perspective view an example alternative medical device chuck as being clamped to a separate medical device according to one embodiment of the present disclosure.

Next, FIG. 22A illustrates in side perspective view an example alternative medical device chuck as being clamped to a separate medical device. Alternative medical device chuck 800 can be similar to medical device chuck 700 above, albeit with several design differences and other features. For example, alternative medical device chuck can have a shorter main body 810, longer jaws 820 having increased contact regions for clamping onto cylindrical portion 3 of separate object 1, and a chuck adjustment mechanism 830 having contoured outer edges to facilitate better grip and control when rotating an outer adjustment ring to move the jaws. Other components, design differences, and added features are also possible for the disclosed medical device chucks or any other suitable mechanical chuck arranged to clamp onto a cylindrical object in the manner and with the advantages disclosed herein.

Figure 22B:
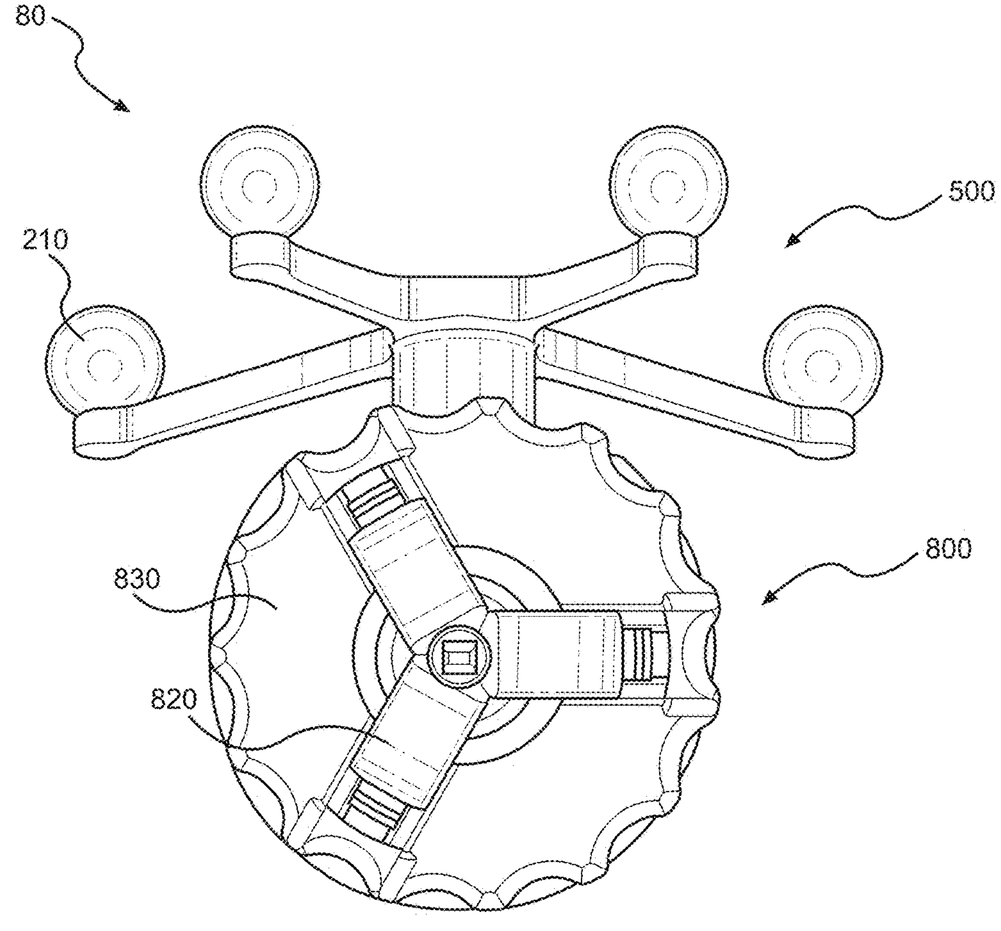
FIG. 22B illustrates in front elevation view another example alternative medical fiducial marker system with a fiducial marker array rotationally coupled to the alternative medical device chuck of FIG. 22A according to one embodiment of the present disclosure.

Lastly, FIG. 22B illustrates in front elevation view another example alternative medical fiducial marker system with a fiducial marker array rotationally coupled to the alternative medical device chuck of FIG. 22A. Alternative medical fiducial marker system 80 can include rotatable fiducial marker array 500 as disclosed above rotationally coupled with respect to alternative medical device chuck 800 as disclosed above. Such coupling can be facilitate by way of a rotating sleeve component (not shown) with a shortened rotating post or other similar arrangement that allows rotating fiducial marker array 500 to be a rotating array that can rotate all the way around the main body of alternative medical device chuck 800. Other variations, design changes, features, and extrapolations are also possible to arrive at similar medical fiducial marker systems having medical device chucks and rotating fiducial marker arrays with the same functionalities and advantages as those disclosed herein.

Although the foregoing disclosure has been described in detail by way of illustration and example for purposes of clarity and understanding, it will be recognized that the above described disclosure may be embodied in numerous other specific variations and embodiments without departing from the spirit or essential characteristics of the disclosure. Certain changes and modifications may be practiced, and it is understood that the disclosure is not to be limited by the foregoing details, but rather is to be defined by the scope of the appended claims.

What is claimed is:

1. A fiducial marker array, comprising:

a rigid body configured to support a plurality of fiducial markers at fixed locations relative to each other along the rigid body to form an asymmetrical fixed positional arrangement of fiducial markers, wherein the rigid body includes multiple array arms extending in multiple directions from a central region, wherein the multiple array arms substantially combine to define a rigid body plane; and an array coupling arrangement coupled to the rigid body at its central region, wherein the array coupling arrangement is configured to couple the rigid body at its central region to a separate object such that the rigid body is rotatable relative to the separate object about a rotational axis extending through the central region in a direction that is substantially perpendicular to the rigid body plane, the array coupling arrangement being further configured to facilitate locking the rigid body in place at one of multiple fixed rotational positions relative to the separate object.

2. The fiducial marker array of claim 1, further comprising:

the plurality of fiducial markers, wherein the plurality of fiducial markers includes infrared reflective spheres, retroreflective spheres, or infrared-emitting diodes.

3. The fiducial marker array of claim 1, further comprising:

a plurality of fiducial marker couplers, wherein each fiducial marker coupler removably couples one of the plurality of fiducial markers to the rigid body at one of the fixed locations.

4. The fiducial marker array of claim 1, wherein the multiple array arms include three or more array arms and the plurality of fiducial markers includes four or more fiducial markers.

5. The fiducial marker array of claim 1, wherein each of the plurality of array arms includes at least one of the fixed locations that support one of the plurality of fiducial markers.

6. The fiducial marker array of claim 1, wherein the array coupling arrangement includes a shaft having a threaded portion, the shaft being extendable through an opening in the rigid body central region and configured such that its threaded portion mates within a threaded opening at the separate object.

7. The fiducial marker array of claim 6, wherein the rigid body is configured to rotate about the shaft when the shaft is extended through the rigid body central region opening and is mated within the threaded opening of the separate object.

8. The fiducial marker array of claim 6, wherein the array coupling arrangement further includes a thumbwheel coupled to the shaft at an end opposite the threaded portion, the thumbwheel being configured to rotate the shaft to couple and uncouple the shaft from the threaded opening of the separate object.

9. The fiducial marker array of claim 1, wherein the array coupling arrangement includes one or more array locking features along a bottom surface of the rigid body at its central region, the one or more array locking features being configured to interact with one or more separate locking features on the separate object to facilitate locking the rigid body in place at a fixed rotational position relative to the separate object.

10. The fiducial marker array of claim 1, wherein the separate object is a pivotable clamp configured to clamp onto a cylindrical portion of a separate tool such that the pivotable clamp can pivot about a longitudinal axis of the cylindrical portion.

11. The fiducial marker array of claim 10, wherein the separate tool is a surgical probe.

12. The fiducial marker array of claim 10, wherein clamping the pivotable clamp onto the cylindrical portion and locking the fiducial marker array at a fixed rotational position relative to the pivotable clamp results in all fiducial markers remaining at fixed distances from a tip of the tool and also from the longitudinal axis of the cylindrical portion when the pivotable clamp pivots about the cylindrical portion with respect to the longitudinal axis.

13. The fiducial marker array of claim 1, wherein the array coupling arrangement is configured to allow rotation of the fiducial marker array relative to the separate object without uncoupling from the separate object.

14. The fiducial marker array of claim 1, wherein the array coupling arrangement is configured to facilitate locking the rigid body in place at eight or more different fixed rotational positions relative to the separate object.

15. The fiducial marker array of claim 1, wherein the array coupling arrangement is configured to couple the rigid body to the separate object such that rotation of the rigid body about the rotational axis results in rotating the fiducial marker fixed locations in circular motions about the rigid body central region while the fiducial marker fixed locations all remain facing in the same constant direction.

16. A medical fiducial marker system, comprising:

a pivotable medical device clamp configured to clamp onto a cylindrical portion of a separate medical device during a medical procedure, wherein clamping onto the cylindrical portion results in the pivotable clamp being unable to slide laterally along the cylindrical portion while still allowing the pivotable clamp to pivot about the cylindrical portion with respect to a longitudinal axis thereof, and a rotatable fiducial marker array configured to support a plurality of fiducial markers and to rotatably couple to the pivotable medical device clamp, wherein clamping the pivotable medical device clamp onto the cylindrical portion of the separate medical device and locking the rotatable fiducial marker array at a fixed rotational position relative to the pivotable medical device clamp results in each of the plurality of fiducial markers remaining at a fixed distance from a tip of the separate medical device and from the longitudinal axis when the pivotable clamp pivots about the cylindrical portion.

17. The medical fiducial marker system of claim 16, wherein the rotatable fiducial marker array includes:

a rigid body configured to support the plurality of fiducial markers at fixed locations relative to each other along the rigid body to form an asymmetrical fixed positional arrangement of fiducial markers, wherein the rigid body includes multiple array arms extending in multiple directions from a central region, and an array coupling arrangement coupled to the rigid body at its central region, wherein the array coupling arrangement is configured to couple the rigid body at its central region to the pivotable medical device clamp such that the rigid body is rotatable relative to the pivotable medical device clamp about a rotational axis extending through the central region, the array coupling arrangement being further configured to facilitate locking the rigid body in place at one or more fixed rotational positions relative to the pivotable medical device clamp.

18. The medical fiducial marker system of claim 16, wherein the pivotable medical device clamp includes:

a main body having a top region, a first side region, a second side region opposite the first side region, and a pin extending from the first side region to the second side region;

a first arm arrangement having a top portion, a bottom portion, and a midsection configured to rotate about the pin in a first rotational direction, a second arm arrangement positioned opposite the first arm arrangement and having a top portion, a bottom portion, and a midsection configured to rotate about the pin in a second rotational direction opposite the first rotational direction, wherein the bottom portions of the first and second arm arrangements include nonlinear regions, a clamp coupling component coupled to the first arm arrangement proximate its top portion, wherein the clamp coupling component is configured to rotatably couple the pivotable medical device clamp to the rotatable fiducial marker array, a shaft extending through the top region of the main body, the shaft including a threaded portion below the top region, a twisting component coupled to the shaft above the top region, wherein the twisting component is configured to facilitate rotation of the shaft, and a traveling nut coupled to the threaded portion of the shaft and configured to travel along the threaded portion and to push against the first and second top portions of the first and second arm arrangements when the traveling nut travels sufficiently downward along the threaded portion, wherein pushing against the top portions of the arm arrangements causes the arm arrangements to rotate about the pin such that the arm arrangement nonlinear regions clamp onto the cylindrical portion of the separate medical device placed therebetween.

19. A method of using a rotatable fiducial marker array, the method comprising:

facilitating a rotational coupling between a rotatable fiducial marker array and a separate object, wherein the rotatable fiducial marker array includes a rigid body having a central region and multiple array arms extending therefrom configured to support a plurality of fiducial markers at fixed locations relative to each other to form an asymmetrical fixed positional arrangement of fiducial markers, wherein the multiple array arms substantially combine to define a rigid body plane, wherein the rotatable fiducial marker array further includes an array coupling arrangement coupled to the rigid body at its central region, and wherein the array coupling arrangement is configured to couple the rigid body at its central region to the separate object such that the rigid body is rotatable relative to the separate object about a rotational axis extending through the central region in a direction that is substantially perpendicular to the rigid body plane;

adjusting a rotational orientation of the rotatable fiducial marker array relative to the separate object from a first rotational position to a second rotational position; and locking the rotational coupling at a fixed rotational position between the rotatable fiducial marker array and the separate object, wherein the locked rotational coupling prevents rotational movement of the rotatable fiducial marker array relative to the separate object.

20. The method of claim 19, wherein the separate object is a pivotable clamp configured to clamp onto a cylindrical portion of a separate tool, further comprising the steps of:

coupling the plurality of fiducial markers to the rotatable fiducial marker array at the fixed locations; and calibrating fiducial marker positions on the rotatable fiducial marker array relative to both a longitudinal axis of the separate tool cylindrical portion and a tip of the separate tool when the rotational coupling is locked at the fixed rotational position and the pivotable clamp is clamped onto the separate tool cylindrical portion.

* * * * *